(12) United States Patent
Thum et al.

(10) Patent No.: US 11,186,838 B2
(45) Date of Patent: Nov. 30, 2021

(54) LNCRNA MEG3 FOR THERAPY AND DIAGNOSIS OF CARDIAC REMODELLING

(71) Applicant: Medizinische Hochschule Hannover, Hannover (DE)

(72) Inventors: Thomas Thum, Hannover (DE); Maria-Teresa Piccoli, Hannover (DE); Janika Viereck, Hannover (DE); Shashi Kumar Gupta, Hannover (DE)

(73) Assignee: MEDIZINISCHE HOCHSCHULE HANNOVER, Hannover (DE)

( * ) Notice: Subject to any disclaimer, the term of this patent is extended or adjusted under 35 U.S.C. 154(b) by 363 days.

(21) Appl. No.: 16/098,793

(22) PCT Filed: Apr. 26, 2017

(86) PCT No.: PCT/EP2017/059984
§ 371 (c)(1),
(2) Date: Nov. 2, 2018

(87) PCT Pub. No.: WO2017/191021
PCT Pub. Date: Nov. 9, 2017

(65) Prior Publication Data
US 2019/0136236 A1    May 9, 2019

(30) Foreign Application Priority Data

May 2, 2016    (EP) .................................... 16167961

(51) Int. Cl.
*C12N 15/113*    (2010.01)
*C12Q 1/6883*    (2018.01)

(52) U.S. Cl.
CPC .......... *C12N 15/113* (2013.01); *C12Q 1/6883* (2013.01); *C12N 2310/113* (2013.01); *C12N 2310/20* (2017.05); *C12N 2310/315* (2013.01); *C12N 2310/3231* (2013.01); *C12N 2310/341* (2013.01); *C12N 2310/346* (2013.01)

(58) Field of Classification Search
None
See application file for complete search history.

(56) References Cited

U.S. PATENT DOCUMENTS

2009/0023142 A1 * 1/2009 Cheung ................ C12Q 1/6886
435/6.16
2018/0245081 A1 * 8/2018 Lee ...................... C12N 15/113

FOREIGN PATENT DOCUMENTS

WO    2007097741 A1    8/2007
WO    2011087154 A1    7/2011

OTHER PUBLICATIONS

Piccoli et al., Circulation Research vol. 121:575-583, Aug. 18, 2017.*
Wang, et al., "Noncoding RNA in cardiac fibrosis," International Journal of Cardiology, vol. 187, 2015, pp. 365-368.
Janssen, et al., "Cardiac Expression of Deiodinase type 3 (Dio3) Following Myocardial Infarction Is Associated With the Induction of a Pluripotency microRNA Signature from the Dlk1-Dio3 Genomic Region," Endocrinology, vol. 154, No. 6, 2013, pp. 1973-1978.
Piccoli, et al., "Non-coding RNAs as modulators of the cardiac fibroblast phenotype," Journal of Molecular and Cellular Cardiology, vol. 92, 2016, pp. 75-81.
Creemers, et al., "Function and Therapeutic Potential of Noncoding RNAs in Cardiac Fibrosis," Circulation Research, vol. 118, No. 1, 2015, pp. 108-118.
Boon, "Non-Coding RNAs in cardiovascular aging," Acta Physiologica, vol. 213, No. S699, S4-02, 2015, p. 17.
Clark, et al., "miR-410 and miR-495 Are Dynamically Regulated in Diverse Cardiomyopathies and Their Inhibition Attenuates Pathological Hypertrophy," PloS One, vol. 11, No. 3, Article No. e0151515, 2016, pp. 1-14.

* cited by examiner

*Primary Examiner* — Sean McGarry
(74) *Attorney, Agent, or Firm* — Arent Fox LLP

(57) ABSTRACT

The present invention relates to a compound inhibiting the expression and/or the activity of maternally expressed 3 (Meg3) for use in treating or preventing cardiac remodelling.

7 Claims, 25 Drawing Sheets

Specification includes a Sequence Listing.

Figure 1
A
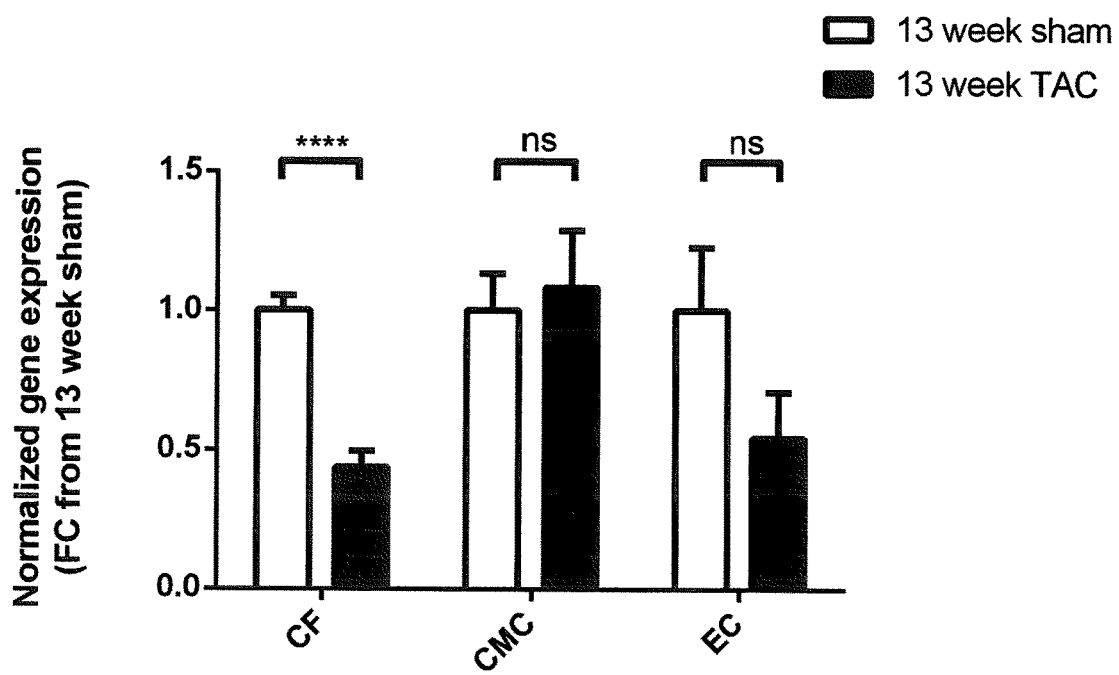
B
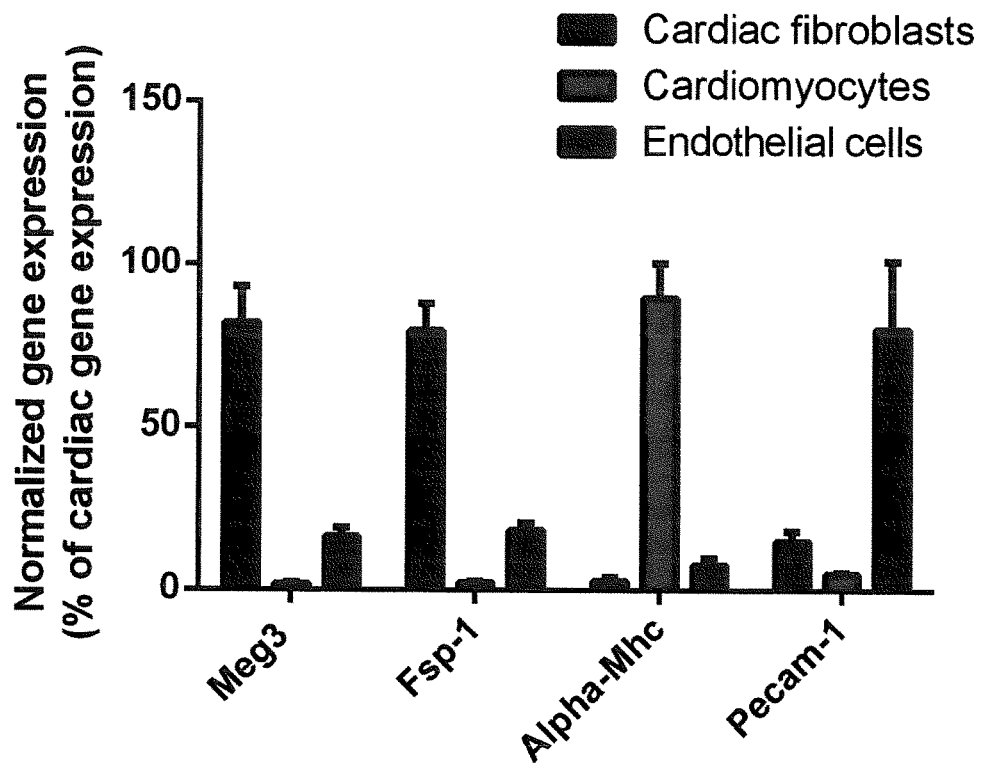

Figure 2
A
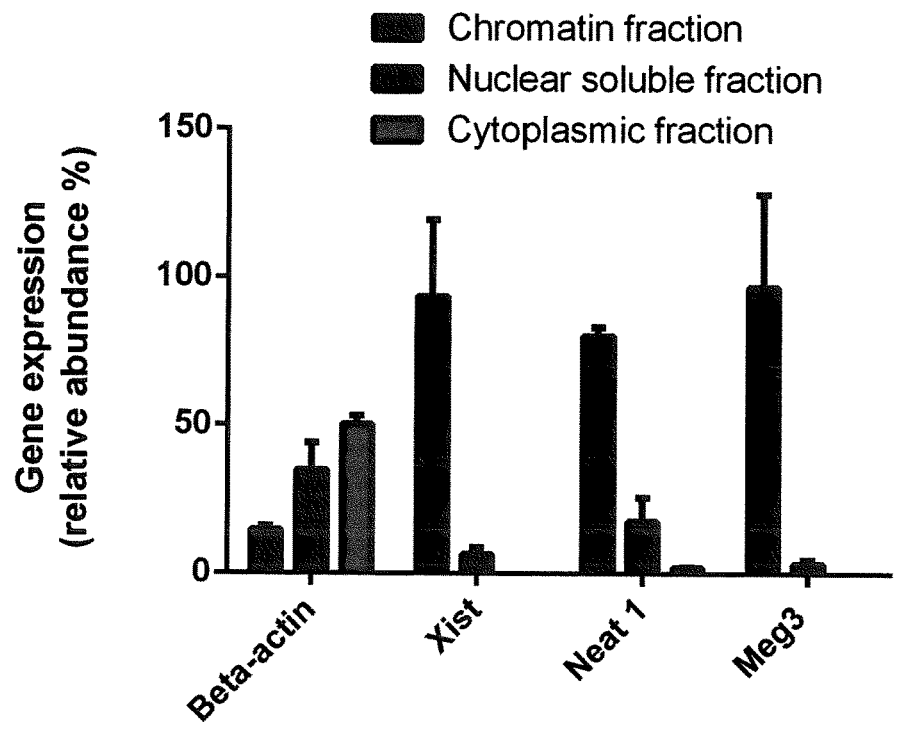
B
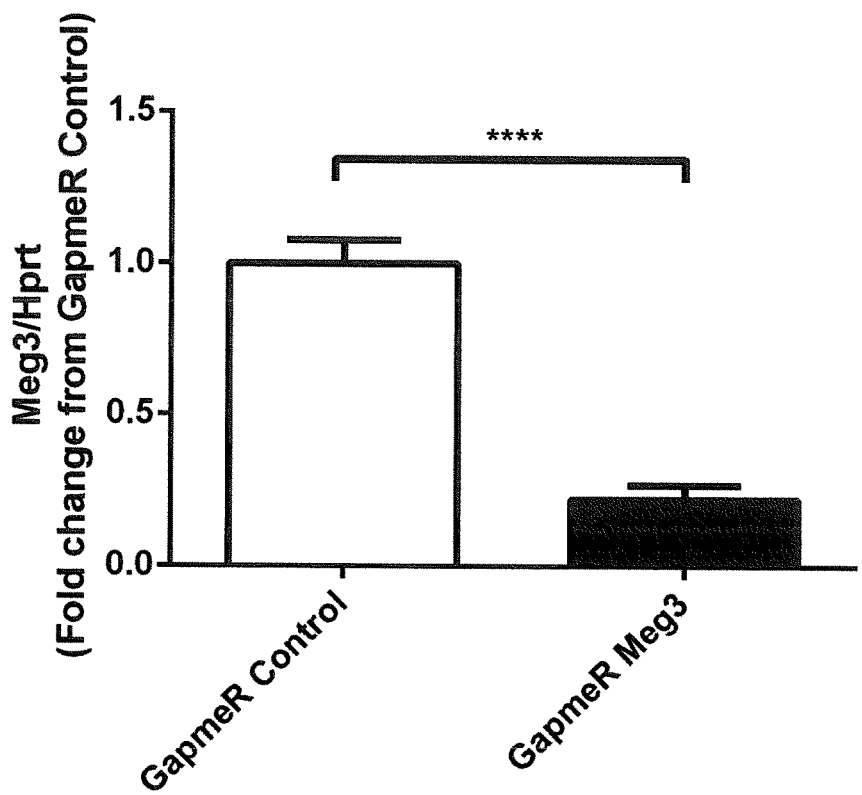

A

GapmeR Ctrl    GapmeR Meg3

Figure 3:
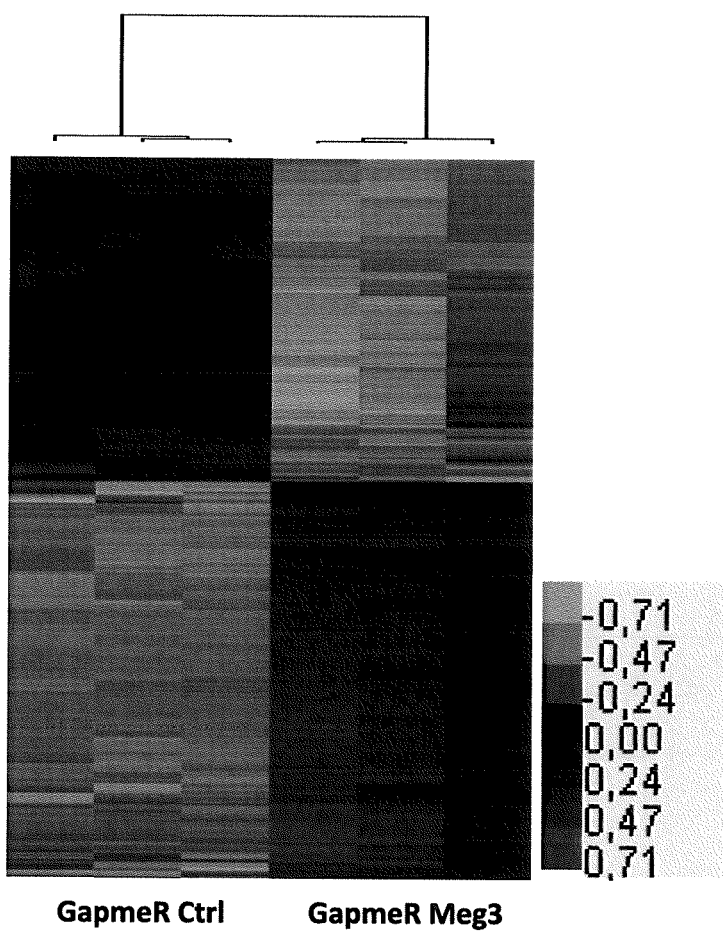

Figure 3 – continued
B
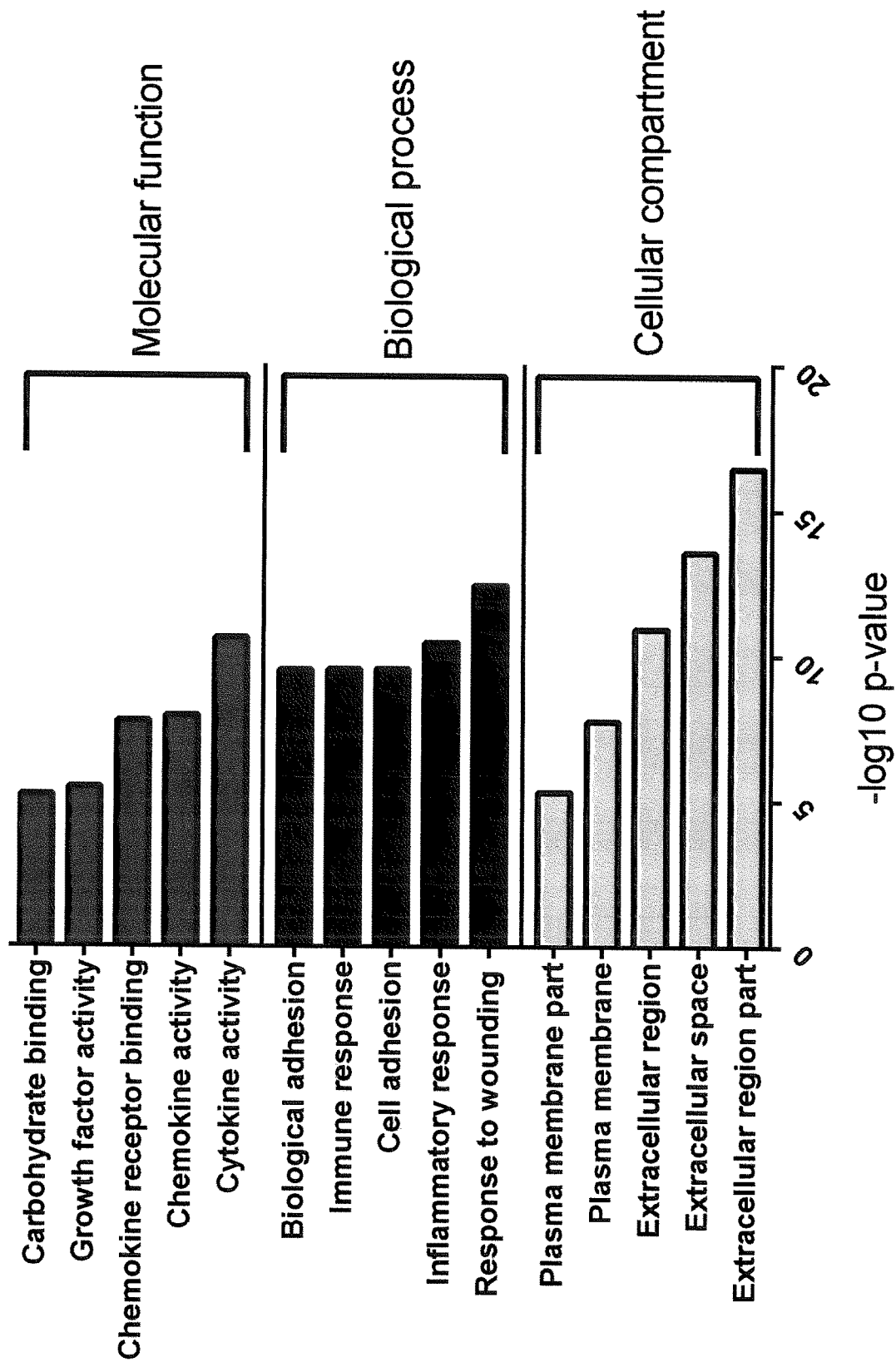

A

Figure 4:
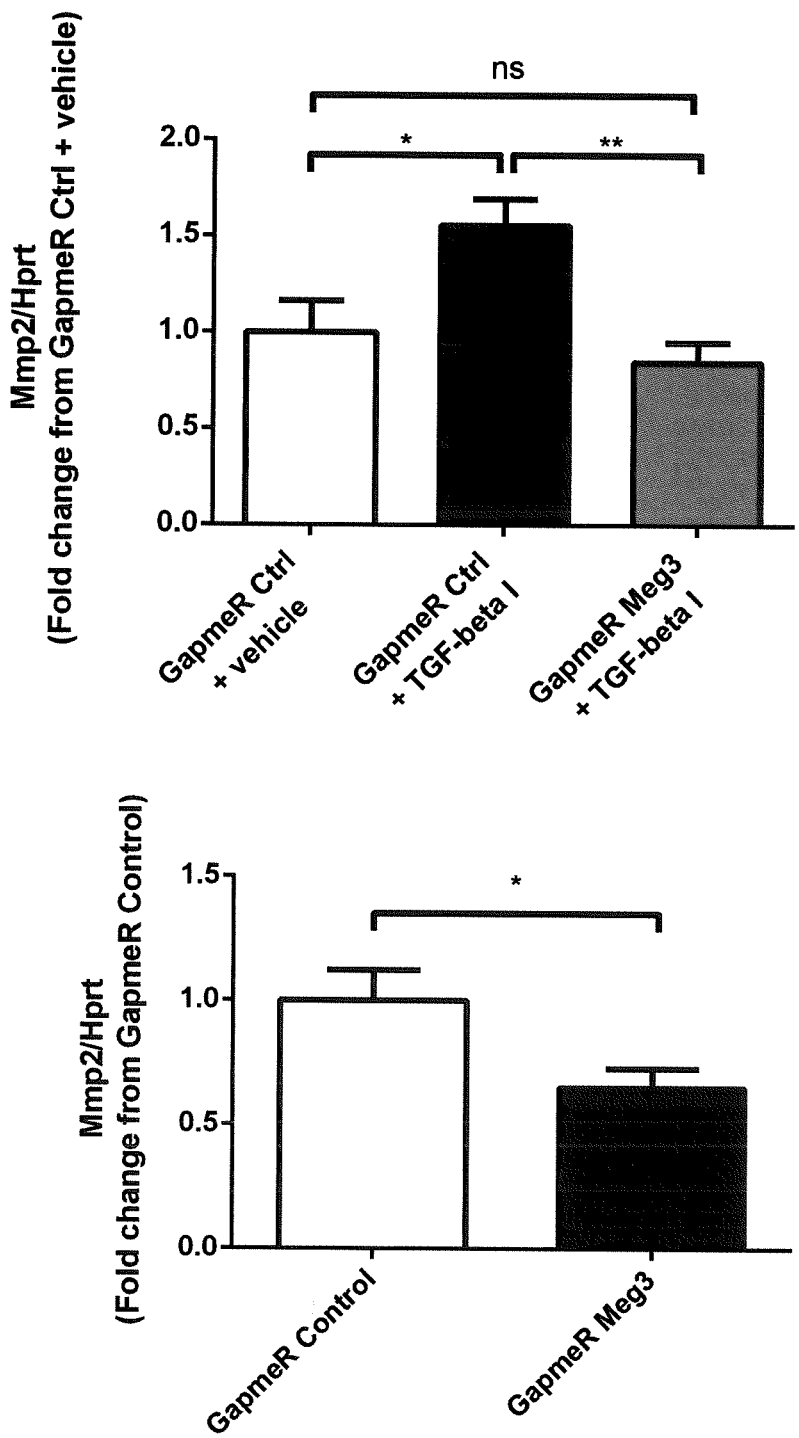

Figure 4 – continued
B
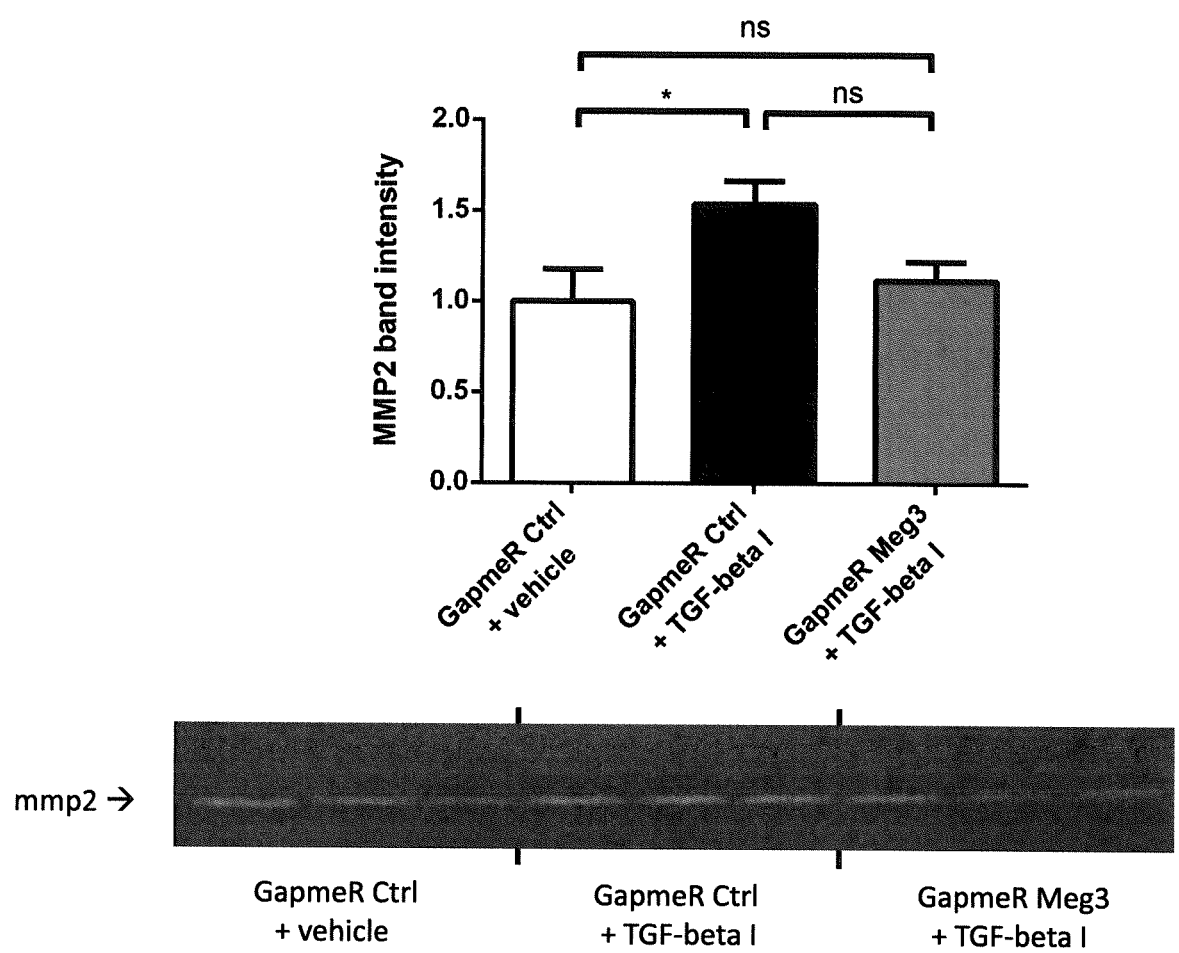

Figure 5
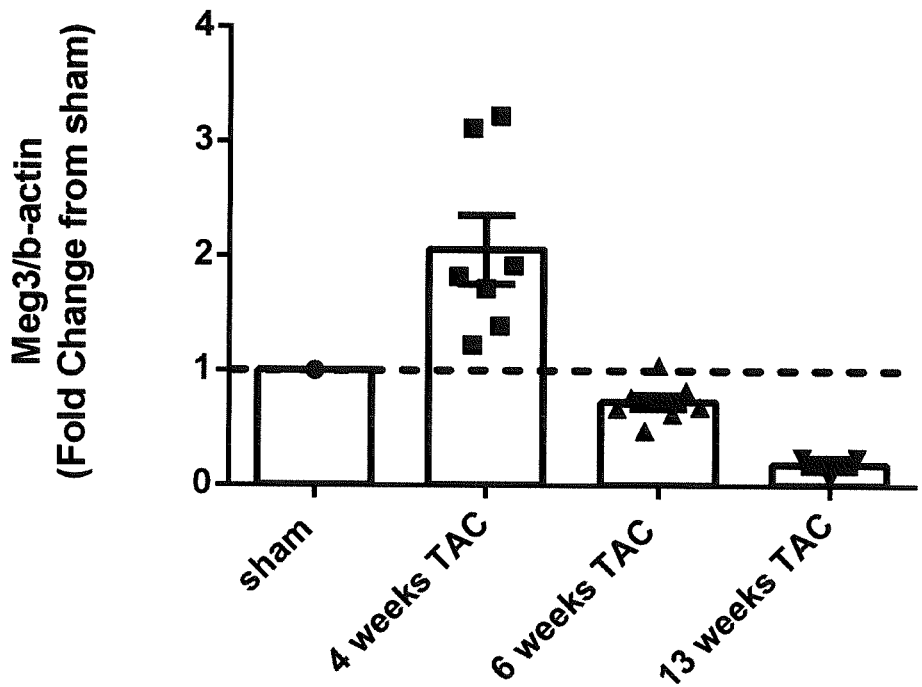
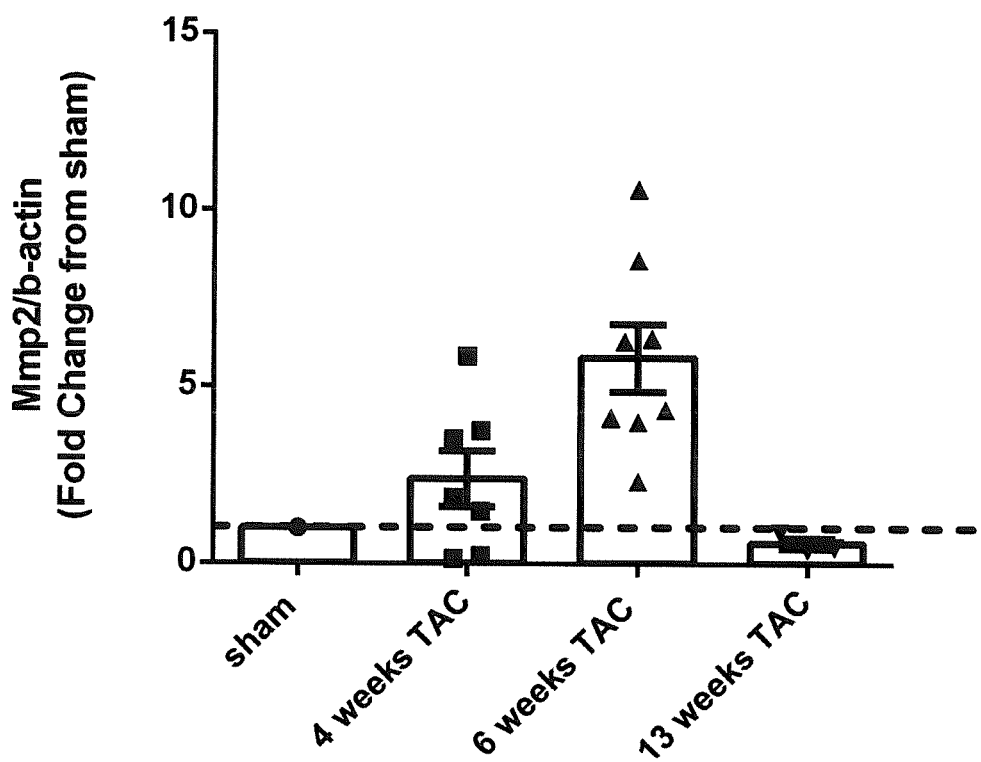

Figure 6
A
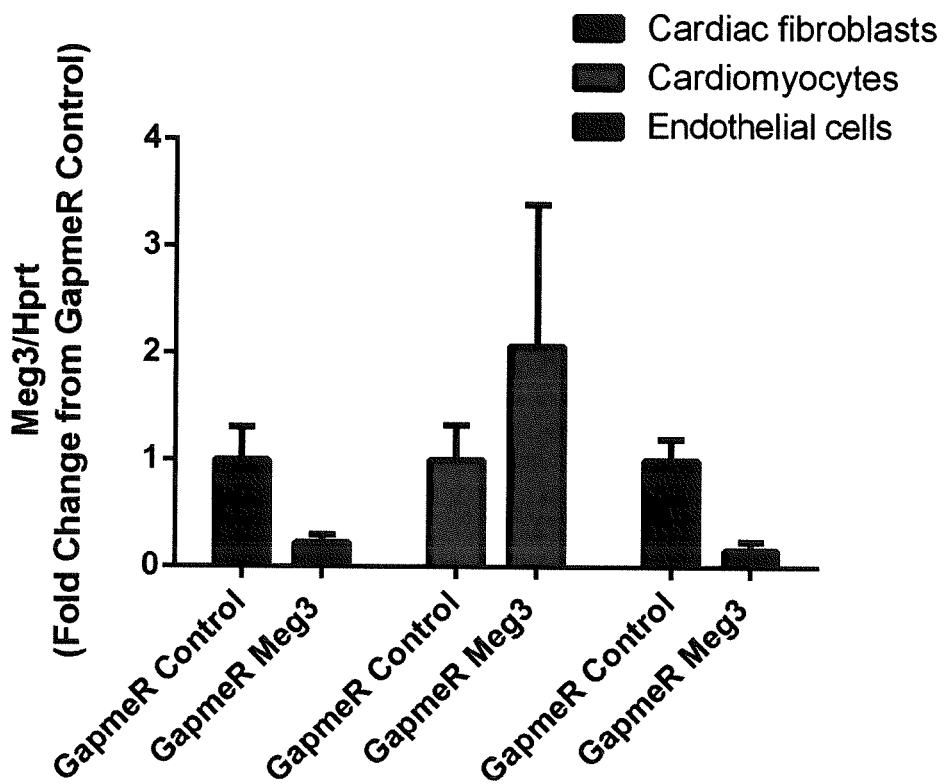
B
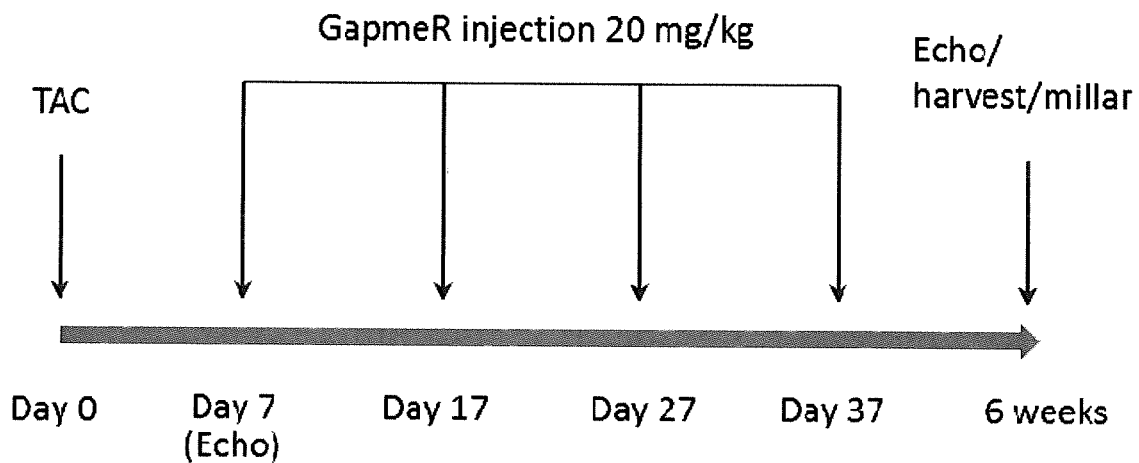

Figure 7
A
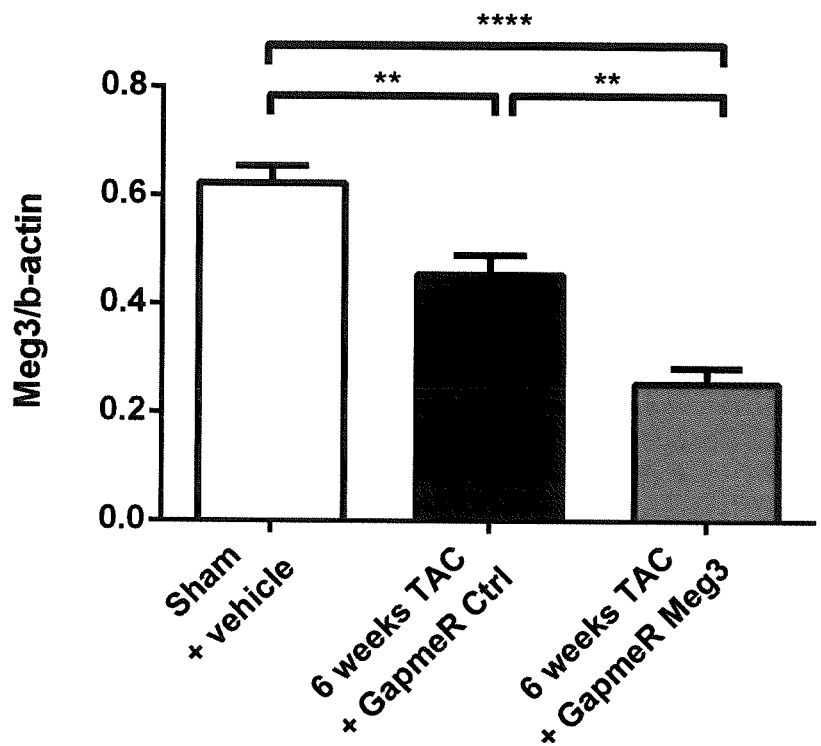
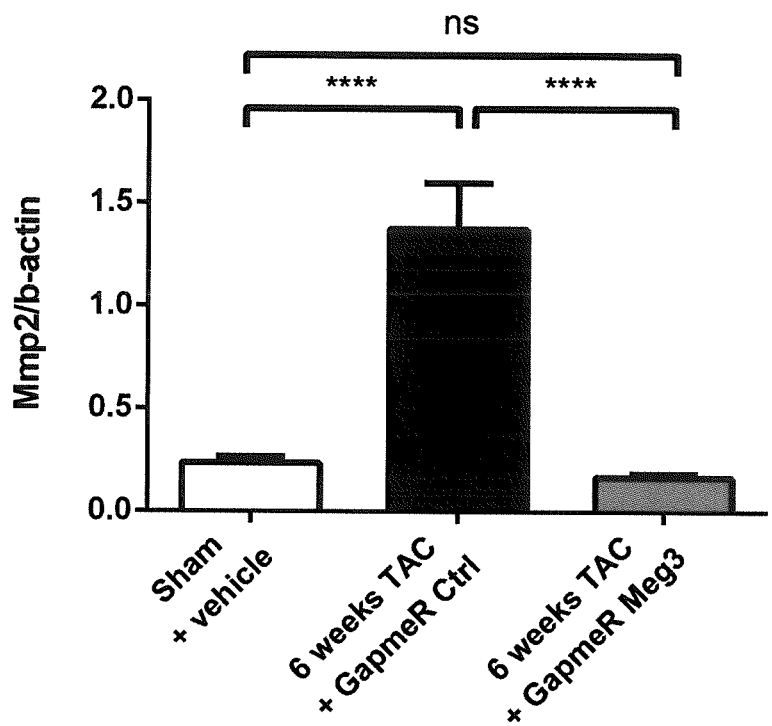

Figure 7 – continued
B
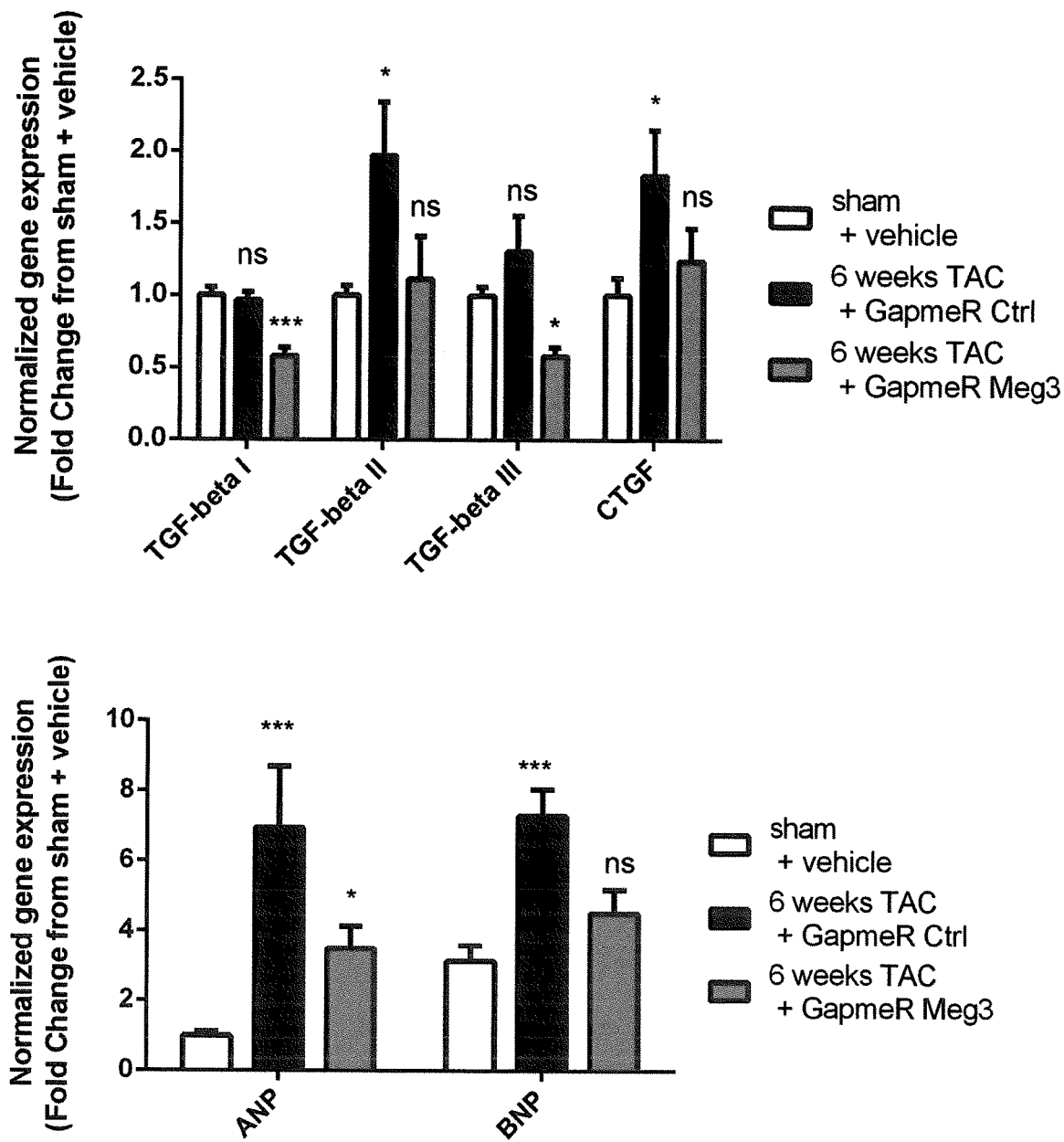

Figure 7 – continued
c
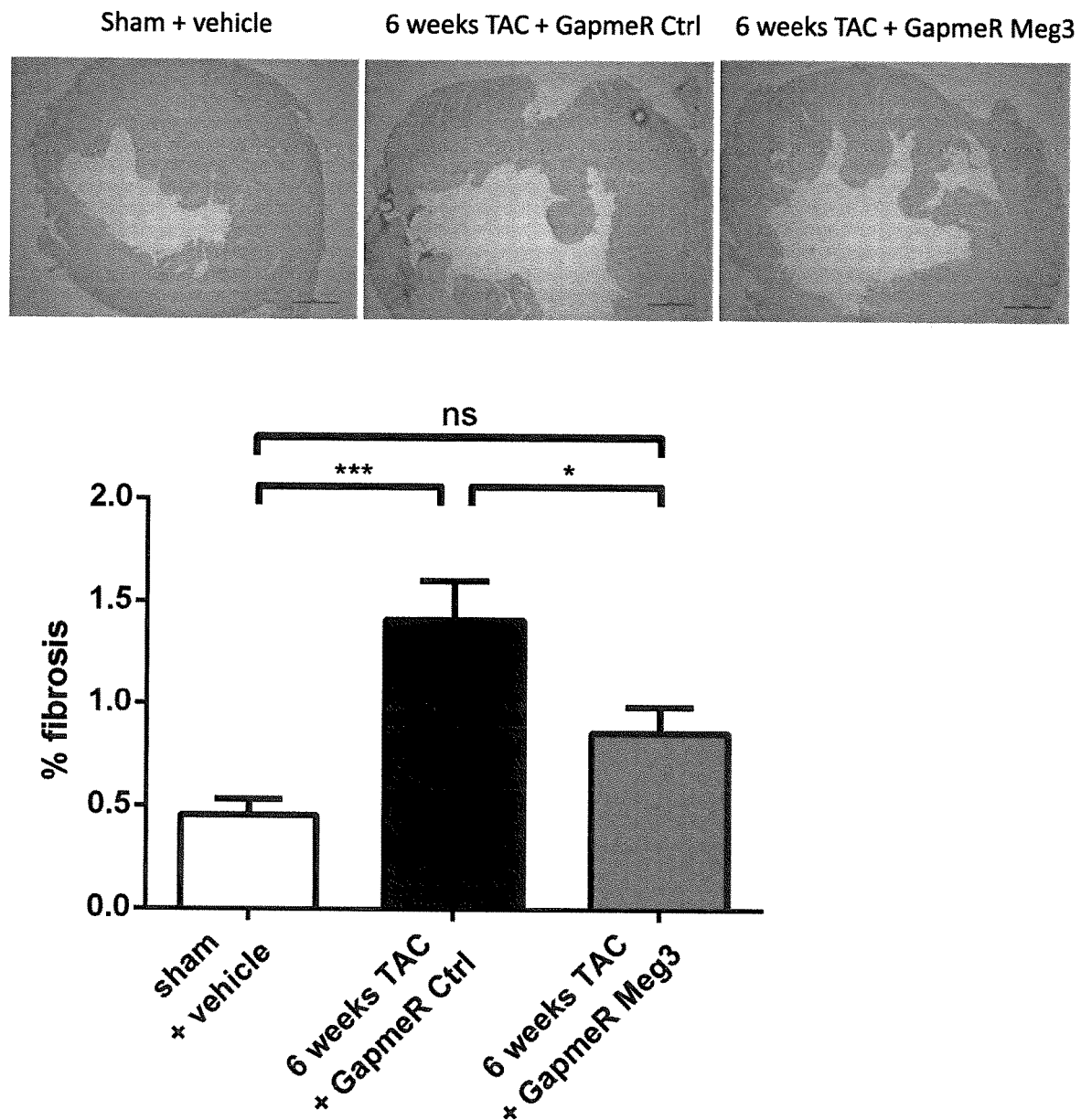

Figure 7 – continued
D
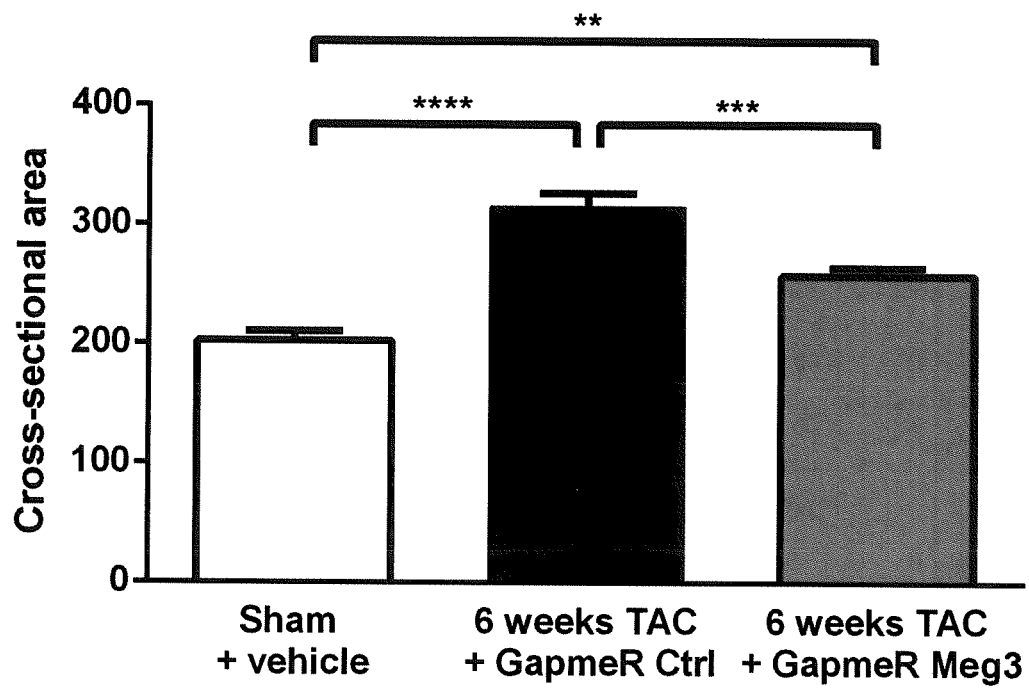
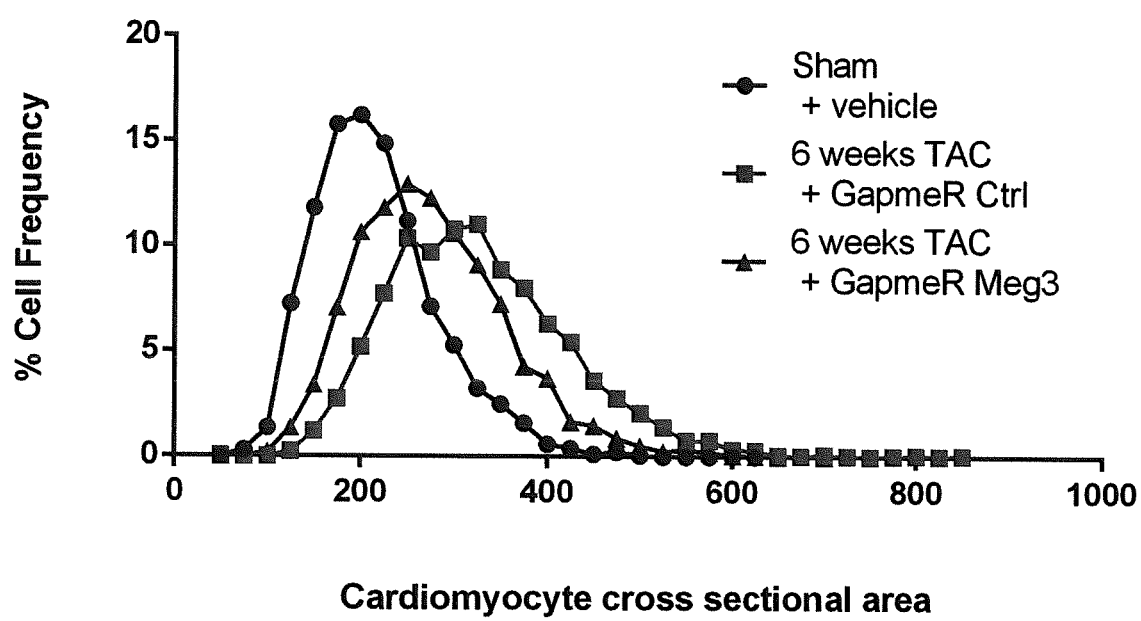

Figure 9
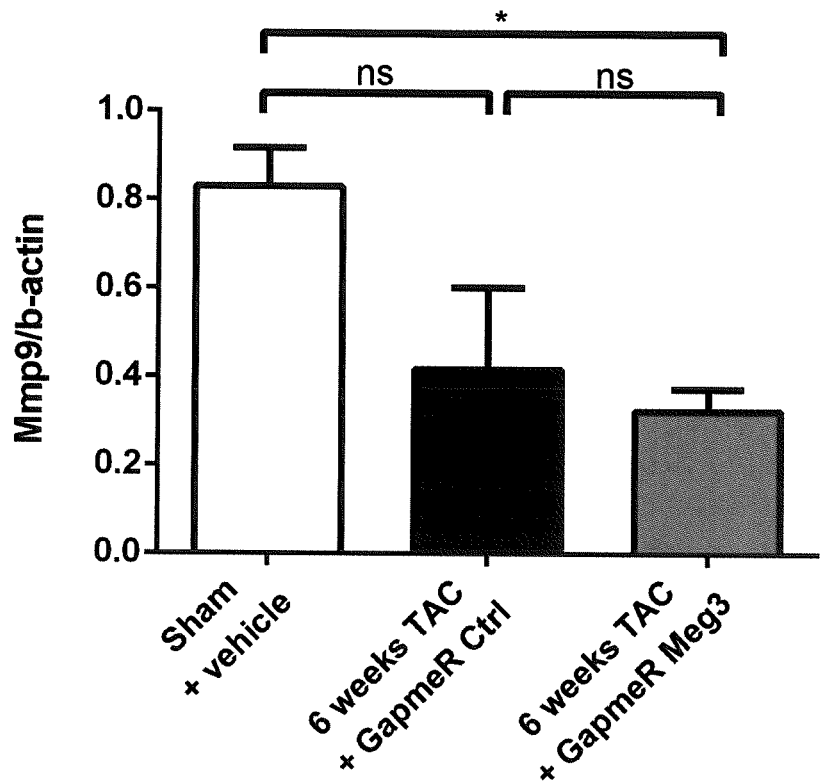
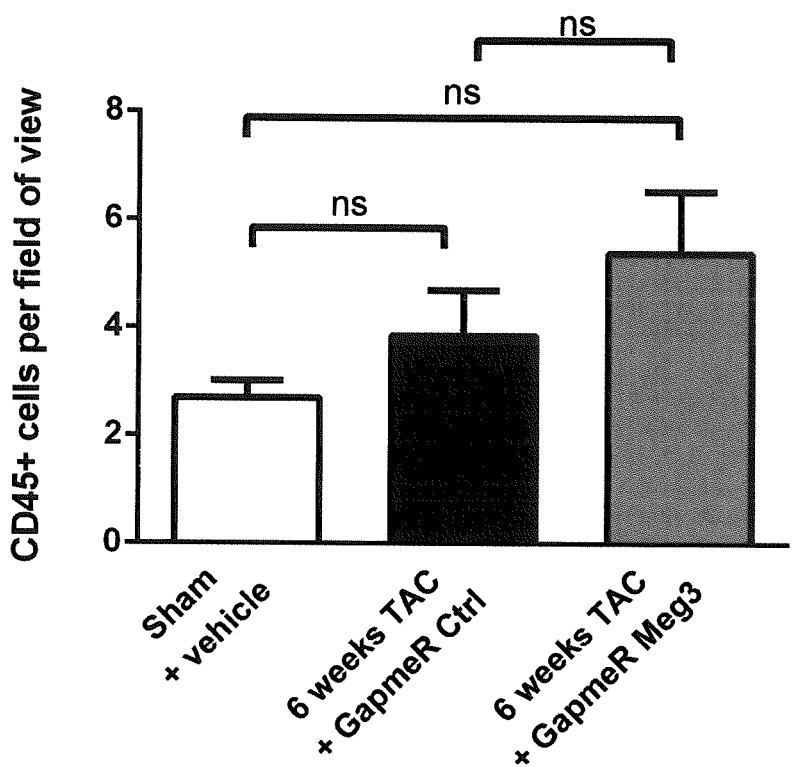

Figure 10
A
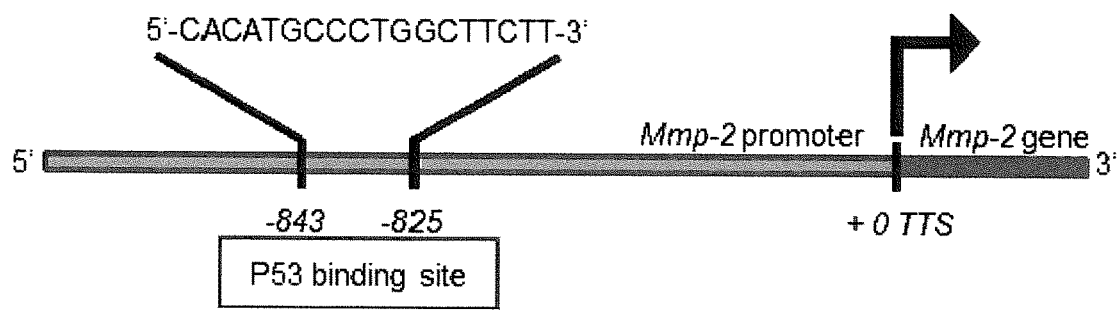
B
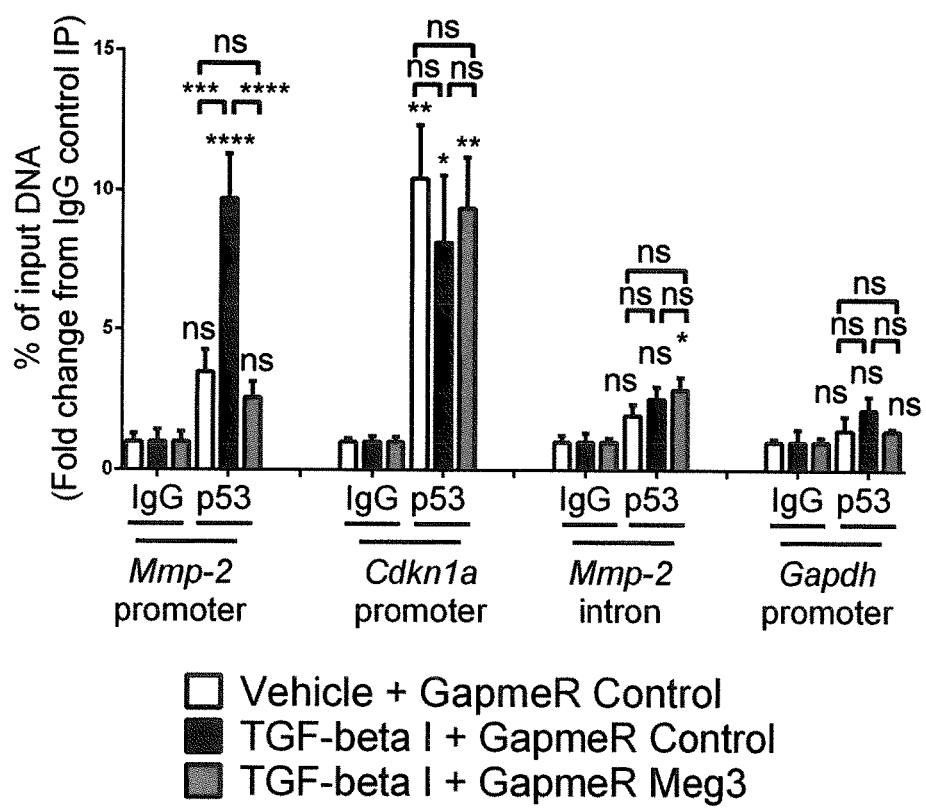

Figure 11
A
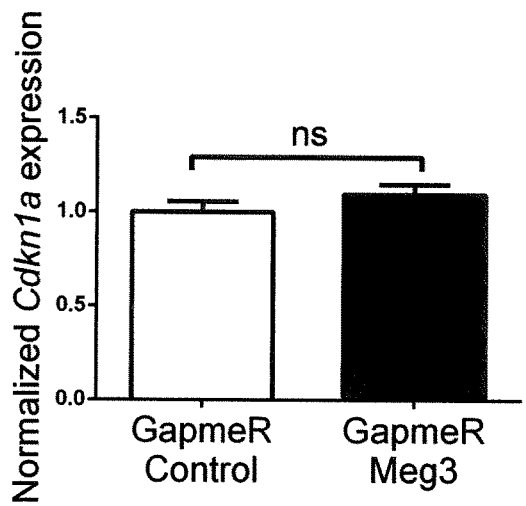
B
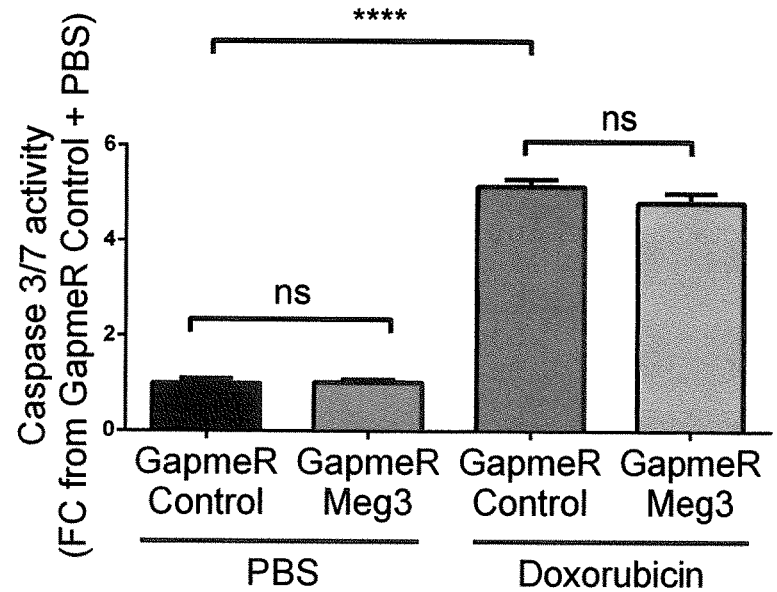
C
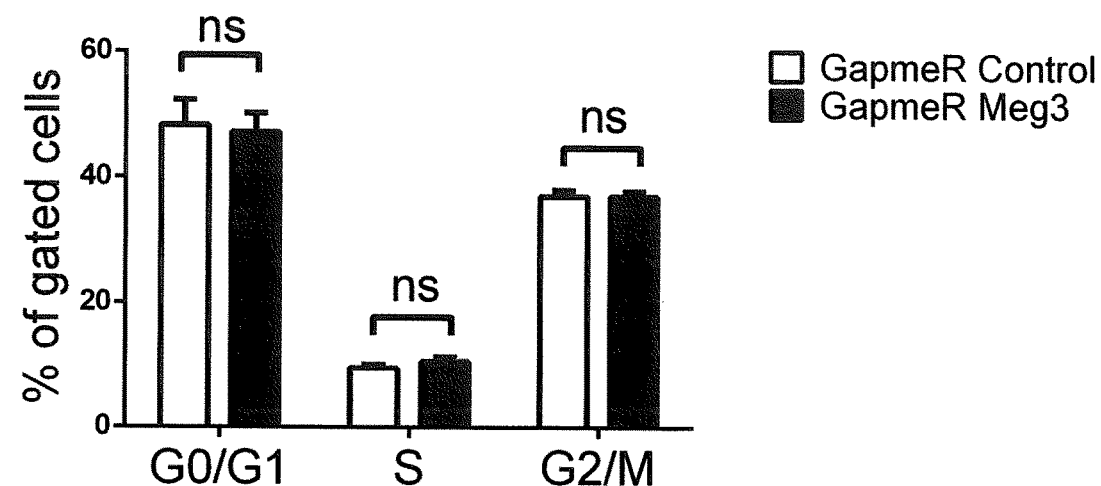

Figue 14
A
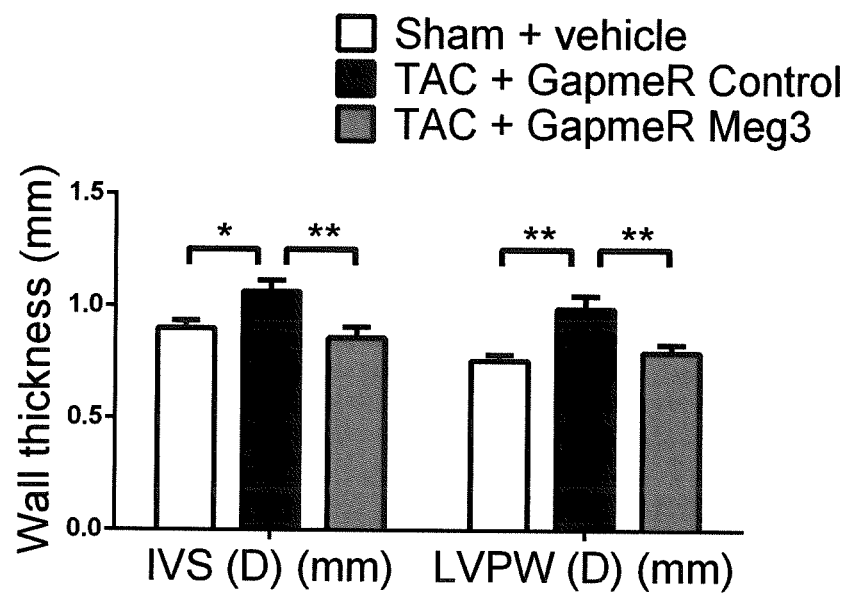
B
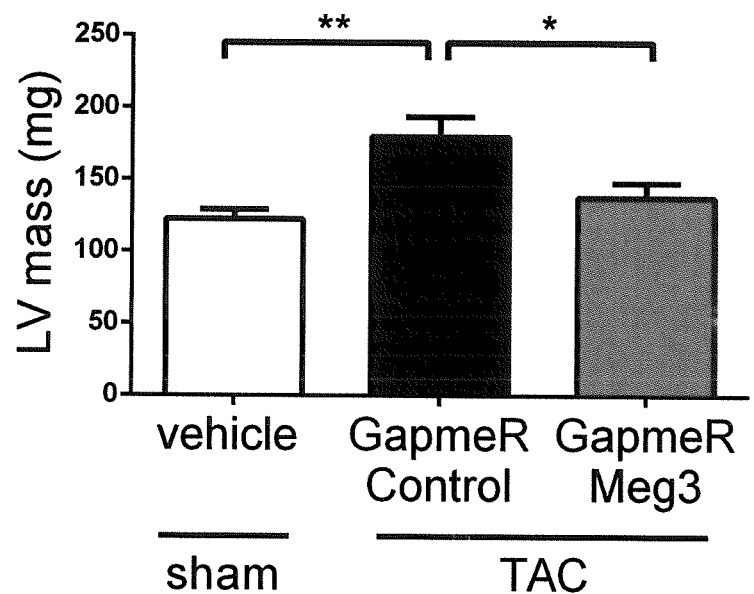

Figure 15
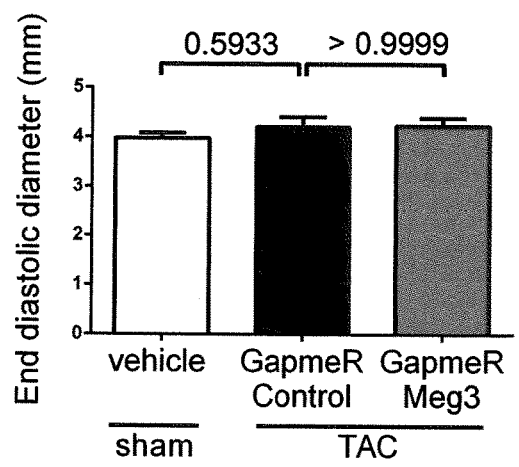
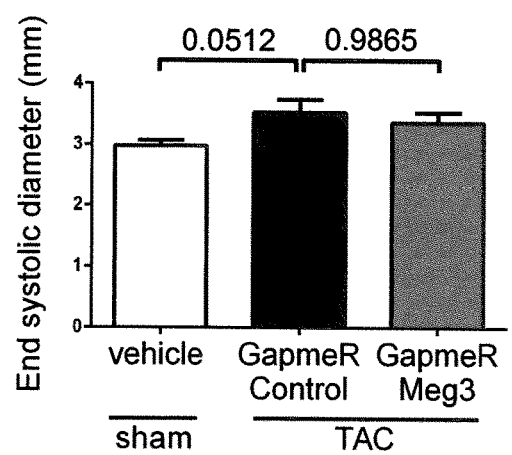
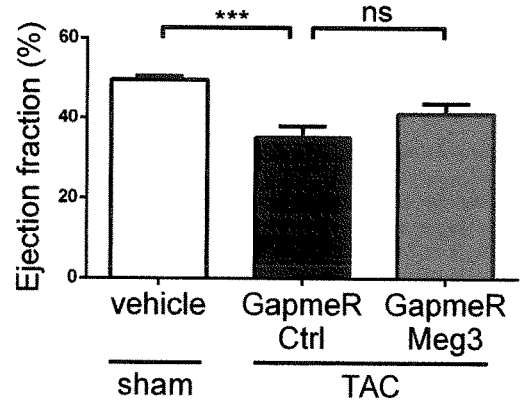
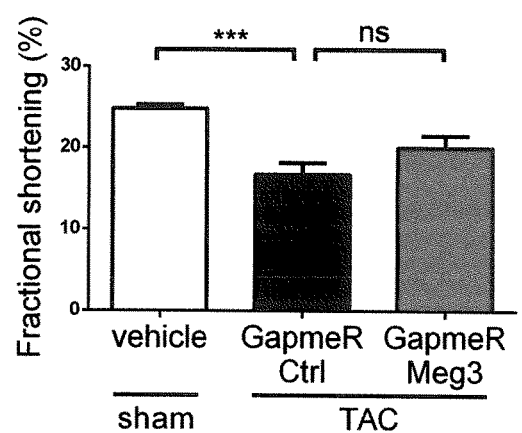

Figure 16
A
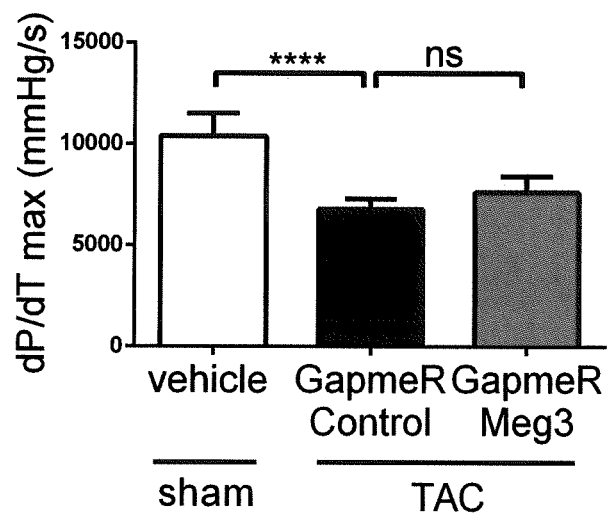
B
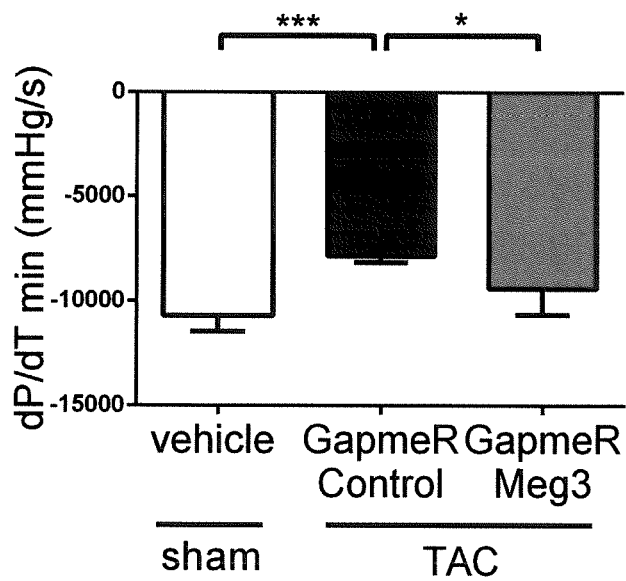

A

Figure 17:
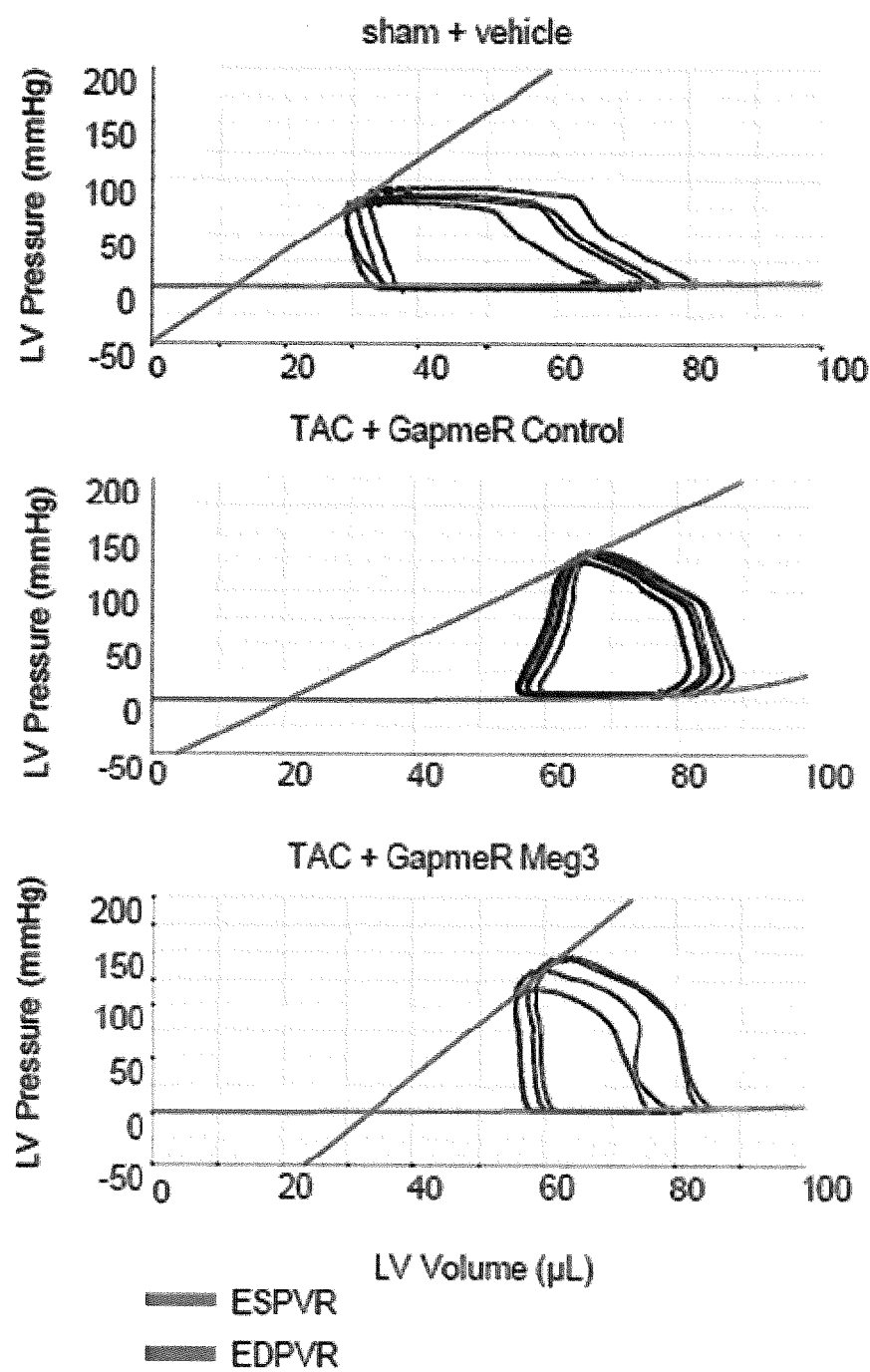

Figure 17 – continued
B
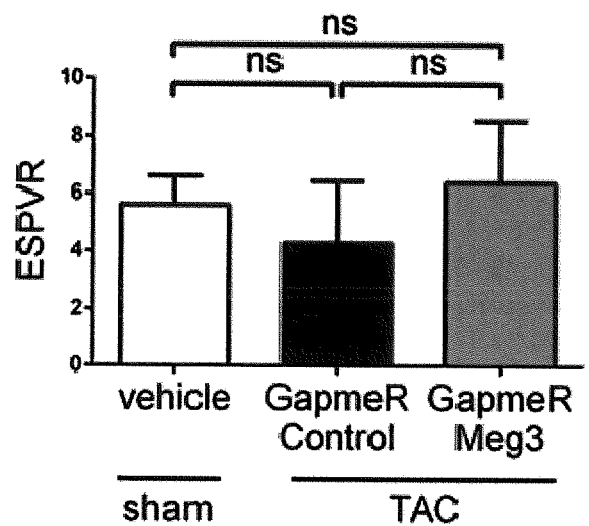
C
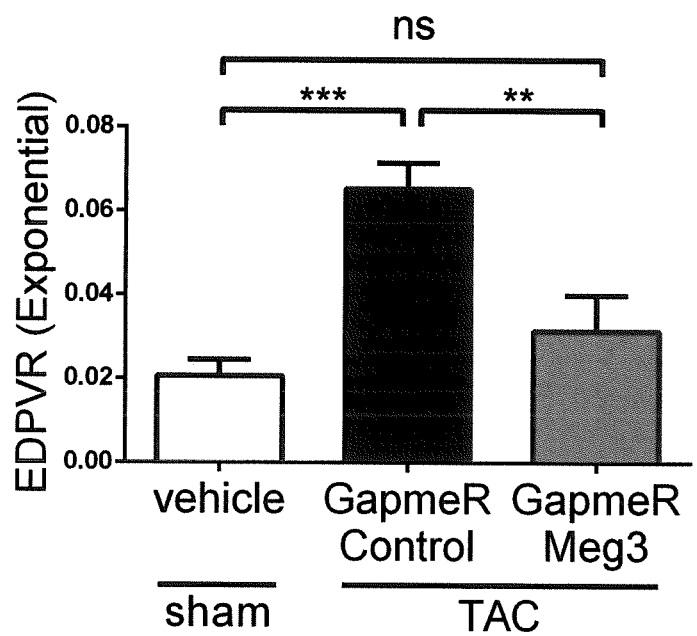

Figure 18:
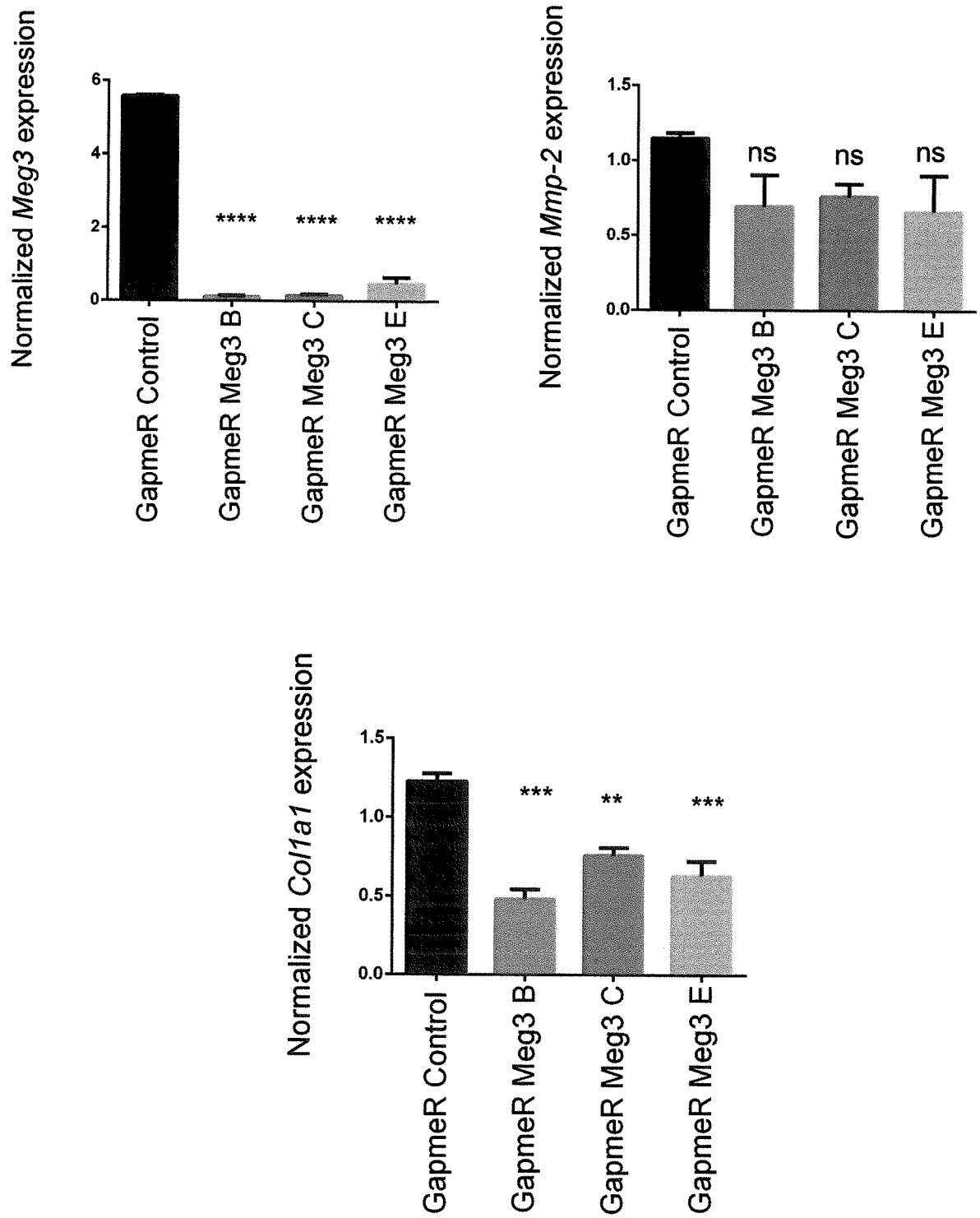

Figure 18 –continued
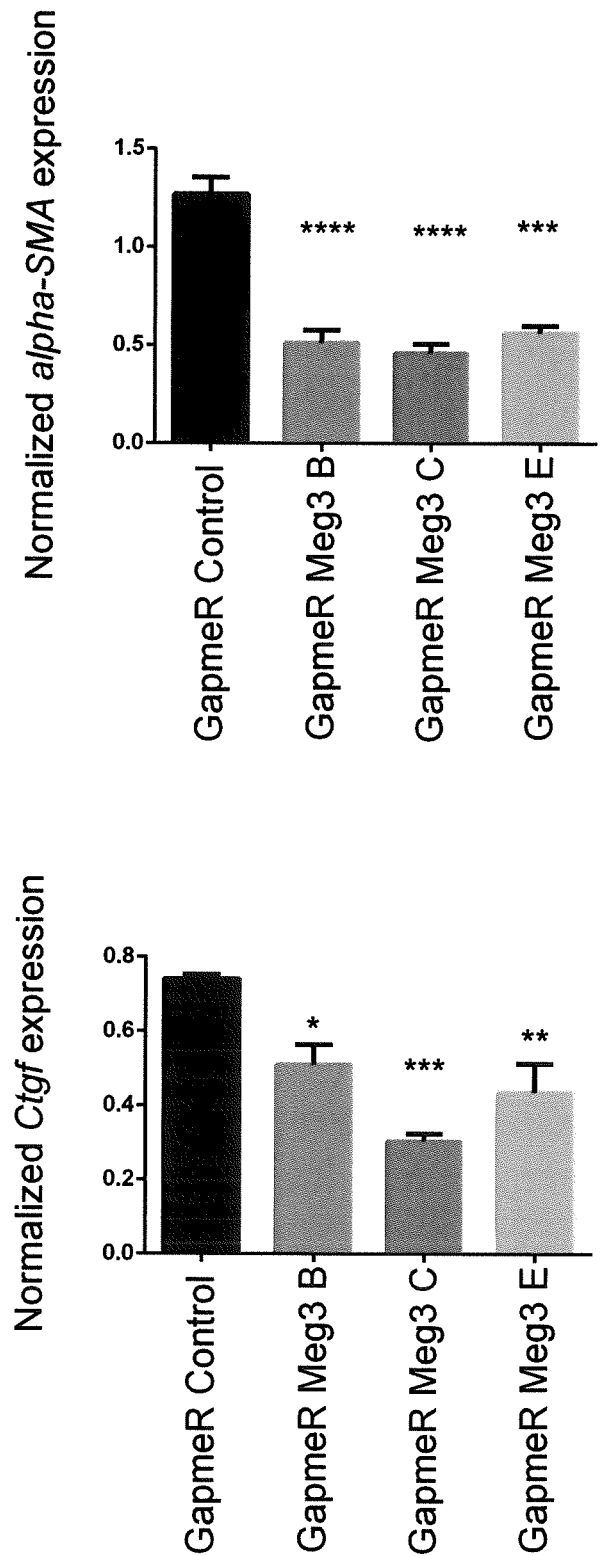

SEQUENCE LISTING

```
<160> NUMBER OF SEQ ID NOS: 73

<210> SEQ ID NO 1
<211> LENGTH: 1896
<212> TYPE: DNA
<213> ORGANISM: Mus musculus
<220> FEATURE:
<223> OTHER INFORMATION: Mouse Meg3 isoform 1 (ENSMUST00000143836)

<400> SEQUENCE: 1
gacgaagagc uggaauagag cucgccucgg cucugcuggc cuuggcugca gcucuuccag      60
aaacccgggg cgcccacaga agaaucucuu accuggcucu cucuucaggg augacaucau     120
cggcucacac cagucuucca ggaccaccuu cuggaugcca aggcugcugc ucgaguaccu     180
gcugugcacc ucuaccuccu gguacsccag ccacucccuc aaguugccug cauguuauau     240
ggccuagcca aggagcacgg auuccaggaa cccacuacca uacagagcaa cuccuugugg     300 acccccugg gaucaggaca gcgagggaca agcgacaaag aggaucauca guggccagcu     360
aguuucucug ggguucaaac cuugaaccag ugcccuagug aggggggcacu ggccauggcc     420 cuugaccuuu gcucugcuug ugucuugagu cugagcccuu uccuguacau cugugcucgu     480
guucaucugc uagugaacug gagugcugcc cuccccgagg agggucgucc cuugugacug     540
aucaugcugu ccuaacaaug uccugagcaa aagggucccu uugggaaccu cucaggaggg     600
ggacccgggu caggggcgac cagcaucuug cuggcaacuc cguggguggg gugggguggg     660
gugcuuccuu cuggaaugag cacguggcug accccccaag gcauguccc uccccccuccu     720 ccacccaccu ucucggagau gucccuuuug ggguaguggg gacauuagga gcaaccuccu     780 agggguuguug ugagaauuaa augaacugca gcagccugag gcagggcugg gcagagaccu     840
cagcacaugu uuguugaaag guuugcaggu ggaucuaguc cucccguuca uggcucaugu     900
gucucaacca uucucucgca gacuccugca gccccuaugc ccagggcucu ccuugcgcca     960
gagguaggug ggaaagagaa cugggagagc ccggacucac ucaugagauu gaacuuaaau    1020
ucacacggag gacacuugga cucuugccac auuagccccg gcuucucgag gccugucuac    1080
acucgcugcu uuccuuccuc accuccaauu uccccuccaa cccacugcuu ccugacucgc    1140
ucuucuccau cgaacggcuc ucgcucaggu uuaaggcuug gcuugcuggc ccuggagauc    1200
ccgucgccgu cuucgucgaa cucgaaaucc uagccaucgu ccuccccugg ccugucgcgu    1260
cuuccugugc cauuugcugu ugugcucagg uuccacgagc ugcccaucuc cacagaagag    1320
```

```
cagcuggcau ugcccaccgg ccaugccggc ugaagaaaag aagacugagg accccaggau    1380
gcccagcgcg aggaccccag gaagcccagc gcgaggacuc cacccacgac gcccagcgcg    1440
aggacuucac gcacaacacg uugcaacccu ccuggauuag gccaaagcca ucaucuggaa    1500
uccugcgugg gacccuggac acacggacac agacaccugc ccccaggacc cuccaacugu    1560
aaaucccucu acagccacgg ggacgccuug cacauuuccu gugggacaug cuggacccaa    1620
gacucuggac ccuggccucc ccuugaguag agagacccac cuacgacugu augaacugcg    1680
cugacccugg ggucaggcau guggccuuga ucccuaccca uggacccuga cuuggggg     1740 ggugggagaa aggcuguugu gucuucacug uugagucuac aucugugaaa ugggcucagg    1800
uuccuaccuc acagggcugu gugaggcag ccgcaaugug cuuagaagca uggggccuag     1860
uggcucaugg ugcuuucaau aaauuucuug uuuuaa                              1896
```

<210> SEQ ID NO 2
<211> LENGTH: 14548
<212> TYPE: DNA
<213> ORGANISM: Mus musculus
<220> FEATURE:
<223> OTHER INFORMATION: Mouse Meg3 isoform 2 (ENSMUST00000146701)

<400> SEQUENCE: 2

```
ggaaagccag guugucuacc ccacagagcg cuucugaaga ccaaacuaca uaacucacaa      60
gaaagugccu uguaaaucgc ccggaaauug caaaaaaaaa auccuuaauu agccaaugag     120 gcuguccua cugcccagcg gccagcccua gucucucaca acagugagca cccaguaggu      180 gcugggguguc uuuguguuca acaaauaauu uccagaauuc aaacaaacaa acaaacaaac    240
aaacaacauu cauucaacaa acauuuucug agacacugac caugugccca gugcaccagg    300
cuauggcuga gguacaaaga caaugagaac agucucuuuu uggaggcuaa uuaguacucu    360
cauuucuacc agcacuuucu uuggccuuuu aaaccaacca uuuuugucca gacaagacca    420
aaaaaaaaaa aaaacaaaaa acaaaaaaca aacaaaaaca aaaacccaa aaaaacaaaa     480 aacaaaacaa cugggguugcu uuagggaagc ccggcuugga guggacaaug ugguccaggc    540
cccugaaagg ggcugauugg auuaugaggc aaauggagga agaaggagca cgcaggagac    600
aaaugcagug ggcggagacc cgcucugagu uaaucaggcu gauugaaggg accuuuucug    660
ucuugccgag uggcccgggg gggcucucac uagugcacug cugugugcac auggagacug    720
gagcuacccu gguccucuc uggcaacugu ucauucauuu gaugcucaca acucccuguc    780
cugacccagg gccggccugc caucacgcag ggaagcagag gucgccaagc gguuuccgac     840 ggggccccc cacauaacgu uagccucgcg gucucuucgg uuuuagcagc aguggacaug     900
aaccuguuuc cagccugcau ccuccaguuc cucucgggac ccuggcuccc acugugcuca     960
ccuggagccc cgccagcccg ccucccccug uccuccuucc ucgccacucc aguucugu    1020 uuuccuucac agccccggcu cucgaggcc ugucuacacu cgcugcuuuc cuuccucacc     1080
uccaauuucc ccuccaaccc acugcuuccu gacucgcucu ucccaucga acggcucucg     1140 cucaggccug ucgcgucuuc cuggccauu gcguguugu ucagguucc acagagcugc      1200 caucuccaca gaagagcagc uggcauugcc caccggccau gccggcugaa gaaagaaga     1260 cugaggacc caggaugccc agcgcgagga ccccaggaag cccagcgcga ggacuccacc    1320
cacgacgccc agcgcgagga cuucacgcac aacacguugc aaccuccug gauuaggcca     1380 aagccaucau cuggaauccu gcgugggacc cuggacacac ggacacagac accugccccc    1440
```

-continued

```
aggacccucc aacuguaaau cgauuggaag cgcccuugug agcugggggcc uucaaagggc    1500 ugaggagaaa augcaggccg agagaccagc uucucaaaua ggcuucaagc cuccaugacc    1560
ugagcucacc cccuggaaau gucuggaaaa cauaauggc agguuuucug ucuucaaagu    1620
uuccaucaaa accucuucaa guucuuuauu guuuaggacu gagacacuug gggacaguaa    1680
uggggacuuu cuuuuguauc ugucuugaaa ggccaaaaua uuuuuauauu gcuguagaca    1740
aagccaccua uuuacaaaug gacucuuguu ccgucguuuc ccaccaggaa gaccguacua    1800 uguuugugc ucuauguauu cuggggucuu gaaacagguu ucaugggg auggccauuc    1860 acuagagccc agagggcag aaggggaagu gucacccug ccaaggggu cuggggaagg    1920 agggggggcua gucucagauu ugcuccuugu augucuaggg uaaacccugg gagaaucugg    1980
ugguaaaaga acauaugcug guuugcccc caucugcca uuugugugug uuucuggggcu    2040 acggguuuugc acacuuuggu gguuaacaug guggggaggaa guaagaaggg ccaagagggc    2100 acggugcuc uggguuuuccu gcugggaggc uguuucacug gugugguuua caucacauaa    2160
ugcauguuua gcuggguggag ugacaacagu augaaggac agagaaacaa auagguguag    2220
aaagagaguc acagagcaca cagucaccau ucugugccca ggcguucauu aaauguucaa    2280
uagaaugcug agcucugaua gacagagcgg gccauggaca cacugguauu gggucaucau    2340
ggaccuaagg aguuuuuuua auugaagaag gaaucuuaca uaacagaaga aagaauaaga    2400
agagcuguca aaacgagcuc ugagguuuuu gaagcccuu aauauaaaca gacagacaau    2460
ggcgugauca ggaaagggag aaaacaaaca aacaaacaaa caagaugcuu acagaaauac    2520
gagaggacgu gugagcaugc aaagagaacc cagcuagguu aguaucgggg ugcuggugga    2580
ucguuaaucc ugucggggua ccccagcucc aaggggauga gaggcagcaa gugagaggac    2640
acauaggaaa cuguaacaag acagaggcga gcagauggg agcuucagcg gaguguuaag    2700
cuaggcuucg caaucugacc acuuaacucu cccagcaaag aaaagaaagg cuuaaauacu    2760
aaaaagaagg aaagcuggaa gaaaggaugg uagaugugaa aggcauagag gauagaaagc    2820
aauagggagu ggagugcagg ugcuguggag agacgcuugc aggugacuca auucaccagc    2880
cugugcagcu gagaaagaca gccagugaca aaggagaaga agaaagguaa caauacacuc    2940
acaaauaggu agaugaaugu agcuggaaga cggggccugg cuagggacgg gaugagaggc    3000
ugugucagca gacugguuaa uucccaucug ugcuucugag auggacaaug acccaccga    3060 ccaagagacc uuucaggcau caauauguca gggagggcuu caugggggca auggaggcga    3120
ggcccauuaa uagcagauua ugauguaucc aauuaggugc accugcccuc uggaagugca    3180
gaaaccagua uugaaaugga aagaaagacu gaauggaagu ccgagaguac aaaugaaugg    3240
augggaaaaa agauuugcau ucgcucuuag ggggaggggug cugcugagcc ccagggucau    3300
cugaucuccc ggagaauaaa agggcgaggg agugauagag aguaacaaua agauggagaa    3360
gaaaugaaaa ggaguacaga gagaauaagu ggggacaaug aagucuagga gcgcggcuug    3420
uuuaacacaa gucauccaua uuaauucaaa auugaggccc ugggauggga uggcugugu    3480 ccaagggaug aagcuguugc cuagcaugug ccaaguucug gguuccaucu ccgccuggca    3540
agacaaacac aggaaacaaa auuauagccc agagguugua aauguuguuu uugaugguuu    3600
ugggacaaag agcuagaucg guuggaagau agagaaauag gaagaggugg gaaagaguua    3660
gaugagcaca gaggaagca gcaguucuua agauaagugu uuaaauaugg ugaaugcgua    3720
gcucuugggu gugucaagau gaaaauaacg aaaagaaaca aguuaggga ugacggcaca    3780 gggaugagcg gaagcggguga cuuuaguuaa ucaccguggc caacucaagc ccugucaggg    3840
```

```
auuuaaaaaa agguacaaag gcgauaaagg aagacacaug caauacggaa gagagagaca      3900
ggacagacag acacagcgaa aaggcugagg acaugccuga gagggucgcg aagggaugag      3960
agagagaaca gcgagaauuc ugcuuaauuc aaaaccgggc uccugagaua gcuaaauauc      4020
uccugagccc aaacaccagc acaggagauu aaauaacaaa agagcugcag gcagacccaa      4080
guggagaagg cuugggaccc ucagaucagg cuucaacuaa aucugugcac cugaggucca      4140
uaaauaaaag aauaaauauu gaaauaaagg agugacagaa aggaugaaug agcacacaug      4200
acugaauuag aaaaugggaau ggcuagagca gccaguaagg aguggcccau gggacuucug     4260
cucaucuuau ucugggcacc ugagguccu ucgugagaag augcagggag aagaggggaa       4320
gggaaaggca ugagagcaaa ugaagagag gcgaggagag gaaaugagaa aguggcagag       4380
aggggaagcg aucggugggu gccucggaag aggaaugucc acgaggauua auaacgaggc      4440
ucucauuaau ccuaaagauc gaugaggaua uccagaccca gguucuuaag gggaaggaga     4500
auggagagaa uuaaaaaaaa aagacgcaaa aaaaggagag aaagauaaua aaacaagcaa     4560
caugaugaau ggguaauuaa gagaggcugu cuggacagaa auaguaauga guucccaugc    4620
auaguccuua aauagauaaa uacauuauac cuuucaaaga augcgugaaa aaucgaagaa     4680
caccauggcc cccaaacaag gcugcaccuu ccauugcugu aauaaauac augcagcgga      4740
gagccauaaa uaacgaaaaa uacuuaaaug uaaaagguga ccagacagag ggagaagauu     4800
gcaagcccag auacacgagg gagggaggcg auguuugcuu ugcaugugua auacaauuau    4860
guucacagga aauuaauaga uuuaaaaaaa aaauccaaac uaagacuggg agaaaaaaca    4920
aggaagagag ggaagcgaga ucugagagau ggggcugaga cucccggggu aggcucagca    4980
ugguuuugac uauucugcac auccggacuu agaaaaguga guuugucagg gcaggaagag    5040
aaaggugaaa ucggagcgg gcagagcugg gcagauggau agaaaaggaa uggaaacuac     5100
acagguugug uguguggug gggggggaa guggggggcuc uaagaucuga gguuaggcuu    5160
guuuaaagcu gagccauugu uguccccaga ggaaucaaau cuuacugcuu uugugaagga   5220
agagaggaug gcaacgauau ugcaggaaaa gagggaaggg gguaggcaag gaggcaggga    5280
ggaacuuuca ugugcuauuc gcugacuggg auugguaaua gauagcucuu ggcccaccac    5340
aagcugcuuc cacacagccu aacugacugg gagcagcuau ggaucaccau ggccauguuu    5400
ugcuugcagg gggccauuuc acugucuguc acaucuucag uccauagaca cauucccugca   5460
cagugcccuu uccauagacg uggauaggag ggaagggcuc aggccugggg cuguggagau    5520
gauugcauga auagggggcg cuaugcccag ugggguaccuu gucuccucuc ugggaaagga   5580
ucucuucuga uccgauggg aaggggcuua gccagccaaa gggcagggau aggaggcuuu    5640
gucugcugcc ugcuggcuac caucuugagu gugacuuaca ccaggugcca gacaaaguga    5700
gcuugaccug gaagccuaga ggccaagag gcccgggugua agcaaguauc ucugagauca     5760
agccuacccu ucagcucaga gaguggaccc cugccuaggc ucccacacau gauccuaggu    5820
cccagauaug ccacccccugg agcccguuuc aaggcccauc uuccagaaug uuuaaaccug    5880
uguaguaac caguaaaaug ggaguuugua cuguguauug aaucugucuu cuuauuggcc     5940
ucugugggcu gcuggggggag accugagagag uuguuuauuc uaguguccccc cacccccugg   6000
gacucuuugc uuuugcccag uuuucuuucu cuguugugga uaagauuuug uagaguugug     6060
uguuguaugc uuguguuuga ccauuaaaaa aaaaaaaaaa gucacagccc uccuugauuu     6120
cucaauuccu auuggggggug cuaaauucca aaccaaacca auccaaaccca gauucauguc   6180
```

```
aagugcccaa caggaggaua auagcuuggc uggaucaagg gagcaugugc agacccaaga    6240
acagagugga cagaugggcu auaccgcaag ggggcuuuga gagcugagug caggcuaagu    6300
agagagaagg uauggaaggu uggggagggu ggggcugcug cuaccugagu ugcugagggu    6360
cugagacacc agcaaggagg aggggcccu ggaagaagcg uuuugagaug acugaagaug     6420
gaagaugggc gcucccuacg cuucuagcuu caagguuuuu aguguacgcc agccgccucc    6480
gaucguggaa gacacagccu aaccuuguca gaagccaccu ucugugcccc cagcaccacg    6540
ugucugggcc acgugagcaa cgccacgugg gccugacgug gagcuggggc cgcagggguc    6600
ugauggccuc cuguuucaga aucugggcg uuuaucaucc uugggacaac ugcugaccug     6660
gcuccggaag auuguccaca caagucgag ugacggagug agaugagggg gcggguggag     6720
augcucagaa gaaacagcc uuugcauggg guucauuucc agcuguuuag agagucagcc     6780
aaggugacaa ggugggguug gaugcggaga agaaugcugg gacuacaugu gggcuacagc    6840
ugugaaguca gugacaugggg gcagcaugg gaugggucuc uaggugggcc uugucucaac    6900
auucaugcca gaagauugga aggguacca ugggguacug ugggucagug ggaccuugga     6960
aggaacaagg gcuugggguag ugacuuugc caugucaccu ugggaucuag uguuuugag    7020
ucuuugacuc uuaaucugau cuugaauaac aaaugcucu aguucgggg uucgagagu      7080
cuguguagg auuccuagg auucgugugg ggagggcggu cugcaugugc ucccaaguug     7140
gugucccagc ccuucugccu gcucagggcu gucuuagaca uauuugcuuu ccuuucaac    7200
aucauaaaag aaggcaaauu uugucuuuug auugacacuc auaugcaaac cacaacaucc   7260
uuucucugau aauacuggga ccuacagcuc uccucggcuc cccccgcuau uugagcccac   7320
cuuugggggca gguaggccaa aggcccuggu guuuucugag gugaaguugu aauguaaag   7380
auguguaacu cagagcaggg ggaagaaaca cacccucaac ucugcuuccc cgugucccau   7440
cuuccuuucu gccuuccaaa uucuuaugaa caccguuuu uuuuuaaau uuuuuuccau     7500
uuaaugagca uccuuuuuuu uuuuuuaaaa gcuccauugg uggugcuuac uuuucuguug   7560
guguuuugug ucuguugcaa ugagcaucuu gcugccacg uuucguugc ccauggucu     7620
cucucaccug cuuagauucc auugaauggc uaugacauaa ugaucacccc aucuuacugu   7680
ugcugaugca ugaucaucuc cuguccuguu uuuuuuuuuu auuuuacauu accgaugaca   7740
ccauaacuaa uggcuuugca caaccagcuu ucccagcauc ccuagcgccc ccuacaucua   7800
gcucuuccca ugguuccuuu cuuuucuccu ugcuuccuuc ugcuagacug ugagcccacu   7860
cagggcaagg agcuugugga acugcgcucu guauuucuug uaggaugucu augaauguug   7920
acugcgugug ugugugugug uguguaugug uguguguguu ugugcgugug              7980
ugcgugugug cacgugugcg ugugugcgug ugugcaugug ugcgugugcg ugugugugug   8040
uguaagggug gacagguaug agugauggag ugauugaaag auuggcagac agaugagagg   8100
cuagaugaau ggaugaguga augaaugaau gaaugaguga gugaauuaau ggaugggau    8160
auucucuggu ugagcuucuu ggaugaaagg guaaugauug aauggcuguu gguugauuga   8220
agaaagccua caguauuuua ucuugucuga uaauguauua gcauuaagc ugauguauua   8280
guauuuaagg ugucugcuga cuuuccucac cucucguuu aaaaugcuu uugugugugu    8340
aaaacuuguu cuaauuacua augaaggcug aauacuuuuc acccauguuu guuaacaaau   8400
uguaucuuau cuucugugaa cuguuugucc aaguccagug gcucauggcu cuuucaggcu   8460
cuuguuugag ggguccuua gacuaggcaa uggccuuuca cagauaucua cagaugaug    8520
ugagaggcuc agcugacuuc uagcucggca uuagaauuua cuuacccugg gaaacaggga   8580
```

-continued

```
ggcugauauc uugcaccagc agguagaaaa cacuuuuagg cuugugucug gguucaccau   8640
gcauucuag cuugugagcc cugaccugug ucuguaccu cuuguggugu ggcaguccuc    8700
caccuugucc uccugaguga uagacuacau auaugccucu ccccuguucu ggggguguagu  8760
cucugaggcc augucuuaga ggaacuggcu ucuuagugcu cugucuagac auccccuuag   8820
cucuagucuu cccaugcacc ucaguggcag gugggucuu aauuuaggga augaaugaga   8880
aauucaguuc aggacugaug ugacccucag guuaguucca ggagcaaggc cauuuuaugg   8940
ucucggcucu ucccaaccuc cucacagggc aguuauagcc aucgggguag ggugugguguu  9000
ccgggagagc ucauccugcc auccagaacu ccccucccaca cucuauuaua gcacuuagcg  9060
ugucugccug uguucagccc ucucaccccca ugcuuaucug gacauugaag cuggaaagc   9120
caguggugac uucaacugac uuuuaauuca uccacccauc caucuggcua uccaucuagc   9180
caucugucag ucaauccauc cauccaucca uccaccauu cauccauccca uccaugcaua   9240
cacacauugg gccuccauca cuugaccugg ugcuuugggc cucucucccu uccugaaag   9300
caaaccccuu caccuugggc aagcugugug auaccauggg cuguggucau gaagcaaggc  9360
ccccauucac agccuccucc uccuccuccu aggucacggc ucugagcacg ucccagcugg   9420
accccuauca ccacagcuuu uucuccauaa ggcuucucac accucacacc cuccuccugu   9480
gauccaggag ggccagauuc ccagagagcc cuggggcugg cccuucccac cauccgcgga   9540
gcugccuccc caggcuucac acugccuggu gcauggcccc ugcaugagc uuggccuuca    9600
ccuuugcagc uuccuccacc agauggcagu gguugacu cgugugccca uccuucgca     9660
ccuucauuca uucauucucu uacagccagc aagcaucucu uuaaaaaaa aaaauuagc    9720
uagugcuaua cuagagccgg cucacaagca cccauugcac cacugguccuu ugaaagaaaa  9780
gaugggaca uuuguaaaga agcuguguuu gugguggccaa uaagaggagc ccuugauuu    9840
caauucaaac uucaggucug aguucuauug ccagcuugau ugcucucucc aauuuuguuc   9900
cucacaaaac uagguugauu aguaaucagc aaacugucuu cccgggggc ucagaaauca   9960
uagcccagau ccuuaagagg cccaaauggg gagugggacua agcacgaagc agcugccucu 10020
ggcugcgagc aggcuuucaa ggcugugaga cacucuguuc uucuaugagg augaucugag 10080
agccguucug gccacuuugg agcucagcua augcuuggcu ccuuuuuaga gaaaauugca 10140
ggagauggau gcucguacaa gugacaagga ucaugccca auguccuuuc ugaauaaucc 10200
auucgcagac ccaggcgagc aaggcacaug gcacuuugca aaccccugug uguucagga   10260
ggacccaugc uaggggaggc cuccuuucag cuuucucgcu ugaaggggaa gagacgcagg 10320
gcucuucuga guucuccucc cacuagacgc aguaggggcg gcaaggccag aaccuggagc 10380
uggacaaaau guguaugga ucuugccuca gggcuguugu gaggauugguu auaacuggac 10440
acuucugacu gugacccuaa aaggcagugu auguguccccu ggggguguge cagagcauug 10500
gaaaccuag cccuggagug ggggugguccu ugcuuggggua uaaugggaa acuuuguau   10560
cuguuaaauu uguauauuuu ccuauagaga cuuuaacacc acgggauagg ggacucuuua 10620
gauaguaccu gugcccuccg ccccccucgg acacauccac accuaccucu aggagagguu 10680
ggggguugucu uuagcucucu gacugaggac caagccucug acucagaacu guauauggca 10740
ccuaguuaca ucccuuuucca aaaggcucuu cccaggggag cacucggccc gaucuggcag 10800
accccauugu cccuuuccca augcccucuc ucccacuaac agcaucaggc caaacugccu 10860
gagaucuggu gccuaccaca gugccuggcc aggggguaggg cuucagugac cuucuguugu 10920
```

```
auuuguguag guagaugagu agcuaacaau uguaacaggu ccuagggcca gaugcguaug    10980
gucucauuca gugguuugua auggagaaug uaucugaacc cauaucaagc caucucucuu    11040
ccuuaacaug uuaagcagcc acugcugucc uggguuguuu ugcaccuugc cuuguugucu    11100
uucaugcuaa guaaaaaaaa guccugcuuu cugcugagag ucuguuucuu cuggaacuca    11160
ccuaggugug aucuggcagg gcugcuaagc ugugucucug ccccucugac ccguagucuu    11220
cuucucucuc aggugugcgu cacuggcaag ccuaccucac aggguuguug ugagggcuaa    11280
gggcugaucg gcuguaacag ugugaugucc augcuggcug ucaccaggga uggugccaug    11340
auggggguugg cuugaaauca caaccuauac cguuauuagu ggucacugaa uaaagagucu    11400
cacuguggac acugagguug uauauccagc cgucgaugug guauucgagg cuggcugugu    11460
gguccuggcu aaaucgguggu ugguucauuc augcauguua gcgucuaagu cccucucugg    11520
ugcccuggcc uucccuuccu uuccaucaug guggcuggug cugcugguug ugugaaggcc    11580
aaagcuggcu gggccacuau gcuuggggc auuaggaggg guggugucug uugguagaug    11640
cuucuucaag cuuguguuuc uguguaugug gugugugcau aucugcccc ugggacagug    11700
ccaagaacca agggucaaua gaggggcuuc caaauuauga cauccuugaa uuuuucuua    11760
cugcucucuc acuuuuagcu gguaggucug gguggcuguu cuccuccccg cuccccuuu    11820
cuucccugc caggagauga gaaaaauuag cuuucuacc accaaauucu gcuuuggacu    11880
gagcuuaggu uuacacacuu uacguugucu cucagcaugg ucccauucua uggauggca    11940
gacugagaac cagggacaau agucauguua ugugugaaua acucuuucca cuccaccaaa    12000
uaaaaccuca gcaagcccag ugucuuaggc ucaccccugc cugauccugg caugcacuca    12060
gaauggucuc ccuucugcuu ugucccac cuaccaccuu guauuuccu ggcagggua    12120
ggcauggagg gaggagcaag gaggcugugu ccucccaggu cucccaguce cggagugucc    12180
caguccaugu cugucugaga uucacauuuc ccacgaggcu cuuccauga uguuggauuc    12240
cauccccagu cccgucccug ugaaucuggg cgagcagccu uccacuuuuc cacucuuguu    12300
ccaagccccac gccaagaagc cccccccaccc acugcacaga agcccagccu ccgcucaguu    12360
ccuuguguua cucucggcuuu caaagcccug gucucagc ccuagaugcu cuuaaacccu    12420
uggugugc acugugluccu cgggcucagg accccgugu ucauguuc ccucuggcug    12480
ccaugucuuu cccaucaua cuccauuacc aaaaucccga cucugccucc ucaggcugu    12540
gucugugacu gcuacaguuc auccugucuu ugacaacuuc uuggaaccuu ugcuucugug    12600
cucugggguc uuguggguagg cacauguggg ucaggucauu ugcucaggua auuuugacuc    12660
uguggcuagg ugccuggucu cagaaugggcc uuuggcccccu ugugggccag guuuuggu    12720
gacucuuagg uagcuuaugu cucuggaag uaaagaaag gaagccaggg gccuggcaaa    12780
aagggaaugc uuagauugug acuaagcucu aggcuugcuc caacucaaug ucacccugcc    12840
ucuugaagua gugggcaccu aauacuugcu ccaugaugaa guaggggaag cuaagugaau    12900
guggauaggc gggugacuag gaggucuuua aggacuuuc ccaggaucua gucagcuaca    12960
ggacaccccuu ccuguagaa acacugcuu ggagauauua uguccagaau aaaacuuucu    13020
gagagcuaaaa aguccucau ugacauuug accugaguga uccugaaaag gaguguuug    13080
gcaguuccca aauucuaagg uggacuuggc ugugcccaua ucaucaccga ggcccucuc    13140
ucggggugaa aggagauuau uucgccccca aagcccuugu ucccaccauu ggugacaauc    13200
agcacugacu uagaaguuac cuggugagauu ugggguacagc ucaaggcacc uggcagacug    13260
ggggagauugg accccuugaa uucuucuuuu cuacagagug cuccguaggc acaugggugg    13320
```

| | | | |
|---|---|---|---|
| gggaggggu | cccaggguccu | uacccauuug | ggcaucagac | cuguuuugu | uuuuguuu | 13380 |
| ucuuccaacu | gaaccuugag | cagcuugccu | gaaucauccc | cagccuuagu | uucucuuccu | 13440 |
| guacaaaggg | ugucauuagu | gacugcccau | cauauggugg | cucaugagaa | ucaaggucug | 13500 |
| aguucugguc | auccuugucc | cuuguggaac | guguggugc | cuuggcuguu | ugccauaucc | 13560 |
| uagaaauagu | caaaccaacc | ugguuugauu | ggggauuca | gugagguuu | uuugugugu | 13620 |
| gugugaaaac | gaguguuuug | uugcuuggua | ugcaggugcu | caugucugcu | aacccauacu | 13680 |
| gacuguugug | gaggugggcc | cugggauacag | auguaccuua | guuucugaaa | cuucaguugucc | 13740 |
| augugagacu | cggacagagu | ggagggcagg | agggauagcac | cuacccagcu | cuggagcgac | 13800 |
| auagaaagcc | uugcuuucaa | auguuaggau | ucagcaguuu | ugauggggagg | cucugagaua | 13860 |
| caagaccagg | aagacuauua | agaacacccc | ucuaggaggg | caaggccaaa | gucuuuggaa | 13920 |
| aaccaccaag | guuuaauaga | cugugaauug | gcuagaaguc | uggggggugg | uaugagaaag | 13980 |
| auggaaaauc | cuagaauagg | uuuuuauuua | uggaaaagu | caggagcugg | uguguaggug | 14040 |
| uugccccacc | cccauggcug | uccagaaguu | gggccuucua | cauagcucag | gcuuucugag | 14100 |
| cacagggcug | gguugccccc | uccaguuccu | acccugccua | gugcaugaaa | acucuuuauc | 14160 |
| ugccaugggg | augggagca | gauggcuuca | ucugcagcug | ugucucucuc | agccucuaca | 14220 |
| gccacgggga | cgccuugcac | auuuccugug | ggacaugcug | gacccaagac | ucuggacccu | 14280 |
| ggccuccccu | ugaguagaga | gacccaccua | cugacugaug | aacugcgcug | acccugggu | 14340 |
| caggcaugug | gccuugaucc | cuacccaugg | acccugagac | uugggggggu | gggagaaagg | 14400 |
| cuguugugc | uucacuguug | agcuacauc | ugugaaaugg | gcucagguuc | cuaccucaca | 14460 |
| gggcuguugu | gaggcagccg | caauguguguu | agaagcaugg | ggccuagugg | cucauggugc | 14520 |
| uuucaauaaa | uuucuuguuu | uaacuaaa | | | | 14548 |

<210> SEQ ID NO 3
<211> LENGTH: 5971
<212> TYPE: DNA
<213> ORGANISM: Mus musculus
<220> FEATURE:
<223> OTHER INFORMATION: Mouse Meg3 isoform 3 (ENSMUST00000143272)

<400> SEQUENCE: 3

| | | | | |
|---|---|---|---|---|---|
| gacuuuuggu | aaaucaccuu | uugccguuuc | cuuugucccc | gugaagcccc | cccuggccgc | 60 |
| cccccuccuca | uucugggcug | gcuggcugag | gggggggca | gccugaggggc | ugcgacgugg | 120 |
| cagguuucua | gaauguucua | uugauggccg | caagagggcg | cugguggcac | ugcggaauuu | 180 |
| uggggggcgg | ggugggagg | gaagaggagg | uggccuuugu | ucuccugcag | gaggggucg | 240 |
| ggagcgagau | ggguugcggg | accauggguu | cauuuaccua | uggggaaaug | uuagugaua | 300 |
| ccuggauuca | cuaaggugcg | cuugcaggac | uuacaauagg | ucagagaugg | cgucaucugc | 360 |
| aguggcugug | ugauuuaggg | ugucauggac | gcagauuaau | uuauuucag | ugauuugugu | 420 |
| uuucuggggu | cuuagaaagg | ugugcuuuu | ugaggaagaa | uugcaaaaaa | uauuaauuaa | 480 |
| uuaggcguca | uccauaaggg | ucuugagagu | ugacgugggca | aaggggggc | aagguuuuga | 540 |
| ggagaagggu | guuaauuggg | uggggggagg | caggugguc | ugccuuuauu | uugcauaua | 600 |
| gcugaagacc | ucaaaaauga | guguucugua | uuaagaauug | agucuuuaaa | uuuuaauuau | 660 |
| gcuuaauugg | auuuacuaau | gguggggg | ggcagcgucc | ugcuuuacu | uaucaggagu | 720 |
| agaauugugg | ucuggggggca | gccccuuacu | gcagggucuc | uuuggugcaa | ggcggcuccu | 780 |

-continued

```
ggaugccugu gugugugcug cgucaugucu ggaaaauggc ucaggcagag gcgauggggg      840
ugcauagcga cccuuaaaga uggcugaugu gggcucugcc ccccccccc aagccugaaa       900 ccuguuggc gcccucccc cuccuacguc agcuagcuc uagcagcugc guccuggcgc         960 cuguggggu gccucaggug guugggcuau uggagucuua gugagugcgg gccgcgcgcc      1020
cccuagcggu cucuaugugc aaauggucu uggccugcca gacuagcgcu agaguugcgc     1080
augcgcacac agcuaacacu ugugaccugu caaucaauuc aucuguaccc cucccauugc    1140
uguccucccc ucccauuucu ccuccuacuu cucuccccau ucuacuuuc ccucuuccc      1200 cucccauuuc uguuucccu ccucccccu cccauuucuu cucccuccuc ccccucccau      1260
uucuucuccc uccuccccu cccauuucuc cucccucu uccccuccc acuuucucc         1320 ccuaucuucc cccucccauu uuccucacu ucuccucc ucccacuucu ccucccuccu       1380
cccuccuccu uucucccccc cacccacuuc cccauuccu cuuaccccuc ccuccuccu      1440 ccuuucuccu cccgcccua cccauuuccc ucauucucu acccccuccc uucucuccu       1500 ucccuccacc ccauccugc uucucuuccc ugaucccuc caccccuccc ucuuucccc       1560 caagccuucc ccuccuucu cuccucuuc acuugccccc ucccucucua ugcuguuccu      1620
gggcuggccg uuagaggucu ucaagguggu uucuaacaac ccccucccau auccuaggcu    1680
cucucuucag ggaugacauc aucggcucac accagucuuc caggaccacc uucuggaugc    1740
caaggcugcu gcucgaguac cugcugugca ccuuaccuc cugagccaag gagcacggau     1800
uccaggaacc cacuaccaua cagagcaacu ccuuguggac ccccuggga ucaggacagc     1860 gagggacaag cgacaaagag gaucaucagu ggccagcuag uuucucuggg guucaaaccu   1920
ugaaccagug cccuagugag ggggcacugg ccauggcccu ugaccuuugc ucugcuugug    1980 ucuugaguc gagcccuuc cuguacaucu gucucugu caucugcua ugaacugga          2040 gugcugcccu ccccgaggag ggucgucccu ugugacugau caugcugucc uaacaaugc     2100 cugagcaaaa gggucccuuu gggaaccucu caggagggg acccgggucu ggggcgacca    2160
gcaucuugcu ggcaacuccg uggguggu gggguggu gcuuccuucu ggaaugagca       2220
cguggcugac cccccaaggc augucccuc ccccuccucc acccaccuuc ucggagaugu    2280
cccuuuuggg guagugggga cauuaggagc aaccuccuag gguuguugug agaauuaaau   2340
gaacugcagc agcccgaggc agggcugggc agagaccuca gcacauguuu guugaaggu    2400 uugcaggugg aucuaguccu cccguucaug gcucaugugu ucaaccauu cucucgcaga    2460 cuccugcagc cccuaugccc agggcucucc uugcgccagc cccggcuucu cgaggccugu   2520
cuacacucgc ugcuuuccuu cccuccacuccc aauuuccccu ccaaccacu gcuuccugac  2580 ucgcucuucu ccaucgaacg gcucucgcuc aggccgucg cgucuuccug ugccauuugc    2640
uguugugcuc agguuccacg agcugcccau cccacagaa gagcagcugg cauugcccac    2700
cggccaugcc ggcugaagaa aagaagacug aggacccag gaugcccagc gcgaggaccc    2760
caggaagccc agcgcgagga cuccaccac gacgcccagc gcgaggacuu cacgcacaac    2820
acguugcaac ccuccuggau uaggccaaag ccaucaucug gaauccugcg ugggacccug   2880
gacacacgga cacagacacc ugcccccagg acccuccaac uguaaaucga uuggaagcgc    2940
ccuugugagc uggggccuuc aaagggcuga ggagaaaaug caggccgaga gaccagcuuc   3000
ucaaauaggc uucaagccuc caugaccuga gcucaccccc uggaaaugu uggaaaacau    3060 aaugggcagu uuucugcucu ucaagucuuc caucaaaacc ucuucaaguu cuuuauuguu   3120
uaggacugag acacuugggg acaguaaugg ggacuuucuu uuguaucugu cuugaaaggc   3180
```

```
caaaauauuu uuauauugcu guagacaaag ccaccuauuu acaauggac ucuuguuccg    3240 ucguuuccca ccaggaagac cguacuaugu uuguguucuc auguauucug gggucuugaa    3300
acagguuucu caugggaug gccauucacu agagcccaga ggggcagaag gggaaguguc    3360
uacccugcca aggggucug gggaaggagg ggggcuaguc ucagauuugc uccuuguaug    3420 ucuagggua acccugggag aaucggugg uaaaagaaca uaugcugugu ugccccaca     3480 ucugccauuu guguguuu cugggcuacg gguuugcaca cuuugguggu uaacauggug    3540
ggaggaagua agaagggcca agagggcacg ggugcucugg uuuuccugcu gggaggcugu    3600
uucacuggug uguguuacau cacauaaugc auguuuagcu gggugaguga caacaguaug    3660
aagggacaga gaaacaaaua ggguagaaaa gagagucaca gagcacacag ucaccauucu    3720
gugcccaggc guucauuaaa uguucaauag aaugcugagc ucugauggac agagcgggcc    3780
auggacacac ugguauuggg ucaucaugga ccuaaggagu uuuuuaauu gaagaaggaa    3840 ucuuacauaa cagaagaaag aauaagaaga gcgucaaaa cgagcucuga gguuuugaa    3900 gccccuuaau auaaacagac agacaaugc gugaucagga aagggagaaa acaaacaaac    3960
aaacaaacaa gaugcuuaca gaaauacgag aggacgugug agcaugcaaa gagaaccccag   4020 cugguuagu aucggggugc ugguggaucg uuaauccugu cuggguaccc cagcuccaag    4080
gggaugagag gcagcaagug agaggacaca uaggaaacug uaacaagaca gaggcgagca   4140
gauggggagc uucagcgaga uguuaagcua ggcuucgcaa ucugaccacu uaacucuccc    4200
agcaaagaaa agaaaggcuu aaauacuaaa aagaaggaa gcuggaagaa aggaugguag    4260
augugaaagg cauagaggau agaaagcaau agggagugga gugcaggugc ugggagaga    4320 cgcuugcagg ugacucaauu caccagccug ugcagcugag aaagacagcc agugacaaag    4380
gagaagaaga aagguaacaa uacacucaca aauagguaga ugaaauguagc uggaagacgg    4440 ggccuggcua gggacgggau gagaggcugu gucagcagac ugguuaauuc ccaucugugc    4500
uucugagaug gacaaugacc cacccgacca agagaccuuu caggcaucaa uauugucaggg   4560 agggcuucaa uggggcaaug gaggcgaggc ccauuaauag cagauuauga uguauccaau    4620
uaggugcacc ugcccucugg aagugcagaa accaguauug aaauggaaag aaagacugaa    4680
uggaagcucg agaguacaaa ugaauggaug ggaaaaaaga uuugcauucg cucuuagggg    4740
gagggugcug cugagccca gggucaucug aucucccgga gaauaaaagg gcgagggagu    4800
gauagagagu aacaauaaga uggagaagaa augaaaagga guacagagag aauaaguggg    4860
gacaaugaag ucuaggagcg cggcuuguuu aacacaaguc auccauauua auucaaaauu    4920
gaggcccugg gaugggaugg gcugugucca agggaugaag cuguugccua gcaugugcca    4980
aguucugggu uccaucuccg ccuggcaaga caaacacagg aaacaaaauu auagcccaga    5040
gguuguaaau guuguuuug auggguuugg gacaaagagc uagaucgguu ggaagauaga    5100
gaaauaggaa gaggugggaa agaguuugau gagcacaaga ggaagcagca guucuuaaga    5160
uaaguguuua aauauggugga augcguagcu cuuggguguug ucaagaugaa aauaacgaaa    5220
agaaacaagu uuagggauga cggcacaggg augagcggaa gcggugacuu uaguuaauca    5280
ccguggccaa cucaagcccu gucagggauu uaaaaaagg uacaaaggcg auaaaggaag    5340
acacaugcaa uacggaagag agagacagga cagacagaca cagcgaaaag gcugaggaca    5400
ugccugagag ggucgcgaag gaugagaga gagaacagcg agaauucugc uuaauucaaa    5460
accgggcucc ugagauagcu aaauaucccc ugagcccaaa caccagcaca ggagauuaaa    5520
```

| | |
|---|---|
| uaacaaaaga gcugcaggca gacccaagug gagaaggcuu gggacccuca gaucaggcuu | 5580 |
| caacuaaauc ugugcaccug agguccauaa auaaaagaau aaauauugaa auaaaggagu | 5640 |
| gacagaaagg augaaugagc acacaugacu gaauuagaaa uggaaauggc uagagcagcc | 5700 |
| aguaaggagu ggcccauggg acuucugcuc aucuuauucu gggcaccuga gucccuucg | 5760 |
| ugagaagaug cagggagaag aggggaaggg aaaggcauga gagcaaauga aagagaggcg | 5820 |
| aggagaggaa augagaaagu ggcagagagg ggaagcgauc gguggugcc ucggaagagg | 5880 |
| aauguccacg aggauuaaua acgaggcucu cauuaauccu aaagaucgau gagguaaucc | 5940 |
| agacccaggu ucuuaagggg aaggagaaug g | 5971 |

<210> SEQ ID NO 4
<211> LENGTH: 1988
<212> TYPE: DNA
<213> ORGANISM: Mus musculus
<220> FEATURE:
<223> OTHER INFORMATION: Mouse Meg3 isoform 4 (ENSMUST00000124106)

<400> SEQUENCE: 4

| | |
|---|---|
| cgaagagcug gaauagagcu cgccucggcu cugcuggccu uggcugcagc ucuuccagaa | 60 |
| acccggggcg cccacagaag aaucucuuac cuggcucucu cuucagggau gacaucaucg | 120 |
| gcucacacca gucuuccagg accaccuucu ggaugccaag gcugcugcuc gaguaccugc | 180 |
| ugugcaccuc uaccuccuga gccaaggagc acggauucca ggaacccacu accauacaga | 240 |
| gcaacuccuu guggaccccc cugggaucag gacagcgagg gacaagcgac aaagaggauc | 300 |
| aucaguggcc agcuaguuuc ucgggguuc aaaccuugaa ccagugcccu agugagggg | 360 |
| cacuggccau ggcccuugac cuuugcucug cuuguguguu gagucugagc ccuuccugu | 420 |
| acaucugugc ucguguucau cugcuaguga acuggaguugc ugcccucccc gaggaggguc | 480 |
| gucccuugug acugaucaug cuguccuaac aauguccuga gcaaaagggu cccuuuggga | 540 |
| accucucagg aggggacccc gggucagggg cgaccagcau cuugcuggca acuccgugggg | 600 |
| uggggugggg uggggugcuu ccuucggaa ugagcacgug gcugacccc caaggcaugu | 660 |
| ccccucccc uccuccaccc accuucucgg agaugcccu uuuggggguag uggggacauu | 720 |
| aggagcaacc uccuagggu guugugagaa uuaaaugaac ugcagcagcc ugaggcaggg | 780 |
| cugggcagag accucagcac auguuuguug aaagguuugc agguggaucu aguccucccg | 840 |
| uucauggcuc auguguccuca accauucucu cgcagacucc ugcagcccu augcccaggg | 900 |
| cucuccuugc gccagaggua gguggggaaag agaacuggga gagccggac ucacucauga | 960 |
| gauugaacuu aaauucacac ggaggacacu uggacucuug ccacauuagc cccggcuucu | 1020 |
| cgaggccugu cuacacucgc ugcuuuccuu ccucaccucc aauuucccu ccaacccacu | 1080 |
| gcuuccugac ucgcucuucu ccaucgaacg gcucucgcuc aggccugucg cgucuuccug | 1140 |
| ugccauuugc uguugugcuc agguccacg agcugcccau cuccacagaa gagcagcugg | 1200 |
| cauugcccac cggccaugcc ggcugaagaa aagaagacu aggaccccag gaugcccagc | 1260 |
| gcgaggaccc caggaagccc agcgcgagga cuccacccac gacgccagc gcgaggacuu | 1320 |
| cacgcacaac acguugcaac ccuccuggau uaggccaaag ccaucaucug gaauccugcg | 1380 |
| ugggacccug gacacacgga cacagacacc ugccccagg acccuccaac uguaaaucga | 1440 |
| uuggaagcgc ccuugugagc ugggccuuc aaagggcuga ggagaaaaug caggccgaga | 1500 |
| gaccagcuuc ucaaauaggc uucaagccuc caugaccuga gcucacccc uggaaauguc | 1560 |
| uggaaaacau aaugggcagg uuuucugucu ucaaaguuuc caucaaaacc ucuucaaguu | 1620 |

| | | |
|---|---|---|
| cuuuauuguu uaggacugag acacuugggg acaguaaugg ggacuuucuu uuguaucugu | 1680 |
| cuugaaaggc caaaauauuu uuauauugcu guagacaaag ccaccauuuu acaaauggac | 1740 |
| ucuuguuccg ucguuuccca ccaggaagac cguacuaugu uuguguucu auguauucug | 1800 |
| gggucuugaa acagguuucu caugggaug gccauucacu agagcccaga ggggcagaag | 1860 |
| gggaaguguc uacccugcca agggggucug ggaaggagg ggggcuaguc ucagauuugc | 1920 |
| uccuuguaug ucuagggaau acccugggag aaucggugg uaaagaaaca uaugcugugu | 1980 |
| uugcccca | 1988 |

<210> SEQ ID NO 5
<211> LENGTH: 797
<212> TYPE: DNA
<213> ORGANISM: Mus musculus
<220> FEATURE:
<223> OTHER INFORMATION: Mouse Meg3 isoform 5 (ENSMUST00000166636)

<400> SEQUENCE: 5

| | | |
|---|---|---|
| uccuuccucg ccacuccagu gucugucuuu ccuucacagc cccggcuucu cgaggccugu | 60 |
| cuacacucgc ugcuuuccuu ccucaccucc aauuucccu ccaacccacu gcuuccugac | 120 |
| ucgcucuucu ccaucgaacg gcucucgcuc aggccugucg cgucuuccug ugccauuugc | 180 |
| uguugugcuc agguuccacg agcugcccau cuccacagaa gagcagcugg cauugcccac | 240 |
| cggccaugcc ggcugaagaa aagaagacug aggaccccag gaugcccagc gcgaggaccc | 300 |
| caggaagccc agcgcgagga cuccaccac gacgcccagc gcgaggacuu cacgcacaac | 360 |
| acguugcaac ccuccuggau uaggccaaag ccaucaucug gaauccugcg ugggacccug | 420 |
| gacacacgga cacagacacc ugccccccagg acccuccaac uguaaauccc ucuacagcca | 480 |
| cggggacgcc uugcacauuu ccuguggggac augcuggacc caagacucug gacccuggcc | 540 |
| uccccuugag uagagagacc caccuacuga cugaugaacu cgcgcugacc uggggucagg | 600 |
| caugguggccu ugaucccuac ccauggaccc ugagacuugg gggggguggga gaaaggcugu | 660 |
| ugugucuuca cuguugaguc uacaucugug aaauggcuc agguuccuac cucacagggc | 720 |
| uguugugagg cagccgcaau gugcuuagaa gcauggggcc uaguggcuca uggugcuuuc | 780 |
| aauaaauuuc uuguuuu | 797 |

<210> SEQ ID NO 6
<211> LENGTH: 755
<212> TYPE: DNA
<213> ORGANISM: Mus musculus
<220> FEATURE:
<223> OTHER INFORMATION: Mouse Meg3 isoform 6 (ENSMUST00000126289)

<400> SEQUENCE: 6

| | | |
|---|---|---|
| uccuccaccc accuucucgg agaugcccu uuuggggguag uggggacauu aggagcaacc | 60 |
| uccuaggguu guugugagaa uuaaaugaac ugcagcagcc ugaggcaggg cugggcagag | 120 |
| accucagcac auguuuguug aaaggauuugc agguggaucu aguccucccg uucauggcuc | 180 |
| auguguccuca accauucucu cgcagacucc ugcagccccu augcccaggg cucuccuugc | 240 |
| gccagccccg gcuucucgag gccgucuac acucgcugcu uccuccuc accuccaauu | 300 |
| uccccuccaa cccacugcuu ccugacucgc ucuuuccau cgaacggcuc ucgcucaggu | 360 |
| uuaaggcuug gcuugcuggc ccuggagauc ccgucgccgu cuucgucgaa ucgaaauucc | 420 |
| uagccaucgu ccuucccugg ccugucgcgu cuuccugugc cauuugcugu ugugcucagg | 480 |

| | |
|---|---|
| uuccacgagc ugcccaucuc cacagaagag cagcuggcau ugcccaccgg ccaugccggc | 540 |
| ugaagaaaag aagacugagg accccaggau gcccagcgcg aggacccag gaagcccagc | 600 |
| gcgaggacuc cacccacgac gcccagcgcg aggacuucac gcacaacacg uugcaacccu | 660 |
| ccuggauuag gccaaagcca ucaucuggaa uccugcgugg gacccuggac acacggacac | 720 |
| agacaccugc ccccaggacc cuccaacugu aaauc | 755 |

<210> SEQ ID NO 7
<211> LENGTH: 706
<212> TYPE: DNA
<213> ORGANISM: Mus musculus
<220> FEATURE:
<223> OTHER INFORMATION: Mouse Meg3 isoform 7 (ENSMUST00000143847)

<400> SEQUENCE: 7

| | |
|---|---|
| gccugucuac acucgcugcu uuccuuccuc accuccaauu uccccuccaa cccacugcuu | 60 |
| ccugacucgc ucuucuccau cgaacggcuc ucgcucaggu uccacagcu gcccaucucc | 120 |
| acagaagagc agcuggcauu gcccaccggc caugccggcg aagaaaaga agacugagga | 180 |
| ccccaggaug cccagcgcga ggacccagg aagcccagcg cgaggacucc acccacgacg | 240 |
| cccagcgcga ggacuucacg cacaacacgu gcaacccuc cuggauuagg ccaaagccau | 300 |
| caucuggaau ccugcguggg acccuggaca cacggacaca gacaccugcc ccaggaccc | 360 |
| uccaacugua aacccucua cagccacggg gacgccuugc acauuccug ugggacaugc | 420 |
| uggacccaag acucuggacc cuggccuccc cuugaguaga gagacccacc uacugacuga | 480 |
| ugaacugcgc ugacccuggg gucaggcaug uggccuugau cccuacccau ggacccugag | 540 |
| acuuggggg gugggagaaa ggcuguugug ucuucacugu ugagucuaca ucugugaaau | 600 |
| gggcucaggu uccuaccuca caggggcuguu gugaggcagc cgcaaugugc uuagaagcau | 660 |
| ggggccuagu ggcucauggu gcuuucaaua aauuucuugu uuuaac | 706 |

<210> SEQ ID NO 8
<211> LENGTH: 113
<212> TYPE: DNA
<213> ORGANISM: Mus musculus
<220> FEATURE:
<223> OTHER INFORMATION: Core sequence of mouse Meg3

<400> SEQUENCE: 8

| | |
|---|---|
| ccccggcuuc ucgaggccug ucuacacucg cugcuuuccu uccuccaccuc caauuucccc | 60 |
| uccaacccac ugcuuccuga cucgcucuuc uccaucgaac ggcucucgcu cag | 113 |

<210> SEQ ID NO 9
<211> LENGTH: 6984
<212> TYPE: DNA
<213> ORGANISM: Homo sapiens
<220> FEATURE:
<223> OTHER INFORMATION: Human Meg3 isoform 1 (ENSU00000522771)

<400> SEQUENCE: 9

| | |
|---|---|
| cagacggcgg agagcagaga gggagcgcgc cuuggcucgc uggccuuggc ggcggcuccu | 60 |
| caggagagcu gggcgccca cgagaggauc ccuacccgg gucucccuc agggaugaca | 120 |
| ucauccgucc accuccuugu cuucaaggac caccuccucu ccaugcugag cugcugccaa | 180 |
| ggggccugcu gccaucuac accucacgag ggcacuagga gcacgguuuc cuggauccca | 240 |
| ccaacauaca aagcagccac ucacugaccc ccaggaccag gauggcaaag gaugaagagg | 300 |
| accggaacug accagccagc ugucccucuu accuaaagac uuaaaccaau gcccuaguga | 360 |

```
gggggcauug ggcauuaagc ccugaccuuu gcuaugcuca uacuuugacu cuaugaguac    420
uuuccuauaa gucuuugcuu guguucaccu gcuagcaaac uggaguguuu cccuccccaa    480 gggggguguca gucuuugucg acugacucug ucaucacccu uaugaugucc ugaauggaag   540
gaucccuuug ggaaauucuc aggagggggga ccugggccaa gggcuuggcc agcauccugc   600
uggcaacucc aaggcccugg gugggcuucu ggaaugagca ugcuacugaa ucaccaaagg    660
cacgcccgac cucucugaag aucuuccuau ccuuuucugg gggaauggggg cgaugagag    720 caaccuccua ggguuguugu gagaauuaaa ugagauaaaa gaggccucag gcaggaucug    780
gcauagagga ggugaucagc aaauguuugu ugaaaagguu ugacagguca gucccuuccc    840
accccucuug cuugucuuac uugucuuauu auuucccaa cagcacucca ggcagcccuu     900
guccacgggc ucuccuugca ucagguaggg gcuuugcaga gaccaucgac gggcugacuu    960
gaguaagaac acgaauuaug cauguggcca uuccagagc acuuucuaug ugauaugaac    1020
augugauuuu uauguaauau guguauguaa acgaggcagc ucauuucca ggugaggaug    1080 cauuugguag uguugauuuu uguaauuuaa agaagcugaa agggagagag gacccgugag   1140
gacugaacuc ucugucccau gggguagggc uuacauuuac auuaaagaaa cagaaacuug   1200
cugggaggug uaaguauuug gucacauugc uggcaacaga aggguugga guuggaccca    1260 ggguggccacg cuagcugccc ucaccccuuc uuccccucug gcccagaguu auacuaagag  1320
uccuuuuauu ucaaaccaaa uguuugacaa ugggacaguc uguuugaaau cccagcugcc   1380
uggggugguc uugggggucu gguggccccc agugcuggua ccaugugcug gcuucaccuu   1440
uuaauaacag ugugaccuua aacaagucgc uuaacuacuc uaaguuucag uuucuuucau    1500
ggucuaaaug gagauuaaaa cacacacaca cacacacaca cacacacaca cacacacacc    1560
cccucgugua ucuaccccac agggcgcuuu ugaagaccaa augcuguaac uacuaugaaa   1620
gugcuuugua aauugcugug gaaagugugaa gcuacaag cacccgaggc ugucccuccu    1680
ugcucacaug uccagcccaa uucucccuua gugagaacag cacucaguag gugcugugug   1740 uguuugugu caauuaagaa auccagaau aaauaaaaau gaauuaauuc aacaaacauu     1800 uucggggca ccgacaaucu gcccagugca ccaggcuagg uaucugauac aaagauaaug   1860
aaaacagucu cuuggaaccu aauuggggguc ucauuugac caggaauuuc uuucgucccg    1920
uuuuaagcca accaguuuug uccggacaag acaaaaacaa cuuggggcugc uuuagagaag  1980 cccagcucag guuagacaau agcugcccag ccucugaaag gggcugauug gauuauguugg  2040 caaauggagg ugcaaggaug acuuggacgg ugacaaauga aguggggcgga gaccugcuuu  2100 gaguuaauucc aggcuauuag gaggggaaccu uuugucuucc agagacuggc aggagcuuuu  2160
accagugguu uuuacauccu uaauguucag gacgaauaau uuauggucag ugaaauccaa    2220
ggccccagug agauucgagu gggcuguaaa aucgagaguc cugcucccag ugaguaaugg    2280 uaguaaugu uucugucacu uuuugcaacc guccauucau uugauccuca caacucccug    2340
uccugagcca ggaccggcca cugccacucc cagggaaaca gaggcugguca agaggcucca   2400 cagauuggc cccacuggau cauugaaccc cuguucccug aguucuagag gaagaauugu    2460
accugucuca guccggcca ccucagaaag gccucccucu gcauucuga cuuugcgug     2520 ccggcagccu ggagccuccc aggucccugc ugucaucuuu ucuagccacu acagucucug   2580
ucuuuccuuu cacagccaag cuucuugaaa ggcugucua cacugcguu cuuccuuccu     2640 caccuccaau uuccucuuca acccacugcu uccugacucg cucuacuccg uggaagcacg   2700
```

```
cucacaaagg uucccagugc ccccgacaag cccccugcugg ugucuccauc uccugccaag  2760
cauccuccag ugccuccucc ugugggccug gccucagggc uauggacaga cuccuguccc  2820
aucccagaga ccccucguga ucgugcccug gcacgugggc cguggcccgg cuggucggc   2880 ugaagaacug cggauggaag cugcggaaga ggcccgaug  gggcccacca ucccggaccc  2940
aagucuucuu ccuggcgggc cucgucuc   cuuccugguu ugggcggaag ccaucaccug  3000
gaugccuacg ugggaaggga ccucgaaugu gggaccccag ccccucucca gcucgaaauc  3060
ggcagacuag gauggaagug cccugugagc ugggggggccc uucaagggc  caaggagaaa  3120 acgcaggccg agggaccagc cuuccaaaug ggcuucaagc uccaaugacc uccgcucgcc  3180
cccucgaaau gucuggaaaa cauaaugggc agauuuucug ucuucaaagu uuccggcuaa  3240
accucuucaa guucuuuauu guuuggacu  gagacacuca gccauguuaa uggguaguuu  3300
cuuuuguauu ugccuugaaa ggccaaaaua uuuuuauauu gccacagaca aagccaccua  3360
uuuaaaaaug aacuccaugu ccgucguuuc ccaccaggag acuauguacc auguguugu   3420 cucuauguau ucugggucu  ugaaacaggu ucucauggg  gauggucauu caccacgguc  3480 cagagggca  gaacaggcgg cgcuugccuu gccagggggg ccuggggaac gugggcccuc  3540
aucucagauc ugccccagu  auguuuagga cgcgagcccc agaaggaucu gggaguaaac  3600
uuaacauuca cugugucucu gcucugcauc cgccauuugu gugguuucu  ggacuguggg  3660 cuguguguac cuugguuggu gacucaguga gaagaagcag gaaugccaaa gauacguga   3720 auguucugag uuuuguugcu guuguuguug agaguuguu  ucacuggguau cuauugcauu  3780 guauaauaaa ugaccagaug aaugaauga  ugaagcaaga gagaaugaau aaacaaguaa  3840
auagguaaag aaguaagcaa gccaggauga gagugugugu acacaagacc augguucauc  3900
cgcuuugaug gcuaggcaau caauauauaa auagaaaaa  accagugaau cacuaaguaa  3960
uagggcaaca cacaaagcga uaucagguga uuauggacua aggguaugu  guaacucaaa  4020 uauaugccuc ugacauuuga caaugaaaaa gaaccuaaau gaaagaaaga augggauguau 4080 gaguagugaa gugcagaaug agacauagau uuugaggccc gucaaaauga aagaugcaa   4140 guuagggaac aagugaucaa aagggagaag ggaaagguuu uuuuuaaaaa accaaaacaa  4200
caaagaaagg uuaaaaaaa  aaacagacua gaggaugagu aaugaguaac ucuguaagga  4260
ggaccauguc agacuauugu aagcuaagca uuaggacuga uacaaauaau auaugcuccu  4320
ggcauagaaa aauaaaccac agagaacgag uucaaagaau agcaaagaaa gaaagaggac  4380
ccagugggcg aaagaugaga guguacuuuu accaaaaguu aucuaagccu gagcacuuga  4440
agucugcaca uaaauaaaua aaugacaaaa gaaagaaaaa aaggccaaaa agucuacauu  4500
gcgugugugg auggaugaau gagcagugggg agucagcgc  caggugacaa gauguuguga  4560 ggguuuuga  gucauccagu ccugggcacu gaggucuguu agaugaaagg auaugagaaa  4620
gguaauauug guaauaaag  aaauaggaaa caaguaaca  aauguuaagu acagaaauac  4680
auuaaugggu gguaaauaaa gauguaaaag aaggcaaugc gaucgauggu ggcaaaagau  4740
caucacagau uaagggcuau ggcuggucca cuucuagaaa accacaggcu guccauuaaa  4800
uaaugaacau cuaagugaac aagucaguga guaccaaaau agacaaggau gaggugaaug  4860
agaagacaug gccccauggg uccuccugau gagggugunu gggucccccc uggcacccc   4920 agcugcauga aaaugaagga caggaggnau ggaaagcuau gacagaagag agaaggaac   4980 gguaaaaaga aauaacaacc aaauggauaa augggunagaa ccacgagaag aguuaggcua  5040
ggacuuguca uaagggcacc ugacuccacu aauagaggaa uaaaugccua auaaaaagag  5100
```

| | |
|---|---|
| agcaagcagg aaggaaggau gcuaugaaug caggaaggaa guaaugagug agacguggaa | 5160 |
| ccgcacggcc aaggauggac guuugcgggu ggcuuuuuga ugcguacagc caagccacuc | 5220 |
| cauggcaaug agcuccgaag acaaagugca agagagaaug agugagagag ugagagagag | 5280 |
| agaaacaaua aaaaauggga agaaauguaa aaggaagaa aggaagagag guauauauu | 5340 |
| aaggaauaaa uacaugcaug cagauuuaag acagagccau gcuagaacag gaaugaaagg | 5400 |
| cugugugaac caagcagacc gcuuaauugg caccagugcu gcugguaugg ucaaucaccu | 5460 |
| acucaacuaa ggaacggcuc aaagcauaca caugggaggg aggaguggg ccacagagag | 5520 |
| agggcccauu aguugcagau uacgaugua ccaguuaggu gcaccugccu ucgagaagug | 5580 |
| uaaaauaag uauuuacaua gaaagaaaga cugaauggau gcacggugaa ugcaugaaug | 5640 |
| auugaacgac agaaaagauu ugcauugacc gaugaggagg gcauuguaga cagggaugag | 5700 |
| ggucauugau ccuggugca gaucuccaaa agaaugacag aaagaaagag ggagugguggg | 5760 |
| aaagaaacaa uaggauggga aaaaaugaaa auagaaaaaa ggaagugaaa gagauaauaa | 5820 |
| auaauuagau caaauaaguu gaugaaaggg gacugguuua gcacaagcca uccacauuaa | 5880 |
| uucaaaccug uggcucugaa guuuguuuuu uaaaugacca caaguguaag acugaaugaa | 5940 |
| agaauaaaug cgugcauucc auaggaugca agaaaaggag ugaggaaugg gaaaauugga | 6000 |
| agaacgagag agggagagau guaagaaaag aaaggaaaag ugaaguaggc auugaaaga | 6060 |
| aaaggcacuu cuuggacaag cacugaaaua uaaugagaca guuuuaccca uuaaauauaa | 6120 |
| uaaacaguaa acguugaggu ucaucaauaa aagcacagau accugaauag aggagugacc | 6180 |
| ugaauagaau ucguucagcc gaacgaauga gaauggauga uuuucacuau ccugugcacu | 6240 |
| caaggcccaa aagagaaagc aagagaggag agaauaugga aacguaugac aggauguaua | 6300 |
| uaagcaauac aaacauauug aaugaauaaa uaaagacaua aauauguggg agaguggacc | 6360 |
| acgcaaggac aaaagagga gagaaggcag caagaauuau gacuaauuca aaacuggguu | 6420 |
| ccugagauag uuaaauaaau ccugcaccaa auccccaggg ggagaaauua acaaacaaaa | 6480 |
| gacagcccca cacggaccag ugugcagaag gcuccaggaa ccgcagauua ugguuaaucc | 6540 |
| aauucugugc accugaagguc cauaaauaaa agaauaagua uugaaaugaa agaaugacag | 6600 |
| aaagaaugaa uggacacaug aacgacugaa uuagaaaugg aaaugccugg cacagccagg | 6660 |
| aaggagcugc ccaugggauu gucauucauc ucacucuggg caccgaggu ccauaagcgu | 6720 |
| gaaaagaggc aggaagagaa gugucaggga gucaaagaua gagcuaagga aaggcaaaaa | 6780 |
| ugaaacuaaa ugaaagcgaa agggaaaaua aagaaaaacc aauaaaaaag agaacgaaua | 6840 |
| cgugggugua ucuguaagag uaggaucugu uaggauuagu cauaagacug ucaguaaucc | 6900 |
| ugaagaugga ugagauaauc caggcccagg uucccagggg gagggaaaau ggagaaaaua | 6960 |
| uaaaagaug ugaaaaagga aaaa | 6984 |

```
<210> SEQ ID NO 10
<211> LENGTH: 4489
<212> TYPE: DNA
<213> ORGANISM: Homo sapiens
<220> FEATURE:
<223> OTHER INFORMATION: Human Meg3 isoform 2 (ENSU00000452120)

<400> SEQUENCE: 10
```

| | |
|---|---|
| cagagaggga gcgcgccuug gcucgcuggc cuuggcggcg gcuccucagg agagcugggg | 60 |
| cgcccacgag aggaucccuc acccggggucu cuccucaggg augacaucau ccguccaccu | 120 |

```
ccuugucuuc aaggaccacc uccucuccau gcugagcugc ugccaagggg ccugcugccc    180
aucuacaccu cacgagggca cuaggagcac gguuuccugg aucccaccaa cauacaaagc    240
agccacucac ugaccccag gaccaggaug gcaaaggaug aagaggaccg aacugacca     300 gccagcuguc ccucuuaccu aaagacuuaa accaaugccc uagugagggg cauggggca    360 uuaagcccug accuuugcua ugcucauacu ugacucuau gaguacuuuc cuauaagucu     420
uugcuugugu ucaccugcua gcaaacugga guguuucccu ccccaagggg gugucagucu    480
uugucgacug acucugucau cacccuuaug auguccugaa uggaaggauc ccuuugggaa    540
auucucagga gggggaccug ggccaagggc uggccagca uccugcuggc aacuccaagg     600 cccuggguggg gcuucuggaa ugagcaugcu acugaaucac caaaggcacg cccgaccucu   660
cugaagaucu uccuauccuu uucgggggga auggggucga ugagagcaac cuccuaggu    720 uguugugaga auuaaaugag auaaaagagg ccucaggcag gaucuggcau agaggaggug    780
aucagcaaau guuuguugaa aagguuugac aggucagucc cuucccaccc cucuugcuug    840
ucuuacuugu cuuauuuauu uccaacagc acuccaggca gcccugugcc acgggcucuc    900
cuugcaucag uaggggcuu ugcagagacc aucgacgggc ugacuugagu aagaacacga    960
auuaugcaug uggccauuuc cagagcacuu ucuaugugau augaacaugu gauuuuuaug   1020
uaauaugugu auguaaacga ggcagccuca uuuccaggug aggaugcauu gguaguguu    1080 gauuuuugua auuuaaagaa gcugaaaggg agagaggacc cgugaggacu gaacucucug    1140
ucccaugggg uagggcuuac auuuacauua aagaaacaga aacuugcugg gagggugaag    1200 uauugguca cauugcuggc aacagaaggg guuggaguug gacccagggu gccacgcuag    1260
cugcccucac cccuucuucc ccucuggccc agaguuauac uaagaguccu uuuauuucaa    1320
accaaauguu ugacaauggg acagucuguu ugaaauccca gcugccuggg ggugucuugg    1380
gggucugggu ggccccagug cugguaccau gugcuggcuu caccuuuuaa uaacagugug    1440
accuuaaaca agucgcuuaa cuacucuaag uuucaguuuc uuucaugguc uaaauggaga    1500
uuaaaacaca cacacacaca cacacacaca cacacacaca cacacccccu cguguaucua    1560
ccccacaggg cgcuuuugaa gaccaaaugc uguaacuacu augaaagugc uuuguaaauu    1620
gcuguggaaa gugugagcua cucaagcacc cgaggcuguc ccuccuugcu cacaugucca    1680
gcccaauucu cccuuaguga gaacagcacu caguaggugc ugugugaguu uguguucaau   1740
uaagaaauuc cagaauaaau aaaaaugaau uaauucaaca aacauuuucu ggggcaccga    1800
caaucugccc agugcaccag gcuagguauc ugauacaaag auaaugaaaa cagucucuug    1860
gaaccuaauu ggggguccuca uuugaccagg aauuucuuuc gucccguuuu aagccaacca    1920 guuuugccg acaagacaa aaacaacuug ggcugcuuua gaagaagccca gcucagugua    1980 gacaauagcu gcccagccuc ugaaaggggc ugauuggauu auguggcaaa uggaggugca    2040
aggaugacuu ggacgguguac aaaugaagug ggcggagacc ugcuuugagu uaauccaggc    2100
uauuaggagg ggaccuuuug ucuuccagag acuggcagga gcuuuuacca guggguuuuua   2160 cauccuuaau guucaggacg aauaauuau ggucagugaa aauccaggcc ccagugagau    2220
ucgagugggc uguaaaaucg agaguccugc ucccagugag uaauguuagu gaauguuucu    2280
gucacuuuuu gcaaccgucc auucauuuga uccucacaac ucccuguccu gagccaggac    2340
cggccacugc cacucccagg gaaacagagg cugucaagag gcuccacaga uugggcccca    2400
cuggaucauu gaaccccugu uccugaguu cuagaggaag aauugaccu gucucagucc     2460 cggccaccuc cagaaggccu cccucugcau uucugacuuu gcugugccgg cagccuggag    2520
```

| | |
|---|---|
| ccucccaggu cccugcuguc aucuuuucua gccacuacag ucucugucuu uccuuucaca | 2580 |
| gccaagcuuc uugaaaggcc ugucuacacu ugcugucuuc cuuccucacc uccaauuucc | 2640 |
| ucuucaaccc acugcuuccu gacucgcucu acuccgugga agcacgcuca caaagguaaa | 2700 |
| gacuuuucug uggcuuaauc cuugucaugu uuucggcuca uggacacaag gacacauuuu | 2760 |
| caugccuucu cucacagggc ucugcgucuc cgguucacuu cuguqucuuu acacucccuu | 2820 |
| cacagagaca cuugcuccccc cuucucucgu ucuuagcauc cccuaggaac uugcacaccc | 2880 |
| aggucucucg acuucggac cugcuucuua ccaugccguc uuaagcaguc aggagucgcu | 2940 |
| gccugqquuc gaguccuagu aaauuacuu agugcugaga ccuuggggua gguaaacuuu | 3000 |
| uccaagccag guuuaucuca guucaaaau aggguuaauc gucuuuaucu ggcaggucag | 3060 |
| gugggauguc ucacagguaa gcaccagaug ccauuugaaa ggcuugaagc aaagucaaua | 3120 |
| aagcauucau gggaaaauac aacuggaggc accacuagau uucguauac auuagguucc | 3180 |
| cacgqggaqg accgaagaga aagaaagaa guggaaaggg aggagcgugc aggagagaca | 3240 |
| ggagaagaga auaacuaaac aaagacauua aagacaaaaa aaaaguagga aagggagacu | 3300 |
| uagaaaauau uaaagccac caaaaacaca uccaaagacg guucccccuu acguuaguug | 3360 |
| ggcuaaaaga aagcaaaugg gaagaagguu uuaaauugau aucccagug acaaauccca | 3420 |
| ggaagcuuuc acaucaaauc acccuauucu ggguuuuuaa cuccuuccau cgaguuuaac | 3480 |
| cucuuuaccu cccacauccu gguaaacccu gccccucccc uaccgccccc uuugcuggug | 3540 |
| auuaaauccu gaagguacac gaaguauuuc agugaaugaa uggcuaacag aaaagggccu | 3600 |
| ccccucccc uuaccccuggc gguguuuuuc aguuuauuc cacuuuccgc ccuuucccu | 3660 |
| uaaugaacac agggcuaauc ucgggccuug ucgaaggaag aggcugcaga cguuaaugag | 3720 |
| guuagcugcu ggauccagu auucgucgca uaaggauccu ucuuugucug cgaaggaaaa | 3780 |
| acacacugau uaucauaaug aggugaacug gccaccgccg ggccggggcg auguggcuuc | 3840 |
| uuaagccaca cuucuaauuu uggugaugga gccgacauuu cuuggcuuc ucauuuaagu | 3900 |
| cuuugccucu gucccagugc gaaguccauu cagcggqquu gaaaguugca ggcagcuuug | 3960 |
| ggaaggggg cgucggacag gguugcauug uagaaagugg cuuguucga uccuucgcac | 4020 |
| agaugcaaau ggccagagca uucauucccu uucuucaaga gcugaggacu gggggggcca | 4080 |
| cuggugauca guucccaacu cuagcucucc ucugacucau cucaggaccc auugaggaca | 4140 |
| uccaaaacuc acucaagauc accaagguggu aggaaaguac uaacuccugg gcauagcccu | 4200 |
| aggggaguga cuacaaugug aauacucaug gaaugccuag ccaggugaag aagugaaugc | 4260 |
| auguuggcau cccagaggga cccccccuuaa gagggcauag uuggggguuc agauuugacu | 4320 |
| ccagcauacu guugaaauug ggcacagggg gcuagdauu agcaggauc aaucaguggga | 4380 |
| gaggagauua aaacucacau cugggagucc ggaaucagaa cuuguaguuc uuuuuuuga | 4440 |
| aauggagucu cgcucugucg cccaggcugg agugcagugg cgugaucuc | 4489 |

<210> SEQ ID NO 11
<211> LENGTH: 2672
<212> TYPE: DNA
<213> ORGANISM: Homo sapiens
<220> FEATURE:
<223> OTHER INFORMATION: Human Meg3 isoform 3 (ENSU00000424076)

<400> SEQUENCE: 11

| | |
|---|---|
| cggagagcag agagggagcg cgccuuggcu cgcuggccuu ggcggcggcu ccucaggaga | 60 |

| | |
|---|---|
| gcugggcgc ccacgagagg auccucacc cggucucuc cucagggaug acaucauccg | 120 |
| uccaccuccu ugucuucaag gaccacucc ucuccaugcu gagcugcugc caagggccu | 180 |
| gcugcccauc uacaccucac gagggcacua ggagcacggu uccuggauc ccaccaacau | 240 |
| acaaagcagc cacucacuga cccccaggac caggauggca aaggaugaag aggaccggaa | 300 |
| cugaccagcc agcugucccu cuuaccuaaa gacuuaaacc aaugcccuag ugaggggca | 360 |
| uugggcauua agcccugacc uuugcuaugc ucauaccuug acucuaugag uacuuuccua | 420 |
| uaagucuuug cuuguguuca ccugcuagca aacuggagug uuucccuccc caagggggug | 480 |
| ucagucuuug ucgacugacu cugucaucac ccuuaugaug uccugaaugg aaggauccccu | 540 |
| uugggaaauu cucaggaggg ggaccugggc caagggcuug ccagcaucc ugcuggcaac | 600 |
| uccaaggccc uggugggcu ucuggaauga gcaugcuacu gaaucaccaa aggcacgccc | 660 |
| gaccucucug aagaucuucc uauccuuuuc uggggggaaug gggucgauga gagcaaccuc | 720 |
| cuaggguugu ugugagaauu aaaugagaua aagagggccu caggcaggau cuggcauaga | 780 |
| ggaggugauc agcaaauguu uguugaaaag guuugacagg ucagucccuu cccacccccuc | 840 |
| uugcuugucu acuugucuu auuuauucuc caacagcacu ccaggcagcc cuuguccacg | 900 |
| ggcucucccuu gcaucagcca agcuucuuga aaggccuguc uacacuugcu gucuuccuuc | 960 |
| cucaccucca auuccucuu caacccacug cuuccugacu cgcucuacuc cguggaagca | 1020 |
| cgcucacaaa ggcacguggg ccguggcccg gcgggucgg cugaagaacu gcggauggaa | 1080 |
| gcugcggaag aggcccugau ggggccacc aucccggacc caagucuucu uccuggcggg | 1140 |
| ccucucgucu ccuuccuggu uugggcgaa gccaucaccu ggaugccuac guggaaggg | 1200 |
| accucgaaug ugggacccca gccccucucc agcucgaaau cggcagacua ggauggaagu | 1260 |
| gcccugugag cugggggggcc cuucaaaggg ccaaggagaa aacgcaggcc gagggaccag | 1320 |
| ccuuccaaau gggcuucaag cuccaaugac cuccgcucgc ccccucgaaa ugucuggaaa | 1380 |
| acauaauggg cagauuuucu gucuucaaag uuuccggcua aaccucuuca aguucuuuau | 1440 |
| uguuugggac ugagacacuc agccauguua auggguaguu ucuuuguau uugccuugaa | 1500 |
| aggccaaaau auuuuuauau ugccacagac aaagccaccu auuuaaaaau gaacuccaug | 1560 |
| uccgucguuu cccaccagga gacuauguac caugugugug ucucuaugua uucugggguc | 1620 |
| uugaaacagg uuucuauggg ggauggucau ucaccacggu ccagagggc agaacaggcg | 1680 |
| gcgcuugccu ugcccagggg gccugggaa cgugggcccu caucucagau cugcccccag | 1740 |
| uauguuuagg acgcgagccc cagaaggauc ugggaguaaa cuuaacauuc acugugucuc | 1800 |
| ugcucugcau ccgccauuug ugugugutuuc uggacugugg gcugugugua ccuugguugg | 1860 |
| ugacucagug agaagaagca ggaaugccaa agauacugug aauguucuga guuuguugc | 1920 |
| uguuguuguu gagagguugu ucacuggua ucuauugcau uguauaauaa augaccagau | 1980 |
| gaaugaauga gugaagcaag agagaaugaa uaaacaagua aauagguaaa gaaguaagca | 2040 |
| agccaggaug agagugugug uacacaagac caugguucau ccgcuuugau ggcuaggcaa | 2100 |
| ucaauauaua aauagaaaaa aaccagugaa ucacuaagua auagggcaac acacaaagcg | 2160 |
| auaucaggug auuauggacu aaggggguaug uguaacucaa auauaugccu cugacauuug | 2220 |
| acaaugaaaa agaaccuaaa ugaaagaaag aauggaugua ugaguaguga agcagaauu | 2280 |
| gagacauaga uuuugaggcc cgucaaaaug aaaagaugca aguuaggaa caagugauca | 2340 |
| aaagggagaa gggaaagguu uuuuuaaaa aaccaaaaca acaaagaaag guuaaaaaaa | 2400 |
| aaaacagacu agaggaugag uaaugaguaa cucuguaagg aggaccaugu cagacuauug | 2460 |

| | |
|---|---:|
| uaagcuaagc auuaggacug auacaaauaa uauaugcucc uggcauagaa aaauaaacca | 2520 |
| cagagaacga guucaaagaa uagcaaagaa agaaagagga cccaguggc gaaagaugag | 2580 |
| aguguacuuu uaccaaaagu uaucuaagcc ugagcacuug aagucugcac auaaauaaau | 2640 |
| aaaugacaaa agaaagaaaa aaaggccaaa aa | 2672 |

<210> SEQ ID NO 12
<211> LENGTH: 2368
<212> TYPE: DNA
<213> ORGANISM: Homo sapiens
<220> FEATURE:
<223> OTHER INFORMATION: Human Meg3 isoform 4 (ENSU00000523671)

<400> SEQUENCE: 12

| | |
|---|---:|
| cccaaggggg ugucagucuu ugucgacuga cucugucauc acccuuauga uguccugaau | 60 |
| ggaaggaucc cuuugggaaa uucucaggag ggggaccugg gccaagggcu uggccagcau | 120 |
| ccugcuggca acuccaaggc ccuggguggg cuucuggaau gagcaugcua cugaaucacc | 180 |
| aaaggcacgc ccgaccucuc ugaagaucuu ccuauccuuu ucuggggga uggggucgau | 240 |
| gagagcaacc uccuaggguu guugugagaa uuaaaugaga uaaaagaggc cucaggcagg | 300 |
| aucuggcaua gaggagguga ucagcaaaug uuuguugaaa agguuugaca ggucaguccc | 360 |
| uucccacccc ucuugcuugu cuuacuuguc uuauuuauuc uccaacagca cuccaggcag | 420 |
| cccugucca cgggcucucc uugcaucagg uaggggcuuu gcagagacca ucgacgggcu | 480 |
| gacuugagua agaacacgaa uuaugcaugu ggccauuucc agagcacuuu cuaugugaua | 540 |
| ugaacaugug auuuuuaugu aauaugugua uguaaacgag gcagccucau uccaggauga | 600 |
| ggaugcauuu ggauaguuug auuuuugauaa uuuaagaag cugaaaggga gagaggaccc | 660 |
| gugaggacug aacucucugu cccaugggu aggguuaca uuucauuaa agaaacagaa | 720 |
| acuugcuggg aagguauaagu auuuggucac auugcuggca acagaagggg uuggaguugg | 780 |
| acccagggug ccacgcuagc ugcccucacc ccuucuuccc cucuggccca gaguuauacu | 840 |
| aagaguccuu uuauucaaaa ccaaauguuu gacaauggga cagucuguuu gaaaucccag | 900 |
| cugccugggg uggucuuggg ggucggugu gccccagugc uggauccaug ugcuggcuuc | 960 |
| accuuuuaau aacagugga ccuuaaacaa gucgcuuaac uacucuaagu uucaguuucu | 1020 |
| uucauggucu aaauggagau uaaaacacac acacacacac acacacacac acacacacac | 1080 |
| acaccccuc uguauuac cccacagggc gcuuugaag accaaaugcu guaacuacua | 1140 |
| ugaaagugcu uuguaaauug cuguggaaag ugugagcuac ucaagcaccc gaggcugucc | 1200 |
| cuccuugcuc acauguccag cccaauucuc ccuuagugag aacagcacuc aguaggugcu | 1260 |
| gugugugui uguucaau aagaaauucc agaauaaaua aaaaugaau aauucaacaa | 1320 |
| acauuuucug gggcaccgac aaucugccca gugcaccagg cuagguaucu gauacaaaga | 1380 |
| uaaugaaaac agucucuugg aaccuaaug ggguccucau uugaccagga auucuuucg | 1440 |
| ucccguuuua agccaaccag uuuguccgg acaagacaaa acaacuugg gcugcuuuag | 1500 |
| agaagcccag cucaguguag acaauagcug cccagcccucu gaagggggcu gauuggauua | 1560 |
| uguggcaaau ggaggugcaa ggaugacuug gacggugaca aaugaagugg gcggagaccu | 1620 |
| gcuuugaguu aauccaggcu auuaggaggg gaccuuugu cuuccagaga cuggcaggag | 1680 |
| cuuuuaccag ugguuuuac auccuuaaug uucaggacga auaauuuaug gucagugaaa | 1740 |
| auccaggccc cagugagauu cgagugggcu guaaaaucga gagccugcu cccagugagu | 1800 |

| | |
|---|---|
| aauggaugug aauguuucug ucacuuuuug caaccgucca uucauuugau ccucacaacu | 1860 |
| cccuguccug agccaggacc ggccacugcc acucccaggg aaacagaggc ugucaagagg | 1920 |
| cuccacagau ugggccccac uggaucauug aaccccuguu cccugaguuc uagaggaaga | 1980 |
| auuguaccug ucucagucCC ggccaccucc agaaggccuc ccucugcauu ucugacuuug | 2040 |
| cugugccggc agccuggagc cucccagguc ccugcuguca ucuuuucuag ccacuacagu | 2100 |
| cucugucuuu ccuuucacag ccaagcuucu ugaaaggccu gucuacacuu gcugucuucc | 2160 |
| uuccucaccu ccaauuuccu cuucaaccca cugcuuccug acucgcucua ucccguggaa | 2220 |
| gcacgcucac aaaggcacgu gggccgugcc ccggcugggu cggcugaaga acugcggaug | 2280 |
| gaagcugcgg aagaggcccu gauggggccc accaucccgg acccaagucu cuuccuggc | 2340 |
| gggccucucg ucuccuuccu gguuuggg | 2368 |

<210> SEQ ID NO 13
<211> LENGTH: 1771
<212> TYPE: DNA
<213> ORGANISM: Homo sapiens
<220> FEATURE:
<223> OTHER INFORMATION: Human Meg3 isoform 5 (ENSU00000423456)

<400> SEQUENCE: 13

| | |
|---|---|
| cggagagcag agagggagcg cgccuuggcu cgcuggccuu ggcggcggcu ccucaggaga | 60 |
| gcuggggcgc ccacgagagg auccucacc cggguccucuc cucagggaug acaucauccg | 120 |
| uccaccuccu ugucuucaag gaccaccucc ucuccaugcu gagcugcugc caaggggccu | 180 |
| gcugcccauc uacaccucac gagggcacua ggagcacggu uccuggauc ccaccaacau | 240 |
| acaaagcagc cacucacuga cccccaggac caggauggca aaggaugaag aggaccggaa | 300 |
| cugaccagcc agcugucccu cuuaccuaaa gacuuaaacc aaugcccuag ugaggggca | 360 |
| uugggcauua agcccugacc uuugcuaugc ucauacuuug acucuaugag uacuuuccua | 420 |
| uaagucuuug cuuguguuca ccugcuagca aacuggagug uuucccuccc caaggggug | 480 |
| ucagucuuug ucgacugacu cugucaucac ccuuaugaug uccugaaugg aaggauccou | 540 |
| uugggaaauu ucaggagggg ggaccugggc caagggcuug gccagcaucc ugcuggcaac | 600 |
| uccaaggccc uggugggcu ucuggaauga gcaugcuacu gaaucaccaa aggcacgccc | 660 |
| gaccucucug aagaucuucc uauccuuuuc uggggaaaug gggucgauga gagcaaccuc | 720 |
| cuaggguugu ugugagaauu aaaugagaua aaagaggccu caggcaggau cuggcauaga | 780 |
| ggaggugauc agcaaaugu uguugaaaag guuugacagg ucagucccuu cccacccuc | 840 |
| uugcuugucu uacuugucuu auuuauucuc caacagcacu ccaggcagcc cuuguccacg | 900 |
| ggcucuccuu gcaucagcca agcuuccuuga aaggccuguc uacacuugcu gucuuccuuc | 960 |
| cucaccucca auuccucuu caacccacug cuuccugacu cgcucuacuc cguggaagca | 1020 |
| cgcucacaaa gggcuaaucu cgggccuugu cgaaggaaga ggcugcagac guuaaugagg | 1080 |
| uuagcugcug gauccaguaa uucgucgcau aaggauccuu cuuugucgc gaaggaaaaa | 1140 |
| cacacugauu aucauaauga guuccugacc uggccauccc ggggugcccu ugaccagccc | 1200 |
| cgugucuccu cagggugucc cagcaccagc cuggcacaga gugggcucag uuagaguau | 1260 |
| gugggauguu gguucgcca ggcacguggg ccguggccccg gcggggucgg cugaagaacu | 1320 |
| gcggauggaa gcgcggaag aggcccugau ggggcccacc aucccggacc caagucuucu | 1380 |
| uccuggcggg ccucucgucu ccuuccuggu uugggcggaa gccaucaccu ggaugccuac | 1440 |
| guggggaaggg accucgaaug ugggacccca gccccucucc agcucgaaau cccuccacag | 1500 |

```
ccacggggac acccugcacc uauucccacg ggacaggcug gacccagaga cucuggaccc    1560
ggggccuccc cuugaguaga gacccgcccu cugacugaug gacgccgcug accugggguc    1620
agacccgugg gcuggacccc ugcccacccc gcaggaaccc ugaggccuag gggagcuguu    1680
gagccuucag ugucugcaug ugggaagugg gcuccuucac cuaccucaca gggcuguugu    1740
gaggggcgcu gugaugcggu uccaaagcac a                                   1771
```

<210> SEQ ID NO 14
<211> LENGTH: 1726
<212> TYPE: DNA
<213> ORGANISM: Homo sapiens
<220> FEATURE:
<223> OTHER INFORMATION: Human Meg3 isoform 6 (ENSU00000519709)

<400> SEQUENCE: 14

```
agagagggag cgcgccuugg cucgcuggcc uuggcggcgg cuccucagga gagcuggggc      60
gcccacgaga ggaucccuca cccggggucuc uccucaggga ugacaucauc cguccaccuc    120
cuugucuuca aggaccaccu ccucuccaug cugagcugcu gccaaggggc cugcugccca    180
ucuacaccuc acgagggcac uaggagcacg guuuccugga ucccaccaac auacaaagca    240
gccacucacu gaccccagg accaggaugg caaaggauga agaggaccgg aacugaccag      300
ccagcugucc cucuuaccua aagacuuaaa ccaaugcccu agugagggg cauugggcau      360 uaagcccuga ccuuugcuau gcucauacuu ugacucuaug aguacuuucc uauaagucuu     420
gcuugguguu caccgcuag caaacuggag uguuucccuc ccaagggggg ugucagucuu      480
ugucgacuga cucugucauc acccuuauga uguccugaau ggaaggaucc cuuugggaaa    540
uucucaggag ggggaccugg gccaagggcu uggccagcau ccugcuggca acuccaaggc     600 ccugggugg cuucuggaau gagcaugcua cugaaucacc aaaggcacgc ccgaccucuc      660
ugaagaucuu ccuauccuuu ucuggggaa uggggucgau gagagcaacc uccuaggguu      720
guugugagaa uuaaaugaga uaaaagaggc ucaggcagg aucuggcaua gaggagguga      780
ucagcaaaug uuuguugaaa agguuuugaca ggucagcccc uucccacccc ucuugccuugu   840 cuuacuuguc uuauuuauuc uccaacagca cuccaggcag cccuugucca cgggcucucc     900
uugcaucagc caagcuucu gaaaggccug ucuacacuug cugucuuccu uccuccaccuc    960 caauucccuc uucaacccac ugcuuccuga ucgcucuac uccgguggaag cacgcucaca    1020 aagguuccca gugccccga caagccccug cuggugucuc caucccugc caagcauccu      1080 ccagugccuc cuccugugg ccuggccuca gggcuaugga cagacccug ucccauccca      1140 gagacccccuc gugaucgugc ccuguaguca ccccacucca ccgaaaagua aacugcaggc    1200
acgugggccg uggcccggcu gggucggcug aagaacugcg gauggaagcu gcggaagagg   1260
cccugauggg gccaccauc ccggacccaa gucuucuucc uggcggggccu cucgucuccu    1320 uccugguuug gcggaagcc aucaccugga ugccuacgug ggaagggacc ucgaaugugg     1380
gaccccagcc ccucuccagc ucgaaauccc uccacagcca cggggacacc cugcaccuau    1440
ucccacggga cagggcuggac ccagagacuc uggaccgggg gccuccccuu gaguagagac   1500
ccgcccucug acugauggac gccgcugacc uggggucaga cccgugggcu ggaccccugc   1560 ccacccccgca ggaaccugga ggccuagggg agcuguugag ccuucagugu cugcaugugg   1620 gaaguggggcu ccuucaccuua ccucacaggg cuguuguggag gggcgcugug augcgguucc  1680
aaagcacagg gcuuggcgca ccccacugug cucucaauaa augugu                    1726
```

<210> SEQ ID NO 15
<211> LENGTH: 1721
<212> TYPE: DNA
<213> ORGANISM: Homo sapiens
<220> FEATURE:
<223> OTHER INFORMATION: Human Meg3 isoform 7 (ENSU00000398474)

<400> SEQUENCE: 15

```
ugaauuaauu caacaaacau uuucuggggc accgacaauc ugcccagugc accaggcuag      60
guaucugaua caaagauaau gaaaacaguc ucuuggaacc uaauuggggu ccucauuuga     120
ccaggaauuu cuuucguccc guuuuaagcc aaccaguuuu guccggacaa gacaaaaaca     180
acuugggcug cuuuagagaa gcccagcuca guguagacaa uagcugccca gccucugaaa     240
ggggcugauu ggauuaugug gcaaauggag gugcaaggau gacuuggacg gugacaaaug     300
aagugggcgg agaccugcuu ugaguuaauc caggcuauua ggaggggacc uuugucuuc     360
cagagacugg caggagcuuu uaccaguggu uuuuacaucc uuaauguuca ggacgaauaa     420
uuuauggauca gugaaaaucc aggccccagu gagauucgag ugggcuguaa aaucgagagu     480
ccugcuccca gugaguaaug guagugaaug uuucugucac uuuuugcaac cguccauuca     540
uuugauccuc acaacucccu guccuagacc aggaccggcc acugcacucu ccagggaaac     600
agaggcuguc aagaggcucc acagauuggg ccccacugga ucauugaacc ccuguucccu     660
gaguucuaga ggaagaauug uaccugcucu agucccggcc accuccagaa ggccuccuc     720
ugcauuucug acuugcugu gccggcagcc uggagccucc caggucccug cugucaucuu     780
uucuagccac uacagucucu gucuuuccuu ucacagccaa gcuucuugaa aggccugucu     840
acacuugcug ucuuccuucc ucaccuccaa uuccucuuc aacccacugc uuccugacuc     900
gcucuacucc guggaagcac gcucacaaag ggcuaaucuc gggccuuguc gaaggaagag     960
gcugcagacg uuaaugaggu uagcugcugg auuccaguau ucgucgcaua aggauccuuc    1020
uuugucugcg aaggaaaaac acacugauua ucauaaugag uuccgaccu ggccaucccg    1080
gggugcccuu gaccagcccc gugucuccuc agggugucec agcaccagcc uggcacagag    1140
ugggcucag uuagaguaug ugggaugug guuucgccag gcacguggc cguggcccgg     1200
cuggucggc ugaagaacug cggauggaag cugcggaaga ggcccugauu gggcccacca    1260
uccggaccc aagucuucuu ccuggcgggc cucucgucuc cuuccugguu ugggcggaag    1320
ccaucaccug gaugccuacg ugggaaggga ccucgaaugu gggaccccag ccccucucca    1380
gcucgaaauc ccuccacagc acgggggaca cccugccuccu auccacggg gacaggcugg    1440
acccagagac ucuggacccg gggccucccc uugaguagag accgcccuc ugacugaugg    1500
acgccgcuga ccuggggguca gacccgugg cuggaccccu gcccaccccg caggaacccu    1560
gaggccuagg ggagcuguug agccuucagu gucugcaugu gggaaguggg cuccuuccacc    1620
uaccucacag gcuguugug aggggcgcug ugaugcgguu ccaaagcaca gggcuuggcg    1680
caccccacug ugcucucaau aaauguguuu ccugucuuaa c                       1721
```

<210> SEQ ID NO 16
<211> LENGTH: 1712
<212> TYPE: DNA
<213> ORGANISM: Homo sapiens
<220> FEATURE:
<223> OTHER INFORMATION: Human Meg3 isoform 8 (ENSU00000554639)

<400> SEQUENCE: 16

```
gcagagaggg agcgcgccuu ggcucgcugg ccuuggcggc ggcuccucag gagagcuggg      60
```

| | | |
|---|---|---|
| gcgcccacga gaggaucccu cacccggguc ucuccucagg gaugacauca uccguccacc | 120 | |
| uccuugucuu caaggaccac cuccucucca ugcugagcug cugccaaggg gccugcugcc | 180 | |
| caucuacacc ucacgagggc acuaggagca cgguuuccug gauccaccaa acauacaaag | 240 | |
| cagccacuca cugaccccca ggaccaggau ggcaaaggau gaagaggacc ggaacugacc | 300 | |
| agccagcugu cccucuuacc uaaagacuua aaccaaugcc uagugagggg gcauuggggc | 360 | |
| auuaagcccu gaccuuugcu augcucauac uuugacucua ugaguacuuu ccuauaaguc | 420 | |
| uuugcuugug uucaccugcu agcaaacugg aguguuuccc uccccaaggg ggugucaguc | 480 | |
| uuugucgacu gacucuguca ucacccuuau gaugccucga auggaaggau cccuuuggga | 540 | |
| aauucucagg aggggaccu gggccaaggg cuuggccagc auccugcugg caacuccaag | 600 | |
| gcccugggug ggcuucugga augagcaugc uacugaauca ccaaaggcac gcccgaccuc | 660 | |
| ucugaagauc uuccuauccu uuucgggggg aaugggguucg augagagcaa ccuccuaggg | 720 | |
| uuguugagag aauuaaauga gauaaaagag gccucaggca ggaucuggca uagaggaggu | 780 | |
| gaucagcaaa uguuguuga aaggguuuga caggucaguc ccuucccacc ccucuugcuu | 840 | |
| gucuuacuug ucuauuuuau ucccaacag cacuccaggc agcccuuguc cacgggcucu | 900 | |
| ccuugcauca gccaagcuuc uugaaaggcc ugcuacacu ugcugucuuc cuccucacc | 960 | |
| uccaauuucc ucuucaaccc acugcuuccu gacucgcucu acccgugga agcacgcuca | 1020 | |
| caaagguucc cagugccccc gacaagcccc ugcuggugu ccaucuccu gccaagcauc | 1080 | |
| cuccagugcc uccucugug ggccuggccu cagggcuaug gacagacucc ugucccaucc | 1140 | |
| cagagacccc ucgugaucgu gcccuggcac guggggccgug gcccggcugg gucggcugaa | 1200 | |
| gaacugcgga uggaagcugc ggaagaggcc cugaugggc ccaccauccc ggacccaagu | 1260 | |
| cuucuuccug gcgggccucu cgucuccuuc cugguuuggg cggaagccau caccuggaug | 1320 | |
| ccuacgugg aagggaccuc gaaugugga ccccagccccc ucccagcuc gaaauccccuc | 1380 | |
| cacagccacg gggacacccu gcaccuauuc ccacgggaca ggcuggaccc agagacucug | 1440 | |
| gacccggggc cuccccuuga guagagaccc gcccucugac ugauggacgc cgcugaccug | 1500 | |
| gggucagacc cguggggcugg accccugccc accccgcagg aacccugagg ccuagggag | 1560 | |
| cuguugagcc uucagugucu gcaugugggga agugggcucc uucaccuacc ucacagggcu | 1620 | |
| guugugaggg gcgcugugau gcgguuccaa agcacagggc uggcgcacc ccacugugcu | 1680 | |
| cucaauaaau guguuuccug ucuuaacaaa aa | 1712 | |

<210> SEQ ID NO 17
<211> LENGTH: 1689
<212> TYPE: DNA
<213> ORGANISM: Homo sapiens
<220> FEATURE:
<223> OTHER INFORMATION: Human Meg3 isoform 9 (ENSU00000556736)

<400> SEQUENCE: 17

| | | |
|---|---|---|
| cggagagcag agagggagcg cgccuuggcu cgcuggccuu ggcggcggcu ccucaggaga | 60 | |
| gcuggggcgc ccacgagagg aucccucacc cgggucucuc ucagggaug acaucauccg | 120 | |
| uccaccuccu ugucuucaag gaccaccucc ucuccaugcu gagcugcugc caaggggccu | 180 | |
| gcugcccauc uacaccucac gagggcacua ggagcacggu uccuggauc ccaccaacau | 240 | |
| acaaagcagc cacucacuga cccccaggac caggauggca aaggaugaag aggaccggaa | 300 | |
| cugaccagcc agcugucccu cuuaccuaaa gacuuaaacc aaugcccuag uggggggca | 360 | |

| | |
|---|---:|
| uugggcauua agcccugacc uuugcuaugc ucauacuuug acucuaugag uacuuuccua | 420 |
| uaagucuuug cuuguguuca ccugcuagca aacuggagug uuucccuccc caaggggug | 480 |
| ucagucuuug ucgacugacu cugucaucac ccuuaugaug uccugaaugg aaggauccu | 540 |
| uugggaaauu ucaggagggg ggaccugggc caagggcuug ccagcauccu gcuggcaac | 600 |
| uccaaggccc uggguggcu ucuggaauga gcaugcuacu gaaucaccaa aggcacgccc | 660 |
| gaccucucug aagaucuucc uauccuuuuc uggggaaug gggucgauga gagcaaccuc | 720 |
| cuagguugu ugugagaauu aaaugagaua aaagaggccu caggcaggau cuggcauaga | 780 |
| ggaggugauc agcaaauguu uguugaaaag guuugacagg ucagucccuu cccaccccuc | 840 |
| uugcuugucu uacuugucuu auuuauucuc caacagcacu ccaggcagcc cuuguccacg | 900 |
| ggcucuccuu gcaucagcca agcuucuuga aaggccuguc uacacuugcu gucuuccuuc | 960 |
| cucaccucca auuccucuu caacccacug cuuccgacu cgcucuacuc cguggaagca | 1020 |
| cgcucacaaa gggcuaaucu cgggccuugu cgaaggaaga ggcugcagac guuaaugagg | 1080 |
| uuagcugcug gauccaagua uucgucgcau aaggauccuu cuuugucgc gaaggaaaaa | 1140 |
| cacacugauu aucauaauga ggcacgugg ccguggcccg gcugggucgg cugaagaacu | 1200 |
| gcggauggaa gcugcggaag aggcccugau ggggcccacc aucccggacc caagucuucu | 1260 |
| uccuggcggg ccucucgucu ccuuccuggu uugggcggaa ccaucaccu ggaugccuac | 1320 |
| gugggaaggg accucgaaug uggaccccca gccccucucc agcucgaaau cccuccacag | 1380 |
| ccacggggac acccugcacc uauucccacg ggacaggcug acccagaga cucuggaccc | 1440 |
| ggggccucc cuuagaguaga gacccgcccu cugacugaug gacgccgcug accuggggc | 1500 |
| agacccgugg gcuggacccc ugcccacccc gcaggaaccc ugaggccuag gggagcuguu | 1560 |
| gagccuucag ugucugcaug uggaagugg gcuccuucac cuaccucaca gggcuguugu | 1620 |
| gaggggcgcu gugaugcggu uccaaagcac agggcuuggc gcaccccacu gugcucucaa | 1680 |
| uaaaugugu | 1689 |

<210> SEQ ID NO 18
<211> LENGTH: 1674
<212> TYPE: DNA
<213> ORGANISM: Homo sapiens
<220> FEATURE:
<223> OTHER INFORMATION: Human Meg3 isoform 10 (ENSU00000398518)

<400> SEQUENCE: 18

| | |
|---|---:|
| ggagagcaga gagggagcgc gccuuggcuc gcuggccuug gcggcggcuc ucaggagag | 60 |
| cuggggcgcc cacgagagga ucccucaccc gggucucucc ucagggauga caucauccgu | 120 |
| ccaccuccuu gucuucaagg accaccuccu cuccaugcug agcugcugcc aaggggccug | 180 |
| cugcccaucu acaccucacg agggcacuag gagcacgguu uccuggaucc caccaacaua | 240 |
| caaagcagcc acucacugac ccccaggacc aggauggcaa aggaugaaga ggaccggaac | 300 |
| ugaccagcca gcugucccuc uuaccuaaag acuuaaacca augcccuagu gaggggcau | 360 |
| ugggcauuaa gcccugaccu ugcuaugcu cauacuuuga cucuaugagu acuuuccuau | 420 |
| aagucuuugc uuguguucac cugcuagcaa acuggagug uucccucccc aaggggugu | 480 |
| cagucuuugu cgacugacuc ugucaucacc cuuaugaugu ccugaaugga aggauccuu | 540 |
| ugggaaauuc ucaggagggg gaccgggc aagggcuugg ccagcauccu gcuggcaacu | 600 |
| ccaaggcccu ggguggcuu cuggaaugag caugcuacug aaucaccaaa ggcacgcccg | 660 |
| accucucuga agaucuuccu auccuuuucu ggggaaugg ggucgaugag agcaaccucc | 720 |

```
uaggguuguu gugagaauua aaugagauaa aagaggccuc aggcaggauc uggcauagag    780
gaggugauca gcaaauguuu guugaaaagg uuugacaggu cagucccuuc ccaccccucu    840
ugcuugucuu acuugucuua uuuauucucc aacagcacuc caggcagccc uuguccacgg    900
gcucuccuug caucagccaa gcuucuugaa aggccugucu acacuugcug ucuuccuucc    960
ucaccuccaa uucccucuuc aacccacugc uuccugacuc gcucuacucc guggaagcac   1020
gcucacaaag ggcuaaucuc gggccuuguc gaaggaagag gcugcagacg uuaaugaggu   1080
uagcugcugg auccaguau cgucgcaua aggauccuuc uuugucugcg aaggaaaaac    1140
acacugauua ucauaaugag gcacgugggc cguggcccgg cugggucggc ugaagaacug   1200
cggauggaag cugcggaaga ggcccugaug gggcccacca ucccggaccc aagucuucuu   1260
ccuggcgggc cucucgucuc cuccugguu ugggcggaag ccaucaccug gaugccuacg    1320
ugggaaggga ccucgaaugu gggaccccag ccccucucca gcucgaaauc ccuccacagc   1380
cacggggaca cccugcaccu auccccacgg gacaggcugg acccagagac ucuggacccg   1440
gggccucccc uugaguagag acccgcccuc ugacugaugg acgccgcuga ccuggggucca  1500 gacccguggg cuggaccccu gcccaccccg caggaaccu gaggccuagg ggagcuguug    1560
agccuucagu gucugcaugu gggaaguggg cuccuucacc uaccucacag ggcuguugug   1620
aggggcgcug ugaugcgguu ccaaagcaca gggcuuggcg caccccacug ugcu         1674
```

<210> SEQ ID NO 19
<211> LENGTH: 1582
<212> TYPE: DNA
<213> ORGANISM: Homo sapiens
<220> FEATURE:
<223> OTHER INFORMATION: Human Meg3 isoform 11 (ENSU00000451743)

<400> SEQUENCE: 19

```
cggagagcag agagggagcg cgccuuggcu cgcuggccuu ggcggcggcu ccucaggaga     60 gcugggggcgc ccacgagagg aucccucacc cgggucucuc cucagggaug acaucauccg    120
uccaccuccu ugucuucaag gaccaccucc ucuccaugcu gagcugcugc caaggggccu    180
gcugcccauc uaccucac gagggcacua ggagcacggu uccuggauc ccaccaacau       240 acaaagcagc cacucacuga cccccaggac caggauggca aaggaugaag aggaccggaa    300
cugaccagcc agcugucccu cuuaccuaaa gacuuaaacc aaugcccuag ugagggggca    360
uugggcauua agcccugacc uuugcuaugc ucauacuuug acucuaugag uacuuuccua    420
uaagucuuug cuuguguuca ccugcuagca aacuggagug uuucccuccc caggggguug    480
ucagucuuug ucgacugacu cugucaucac ccuuaugaug uccugaaugg aaggaucccu    540 uuggaaauu ucaggagg ggaccuggc caagggcuug ccagcaucc ugcuggcaac         600 uccaaggccc ugggugggcu ucuggaauga gcaugcuacu gaaucaccaa aggcacgccc    660
gaccucucug aagaucuucc uauccuuuuc uggggggaaug gggucgauga gagcaaccuc   720
cuaggguugu ugugagaauu aaaugagaua aagaggccu caggcaggau cuggcauaga    780
ggaggugauc agcaaauguu uguugaaaag guuugacagg ucagcccuu cccaccccuc    840 uugcuugucu acuugucuu auuuauucuc caacagcacu ccaggcagcc uuguccacg     900 ggcucuccuu gcaucagcca agcuucuuga aaggccuguc uacacuugcu gucuuccuuc    960
cucaccucca auucccucuu caacccacug cuuccugacu cgcucuacuc cguggaagca   1020
cgcucacaaa ggcacguggg ccguggcccg gcugggucgg cugaagaacu gcggauggaa   1080
```

| | |
|---|---|
| gcugcggaag aggcccugau ggggcccacc aucccggacc caagucuucu uccuggcggg | 1140 |
| ccucucgucu ccuuccuggu uugggcggaa gccaucaccu ggaugccuac gugggaaggg | 1200 |
| accucgaaug ugggacccca gccccucucc agcucgaaau cccuccacag ccacggggac | 1260 |
| acccugcacc uauucccacg ggacaggcug gacccagaga cucuggaccc ggggccuccc | 1320 |
| cuugaguaga gacccgcccu cugacugaug gacgccgcug accgggguc agacccgugg | 1380 |
| gcuggacccc ugcccacccc gcaggaaccc ugaggccuag gggagcuguu gagccuucag | 1440 |
| ugucugcaug ugggaagugg gcuccuucac cuaccucaca gggcuguugu gaggggcgcu | 1500 |
| gugaugcggu ccaaagcac agggcuuggc gcaccccacu gugcucucaa uaaaugUguu | 1560 |
| uccugucuua acaaaaacug au | 1582 |

<210> SEQ ID NO 20
<211> LENGTH: 1351
<212> TYPE: DNA
<213> ORGANISM: Homo sapiens
<220> FEATURE:
<223> OTHER INFORMATION: Human Meg3 isoform 12 (ENSU00000520714)

<400> SEQUENCE: 20

| | |
|---|---|
| gcagacggcg gagagcagag agggagcgcg ccuuggcucg cuggccuugg cggcggcucc | 60 |
| ucaggagagc uggggcgccc acgagaggau cccucacccg ggucucuccu cagggaugac | 120 |
| aucauccguc caccccuug ucuucaagga ccaccccuc uccaugcuga gcugcugcca | 180 |
| aggggccugc ugcccaucua caccucacga gggcacuagg agcacgguuu ccuggauccc | 240 |
| accaacauac aaaagcagcca cucacugacc cccaggacca ggauggcaaa ggaugaagag | 300 |
| gaccggaacu gaccagccag cuguccccucu uaccaaaga cuuaaaccaa ugcccuagug | 360 |
| agggggcauu gggcauuaag cccgaccuu ugcuaugcuc auacuuugac ucuaugagua | 420 |
| cuuuccuaua agucuuugcu uguguucacc ugcuagcaaa cuggagUguu ucccuccca | 480 |
| aggggugUc agucuuuguc gacugacucu gucaucaccc uuaugaUguc cugaauggaa | 540 |
| ggaucccuuu gggaaauucu caggaggggg accgggcca agggcuuggc cagcauccug | 600 |
| cuggcaacuc caaggcccug ggUgggcuuc uggaaugagc augcuacuga aucaccaaag | 660 |
| gcacgcccga ccucucugaa gaucuuccua uccuuuucug ggggaauggg gucgaugaga | 720 |
| gcaaccuccu agggUuguug ugagaauuaa augagauaaa agaggccuca ggcaggaucu | 780 |
| ggcauagagg aggugaucag caaauguuug uugaaaaggu uugacagguc aguCccuucc | 840 |
| caccccucuu gcuugucuua cuugucuuau uuauUccca acagcaCucc aggcagcccu | 900 |
| ugccacgggg cuCuccuugc aucagccaag cuucuugaaa ggccugucua cacuugcugu | 960 |
| cuuccuuccu caccuccaau uccucuuca acccacugcu uccugacucg cucuacuccg | 1020 |
| uggaagcacg cucacaaagc agguucccag ugccccgac aagccccugc uggugucucc | 1080 |
| aucuccugcc aagcaUccuc cagugccucc uccugUgggc cuggccucag ggcuauggac | 1140 |
| agacuccugu cccaucccag agaccccucg ugaucgugcc cuggcacgug ggccguggcc | 1200 |
| cggcuggguc ggcugaagaa cugcggaUgg aagcugcgga agaggcccug auggggccca | 1260 |
| ccaucccgga cccaagucuu cuuccuggcg ggccucucgu cuccuuccug guuugggcgg | 1320 |
| aagccaucac cuggaugccu acgugggaag g | 1351 |

<210> SEQ ID NO 21
<211> LENGTH: 96
<212> TYPE: DNA
<213> ORGANISM: Homo sapiens

```
<220> FEATURE:
<223> OTHER INFORMATION: Core sequence of human Meg3

<400> SEQUENCE: 21
gcuucuugaa aggccugucu acacuugcug ucuuccuucc ucaccuccaa uuuccucuuc    60
aacccacugc uuccugacuc gcucuacucc guggaa                             96

<210> SEQ ID NO 22
<211> LENGTH: 18
<212> TYPE: DNA
<213> ORGANISM: Homo sapiens
<220> FEATURE:
<223> OTHER INFORMATION: Partial core sequence of human Meg3

<400> SEQUENCE: 22
ccugucuaca cuugcugu                                                 18

<210> SEQ ID NO 23
<211> LENGTH: 15
<212> TYPE: DNA
<213> ORGANISM: Artificial Sequence
<220> FEATURE:
<223> OTHER INFORMATION: GapmeR taget sequence in mouse Meg3

<400> SEQUENCE: 23
uacacucgcu gcuuu                                                    15

<210> SEQ ID NO 24
<211> LENGTH: 15
<212> TYPE: DNA
<213> ORGANISM: Artificial Sequence
<220> FEATURE:
<223> OTHER INFORMATION: GapmeR taget sequence in human Meg3

<400> SEQUENCE: 24
uacacuugcu gucuu                                                    15

<210> SEQ ID NO 25
<211> LENGTH: 20
<212> TYPE: DNA
<213> ORGANISM: Artificial Sequence
<220> FEATURE:
<223> OTHER INFORMATION: Mmu_Meg3 forward

<400> SEQUENCE: 25
tcacctccaa tttcccctcc                                               20

<210> SEQ ID NO 26
<211> LENGTH: 20
<212> TYPE: DNA
<213> ORGANISM: Artificial Sequence
<220> FEATURE:
<223> OTHER INFORMATION: Mmu_Meg3 reverse

<400> SEQUENCE: 26
gcaagccaag ccttaaacct                                               20

<210> SEQ ID NO 27
<211> LENGTH: 20
<212> TYPE: DNA
<213> ORGANISM: Artificial Sequence
<220> FEATURE:
<223> OTHER INFORMATION: Mmu_Hprt forward

<400> SEQUENCE: 27
```

```
gcgtcgtgat tagcgatgat                                                    20

<210> SEQ ID NO 28
<211> LENGTH: 21
<212> TYPE: DNA
<213> ORGANISM: Artificial Sequence
<220> FEATURE:
<223> OTHER INFORMATION: Mmu_Hprt reverse

<400> SEQUENCE: 28
tccttcatga catctcgagc a                                                  21

<210> SEQ ID NO 29
<211> LENGTH: 22
<212> TYPE: DNA
<213> ORGANISM: Artificial Sequence
<220> FEATURE:
<223> OTHER INFORMATION: Mmu_ActB forward

<400> SEQUENCE: 29
atcaagatca ttgctcctcc tg                                                 22

<210> SEQ ID NO 30
<211> LENGTH: 20
<212> TYPE: DNA
<213> ORGANISM: Artificial Sequence
<220> FEATURE:
<223> OTHER INFORMATION: Mmu_ActB reverse

<400> SEQUENCE: 30
agggtgtaaa acgcagctca                                                    20

<210> SEQ ID NO 31
<211> LENGTH: 23
<212> TYPE: DNA
<213> ORGANISM: Artificial Sequence
<220> FEATURE:
<223> OTHER INFORMATION: Mmu_Alpha-MHC forward

<400> SEQUENCE: 31
ggtccacatt cttcaggatt ctc                                                23

<210> SEQ ID NO 32
<211> LENGTH: 21
<212> TYPE: DNA
<213> ORGANISM: Artificial Sequence
<220> FEATURE:
<223> OTHER INFORMATION: Mmu_Alpha-MHC reverse

<400> SEQUENCE: 32
gcgttccttc tctgactttc g                                                  21

<210> SEQ ID NO 33
<211> LENGTH: 20
<212> TYPE: DNA
<213> ORGANISM: Artificial Sequence
<220> FEATURE:
<223> OTHER INFORMATION: Mmu_Fsp-1 forward

<400> SEQUENCE: 33
gctgcccaga taaggaaccc                                                    20

<210> SEQ ID NO 34
<211> LENGTH: 21
<212> TYPE: DNA
<213> ORGANISM: Artificial Sequence
```

```
<220> FEATURE:
<223> OTHER INFORMATION: Mmu_Fsp-1 reverse

<400> SEQUENCE: 34
tgcgaagaag ccagagtaag g                                            21

<210> SEQ ID NO 35
<211> LENGTH: 20
<212> TYPE: DNA
<213> ORGANISM: Artificial Sequence
<220> FEATURE:
<223> OTHER INFORMATION: Mmu_Gapdh forward

<400> SEQUENCE: 35
gaagggctca tgaccacagt                                              20

<210> SEQ ID NO 36
<211> LENGTH: 20
<212> TYPE: DNA
<213> ORGANISM: Artificial Sequence
<220> FEATURE:
<223> OTHER INFORMATION: Mmu_Gapdh reverse

<400> SEQUENCE: 36
ggatgcaggg atgatgttct                                              20

<210> SEQ ID NO 37
<211> LENGTH: 20
<212> TYPE: DNA
<213> ORGANISM: Artificial Sequence
<220> FEATURE:
<223> OTHER INFORMATION: Mmu_Xist forward

<400> SEQUENCE: 37
tcatccgctt gcgttcatag                                              20

<210> SEQ ID NO 38
<211> LENGTH: 24
<212> TYPE: DNA
<213> ORGANISM: Artificial Sequence
<220> FEATURE:
<223> OTHER INFORMATION: Mmu_Xist reverse

<400> SEQUENCE: 38
gagatcagtg ctggctaaat caga                                         24

<210> SEQ ID NO 39
<211> LENGTH: 21
<212> TYPE: DNA
<213> ORGANISM: Artificial Sequence
<220> FEATURE:
<223> OTHER INFORMATION: Mmu_Neat-1 forward

<400> SEQUENCE: 39
tggccccttt tgttcattag c                                            21

<210> SEQ ID NO 40
<211> LENGTH: 20
<212> TYPE: DNA
<213> ORGANISM: Artificial Sequence
<220> FEATURE:
<223> OTHER INFORMATION: Mmu_Neat-1 reverse

<400> SEQUENCE: 40
tggaaggcca ttgtttcagg                                              20
```

<210> SEQ ID NO 41
<211> LENGTH: 20
<212> TYPE: DNA
<213> ORGANISM: Artificial Sequence
<220> FEATURE:
<223> OTHER INFORMATION: Mmu_Anp forward

<400> SEQUENCE: 41
cctgtgtaca gtgcggtgtc                                               20

<210> SEQ ID NO 42
<211> LENGTH: 20
<212> TYPE: DNA
<213> ORGANISM: Artificial Sequence
<220> FEATURE:
<223> OTHER INFORMATION: Mmu_Anp reverse

<400> SEQUENCE: 42
cctagaagca ctgccgtctc                                               20

<210> SEQ ID NO 43
<211> LENGTH: 20
<212> TYPE: DNA
<213> ORGANISM: Artificial Sequence
<220> FEATURE:
<223> OTHER INFORMATION: Mmu_Bnp forward

<400> SEQUENCE: 43
ctgaaggtgc tgtcccagat                                               20

<210> SEQ ID NO 44
<211> LENGTH: 20
<212> TYPE: DNA
<213> ORGANISM: Artificial Sequence
<220> FEATURE:
<223> OTHER INFORMATION: Mmu_Bnp reverse

<400> SEQUENCE: 44
gttcttttgt gaggccttgg                                               20

<210> SEQ ID NO 45
<211> LENGTH: 20
<212> TYPE: DNA
<213> ORGANISM: Artificial Sequence
<220> FEATURE:
<223> OTHER INFORMATION: Mmu_Tgf-beta I forward

<400> SEQUENCE: 45
tcagacattc gggaagcagt                                               20

<210> SEQ ID NO 46
<211> LENGTH: 20
<212> TYPE: DNA
<213> ORGANISM: Artificial Sequence
<220> FEATURE:
<223> OTHER INFORMATION: Mmu_Tgf-beta I reverse

<400> SEQUENCE: 46
tgacgtcaaa agacagccac                                               20

<210> SEQ ID NO 47
<211> LENGTH: 20
<212> TYPE: DNA
<213> ORGANISM: Artificial Sequence
<220> FEATURE:
<223> OTHER INFORMATION: Mmu_Tgf-beta II forward

```
<400> SEQUENCE: 47
gcttcgaatc tggtgaaggc                                                   20

<210> SEQ ID NO 48
<211> LENGTH: 20
<212> TYPE: DNA
<213> ORGANISM: Artificial Sequence
<220> FEATURE:
<223> OTHER INFORMATION: Mmu_Tgf-beta II reverse

<400> SEQUENCE: 48
ctatcgatgt agcgctgggt                                                   20

<210> SEQ ID NO 49
<211> LENGTH: 20
<212> TYPE: DNA
<213> ORGANISM: Artificial Sequence
<220> FEATURE:
<223> OTHER INFORMATION: Mmu_Tgf-beta III forward

<400> SEQUENCE: 49
ccgctgaatg gctgtctttc                                                   20

<210> SEQ ID NO 50
<211> LENGTH: 20
<212> TYPE: DNA
<213> ORGANISM: Artificial Sequence
<220> FEATURE:
<223> OTHER INFORMATION: Mmu_Tgf-beta III reverse

<400> SEQUENCE: 50
ggctgaaagg tgtgacatgg                                                   20

<210> SEQ ID NO 51
<211> LENGTH: 15
<212> TYPE: DNA
<213> ORGANISM: Artificial Sequence
<220> FEATURE:
<223> OTHER INFORMATION: GapmeR-mouse Meg3

<400> SEQUENCE: 51
aaagcagcga gtgta                                                        15

<210> SEQ ID NO 52
<211> LENGTH: 15
<212> TYPE: DNA
<213> ORGANISM: Artificial Sequence
<220> FEATURE:
<223> OTHER INFORMATION: GapmeR negative control B

<400> SEQUENCE: 52
aacacgtcta tacgc                                                        15

<210> SEQ ID NO 53
<211> LENGTH: 19
<212> TYPE: DNA
<213> ORGANISM: Artificial Sequence
<220> FEATURE:
<223> OTHER INFORMATION: Mmu_Cdkn1a forward

<400> SEQUENCE: 53
cctggtgatg tccgacctg                                                    19

<210> SEQ ID NO 54
```

<211> LENGTH: 19
<212> TYPE: DNA
<213> ORGANISM: Artificial Sequence
<220> FEATURE:
<223> OTHER INFORMATION: Mmu_Cdkn1a reverse

<400> SEQUENCE: 54
ccatgagcgc atcgcaatc                                                  19

<210> SEQ ID NO 55
<211> LENGTH: 24
<212> TYPE: DNA
<213> ORGANISM: Artificial Sequence
<220> FEATURE:
<223> OTHER INFORMATION: Hsa_Mmp-2 forward

<400> SEQUENCE: 55
tgacatcaag ggcatttcag gagc                                            24

<210> SEQ ID NO 56
<211> LENGTH: 24
<212> TYPE: DNA
<213> ORGANISM: Artificial Sequence
<220> FEATURE:
<223> OTHER INFORMATION: Hsa_Mmp-2 reverse

<400> SEQUENCE: 56
gtccgccaaa tgaaccggtc cttg                                            24

<210> SEQ ID NO 57
<211> LENGTH: 20
<212> TYPE: DNA
<213> ORGANISM: Artificial Sequence
<220> FEATURE:
<223> OTHER INFORMATION: Hsa_Hprt forward

<400> SEQUENCE: 57
aggactgaac gtcttgctcg                                                 20

<210> SEQ ID NO 58
<211> LENGTH: 21
<212> TYPE: DNA
<213> ORGANISM: Artificial Sequence
<220> FEATURE:
<223> OTHER INFORMATION: Hsa_Hprt reverse

<400> SEQUENCE: 58
gtcccctgtt gactggtcat t                                               21

<210> SEQ ID NO 59
<211> LENGTH: 20
<212> TYPE: DNA
<213> ORGANISM: Artificial Sequence
<220> FEATURE:
<223> OTHER INFORMATION: Hsa_Meg3 forward

<400> SEQUENCE: 59
gaagaactgc ggatggaagc                                                 20

<210> SEQ ID NO 60
<211> LENGTH: 20
<212> TYPE: DNA
<213> ORGANISM: Artificial Sequence
<220> FEATURE:
<223> OTHER INFORMATION: Hsa_Meg3 reverse

<400> SEQUENCE: 60
cacgtaggca tccaggtgat                                               20

<210> SEQ ID NO 61
<211> LENGTH: 20
<212> TYPE: DNA
<213> ORGANISM: Artificial Sequence
<220> FEATURE:
<223> OTHER INFORMATION: Hsa_alpha-SMA forward

<400> SEQUENCE: 61
cctgactgag cgtggctatt                                               20

<210> SEQ ID NO 62
<211> LENGTH: 20
<212> TYPE: DNA
<213> ORGANISM: Artificial Sequence
<220> FEATURE:
<223> OTHER INFORMATION: Hsa_alpha-SMA reverse

<400> SEQUENCE: 62
gatgaaggat ggctggaaca                                               20

<210> SEQ ID NO 63
<211> LENGTH: 20
<212> TYPE: DNA
<213> ORGANISM: Artificial Sequence
<220> FEATURE:
<223> OTHER INFORMATION: Mmu_mmp2 promoter forward

<400> SEQUENCE: 63
tctccaactc tgttcaggca                                               20

<210> SEQ ID NO 64
<211> LENGTH: 20
<212> TYPE: DNA
<213> ORGANISM: Artificial Sequence
<220> FEATURE:
<223> OTHER INFORMATION: Mmu_mmp2 promoter reverse

<400> SEQUENCE: 64
tctggaaagg aggtgggatt                                               20

<210> SEQ ID NO 65
<211> LENGTH: 20
<212> TYPE: DNA
<213> ORGANISM: Artificial Sequence
<220> FEATURE:
<223> OTHER INFORMATION: Mmu_Cdkn1a promoter forward

<400> SEQUENCE: 65
gggtggggac tagctttctg                                               20

<210> SEQ ID NO 66
<211> LENGTH: 20
<212> TYPE: DNA
<213> ORGANISM: Artificial Sequence
<220> FEATURE:
<223> OTHER INFORMATION: Mmu_Cdkn1a promoter reverse

<400> SEQUENCE: 66
cagccccacc tcttcaattc                                               20

<210> SEQ ID NO 67
<211> LENGTH: 20
<212> TYPE: DNA

<213> ORGANISM: Artificial Sequence
<220> FEATURE:
<223> OTHER INFORMATION: Mmu_mmp2 intron forward

<400> SEQUENCE: 67
cgtggtgtct gaaacctgga                                         20

<210> SEQ ID NO 68
<211> LENGTH: 20
<212> TYPE: DNA
<213> ORGANISM: Artificial Sequence
<220> FEATURE:
<223> OTHER INFORMATION: Mmu_mmp2 intron reverse

<400> SEQUENCE: 68
cgccaggtta tgcgtctttg                                         20

<210> SEQ ID NO 69
<211> LENGTH: 20
<212> TYPE: DNA
<213> ORGANISM: Artificial Sequence
<220> FEATURE:
<223> OTHER INFORMATION: Mmu_Gapdh promoter forward

<400> SEQUENCE: 69
atcctgtagg ccaggtgatg                                         20

<210> SEQ ID NO 70
<211> LENGTH: 20
<212> TYPE: DNA
<213> ORGANISM: Artificial Sequence
<220> FEATURE:
<223> OTHER INFORMATION: Mmu_Gapdh promoter reverse

<400> SEQUENCE: 70
aggctcaagg gcttttaagg                                         20

<210> SEQ ID NO 71
<211> LENGTH: 16
<212> TYPE: DNA
<213> ORGANISM: Artificial Sequence
<220> FEATURE:
<223> OTHER INFORMATION: GapmeR-human Meg3 B

<400> SEQUENCE: 71
tgagcatagc aaaggt                                             16

<210> SEQ ID NO 72
<211> LENGTH: 16
<212> TYPE: DNA
<213> ORGANISM: Artificial Sequence
<220> FEATURE:
<223> OTHER INFORMATION: GapmeR-human Meg3 C

<400> SEQUENCE: 72
accaggaagg agacga                                             16

```
<210> SEQ ID NO 73
<211> LENGTH: 16
<212> TYPE: DNA
<213> ORGANISM: Artificial Sequence
<220> FEATURE:
<223> OTHER INFORMATION: GapmeR-human Meg3 E

<400> SEQUENCE: 73
ctttggaacc gcatca                                                    16
```

LNCRNA MEG3 FOR THERAPY AND DIAGNOSIS OF CARDIAC REMODELLING

The present invention relates to a compound inhibiting the expression and/or the activity of maternally expressed 3 (Meg3) for use in treating or preventing cardiac remodelling.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Large-scale analysis of mammalian transcriptomes uncovered that transcription of genomes leads to a complex proportion of RNA molecules of which only a small fraction serves as templates for protein synthesis. Several studies indicate that these non-coding RNAs (ncRNAs) have as important biological functions as their protein coding counterparts and suggest that altered expression or function of ncRNAs effects cardiovascular diseases, including cardiac diseases involving cardiac remodelling, such as cardiac hypertrophy and fibrosis, coronary artery disorders, as well as myocardial infarction.

The most reflected ncRNAs in cardiovascular research are microRNAs (miRNAs, miRs). These are endogenous, single-stranded RNAs composed of approximately 20-22 nucleotides that bind other transcripts reducing the stability and/or translation of their targets. For example, it was shown that miR-21 and miR-132 induce cardiac fibrosis or hypertrophy, respectively, and that in vivo repression of these miRNAs by specific AntagomiRs (being chemically engineered oligonucleotides silencing miRNAs) rescues fibrosis or hypertrophy in cardiac disease model of pressure-overload (Thum et al. Nature. 2008 456(7224):980-4; Ucar and Gupta et al. Nat Commun. 2012 3:1078). In another study it was found that miR-24 acts as a critical regulator of angiogenesis in ischemic heart disease (Fiedler et al. Circulation. 2011 124(6):720-30). Topkara and Mann (2011), Cardiovasc Drugs Ther.; 25(2):171-82 provides a review on the role of miRNAs in cardiac remodelling and heart failure.

More recent studies indicate that similar to miRNAs, long ncRNAs (lncRNAs) may also play an important role in various biological processes. LncRNAs are mRNA-like transcripts ranging from 200 nucleotides up to 100 kilobases and are classified based on their genomic distribution relative to protein-coding genes (sense to exons and/or introns, antisense, bidirectional, or intergenic). Several lncRNA transcripts are exclusively restricted to the nucleus, while others are also found in the cytoplasm. Here they interact with proteins as well as other RNA or DNA molecules enabling lncRNAs to influence a variety of gene regulatory mechanisms including chromatin modification, genomic imprinting, nuclear compartmentalization and architecture, as well as transcriptional and post-transcriptional regulation (Schonrock et al. Circ Res. 2012 Oct. 26; 111(10):1349-62; Caley et al. ScientificWorldJournal. 2010 10:90-102). Not surprisingly, lncRNAs are involved in human disease, such as cancer, metabolic and neuronal disorders.

However, little is known about their role in cardiovascular biology and in particular in cardiac disease. Recent studies indicated that the two lncRNAs Braveheart (Bvht) and FOXF1 adjacent non-coding developmental regulatory RNA (Fendrr) are required for the differentiation of cardiomyocytes and the development of lateral mesoderm tissue in the heart and body wall, respectively (Klattenhoff et al. Cell. 2013 152(3):570-83; Grote et al. Dev Cell. 2013 24(2):206-14). Both lncRNAs modulate the epigenetic profile of cells via an interaction with chromatin modifying complexes. Recent reports have also started to explore the role of lncRNAs in cardiovascular disease. Genome-wide association study (GWAS) identified single-nucleotide polymorphisms (SNPs) in loci encoding for the lncRNAs MIAT (myocardial infarction-associated transcript) or ANRIL (antisense noncoding RNA in the INK4 locus) that seem to be related to risk of myocardial infarction or coronary artery disease (Ishii et al. J Hum Genet. 2006 51(12):1087-99; McPherson et al. Science. 2007 316(5830):1488-91). The lncRNA Kcnq1ot1 controls the expression of its antisense gene Kcnq1 that encodes for a potassium channel. Since the potassium channel activity is essential for a normal cardiac performance, an altered regulation related by lncRNAs might lead to an abnormal heart function (Korostowski et al. PLoS Genet. 2012 8(9):e1002956). The circulating lncRNA LIPCAR can be used to predict survival in patients with heart failure (Kumarswamy et al. (2014), Circ Res.; 114 (10):1569-75). Moreover, the lncRNA Chast has been shown to promote cardiac remodelling (Viereck et al. (2016), Sci Transl Med.; 8(326):326ra22).

One of the main challenges in cardiac disease research is to identify novel and effective approaches to modulate gene networks or specific intracellular signaling pathways that may prove as effective therapeutic options themselves or have the potential to expand the efficiency of existing therapeutic strategies. The object of the present invention is therefore the provision of novel means and methods for treating or preventing cardiac diseases, in particular cardiac remodelling. It was surprisingly found in connection with the present invention that the lncRNA maternally expressed 3 (Meg3) plays a role in the development of cardiac remodelling thereby providing novel therapeutic and diagnostic strategies.

Accordingly the present invention relates in first aspect to a compound inhibiting the expression and/or the activity of maternally expressed 3 (Meg3) for use in treating or preventing cardiac remodelling.

The present invention also encompasses a method for treating or preventing cardiac remodelling in a patient in need thereof by administering to the patient a therapeutically effective amount of a compound inhibiting the expression and/or the activity of maternally expressed 3 (Meg3).

As used herein "maternally expressed 3 (Meg3)" (also known as GTL2; FP504; prebp1; PR00518; PRO2160; LINC00023; NCRNA00023; or onco-lncRNA-83) designates a maternally expressed, imprinted lncRNA (Zhang et al. (2010), Endocrinology 151(3) 939-47). The human MEG3 gene is found on chromosome 14q32.2 and the mouse Meg3 gene on the distal chromosome 12. The lncRNA Meg3 is known to act as a tumor suppressor (Zhang et al. (2003), J. Clin. Endocrinol. Metab. 88(11):5119-26). In more detail, Meg3 is expressed in many normal tissues, but its expression is lost in multiple cancer cell lines of various tissue origins. It inhibits tumor cell proliferation in vitro. It also interacts with the tumor suppressor p53, and regulates p53 target gene expression. Its deletion enhances angiogenesis in vivo. Meg3 is furthermore known to play an essential role in controlling pre- and postnatal growth and differentiation in mice and humans (Takahashi et al (2009), Hum. Molec. Genet., 18:1879-1888). In addition, Meg3 is involved in the senescence of endothelial cells (Boon (2015), Physiology, Proc Physiol Soc 34, SA022). Finally, reduced levels of Meg3 were detected in fibrotic liver of human and mouse (He et al. (2014), Biochim Biophys Acta, 1842(11):2204-15). However, to the best knowledge of the inventors the role of Meg3 in cardiac remodelling is disclosed for the first time by the present invention.

The term "ncRNA" or "non-coding RNA" as used herein designates a functional RNA molecule that is not translated into a protein. The DNA sequence from which a non-coding RNA is transcribed is often called in the art an RNA gene. The term "lncRNA" or "long non-coding RNA" is commonly used in the art and designates an ncRNA comprising more than 200 nucleotides. As will be further detailed herein below all known mouse and human Meg3 isoforms have more than 200 nucleotides. Meg3 is therefore an lncRNA.

A compound inhibiting the expression of Meg3 is in accordance with the present invention a compound lowering or preventing the transcription of the gene encoding the lncRNA Meg3. Such compounds include compounds interfering with the transcriptional machinery and/or its interaction with the promoter of said gene and/or with expression control elements remote from the promoter such as enhancers. The compound inhibiting the expression of Meg3 specifically inhibits the expression of said lncRNA, for example, by specifically interfering with the promoter region controlling the expression of the lncRNA. Preferably, the transcription of Meg3 is reduced by at least 50%, more preferred at least 75% such as at least 90% or 95%, even more preferred at least 98% and most preferred by about 100% (e.g., as compared to the same experimental set up in the absence of the compound).

A compound inhibiting the activity of Meg3 in accordance with the present invention causes said lncRNA to perform its function with lowered efficiency. The compound inhibiting the activity of Meg3 specifically inhibits the activity of said lncRNA. Preferably, the activity of Meg3 is reduced by at least 50%, more preferred at least 75% such as at least 90% or 95%, even more preferred at least 98%, and most preferably about 100% (e.g., as compared to the same experimental set up in the absence of the compound). Means and methods for determining the reduction of activity of an RNA are established in the art and are described, for example, in Esau et al. (2004), JBC, 279:52361-52365 or Gribbings et al. (2009), Nature Cell Biology 11, 1143-1149. A compound inhibiting the activity of Meg3 may be an antisense molecule, siRNA, shRNA, antibody, ribozyme, aptamer, or small molecule. These and other compounds will be further detailed herein below.

The efficiency of an inhibiting compound can be quantified by methods comparing the level of activity in the presence of the inhibitor to that in the absence of the inhibitor. For example, the change in the amount of Meg3 formed may be used in the measurement of its activity. As a further example, the change in the amount of MMP2 formed may be used in the measurement of its activity (noting that the downregulation of Meg3 is shown in the examples to be accompanied by the downregulation of MMP2). Such a method may be effected in high-throughput format in order to test the efficiency of several inhibiting compounds simultaneously. High-throughput assays, independently of being biochemical, cellular or other assays, generally may be performed in wells of microtiter plates, wherein each plate may contain 96, 384 or 1536 wells. Handling of the plates, including incubation at temperatures other than ambient temperature, and bringing into contact of test compounds with the assay mixture is preferably affected by one or more computer-controlled robotic systems including pipetting devices. In case large libraries of test compounds are to be screened and/or screening is to be effected within short time, mixtures of, for example 10, 20, 30, 40, 50 or 100 test compounds may be added to each well. In case a well exhibits the expected activity, said mixture of test compounds may be de-convoluted to identify the one or more test compounds in said mixture giving rise to said activity.

The compounds inhibiting the expression and/or the activity of Meg3 may be formulated as vesicles, such as liposomes. Liposomes have attracted great interest because of their specificity and the duration of action they offer from the standpoint of drug delivery. Liposomal delivery systems have been used to effectively deliver nucleic acids, such as siRNA in vivo into cells (Zimmermann et al. (2006) Nature, 441:111-114). Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are phagocytosed by macrophages and other cells in vivo.

The compounds inhibiting the expression and/or the activity of Meg3 can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgement of the ordinary clinician or physician. Generally, the regimen as a regular administration of the pharmaceutical composition should be in the range of 1 µg to 5 g units per day. However, a more preferred dosage is in the range of 0.01 mg to 100 mg, even more preferably 0.01 mg to 50 mg and most preferably 0.01 mg to 10 mg per day. Furthermore, if for example said compound comprises or is an nucleic acid molecule, such as an siRNA, the total pharmaceutically effective amount of pharmaceutical composition administered will typically be less than about 75 mg per kg of body weight, such as for example less than about 70, 60, 50, 40, 30, 20, 10, 5, 2, 1, 0.5, 0.1, 0.05, 0.01, 0.005, 0.001, or 0.0005 mg per kg of body weight. More preferably, the amount will be less than 2000 nmol of nucleic acid molecule per kg of body weight, such as for example less than 1500, 750, 300, 150, 75, 15, 7.5, 1.5, 0.75, 0.15, 0.075, 0.015, 0.0075, 0.0015, 0.00075 or 0.00015 nmol per kg of body weight.

The length of treatment needed to observe changes and the interval following treatment for responses to occur vary depending on the desired effect. The particular amounts may be determined by conventional tests which are well known to the person skilled in the art. Suitable tests are, for example, described in Tamhane and Logan (2002), "Multiple Test Procedures for Identifying the Minimum Effective and Maximum Safe Doses of a Drug", Journal of the American statistical association, 97(457):1-9.

The compounds inhibiting the expression and/or the activity of Meg3 are preferably admixed with a pharmaceutically acceptable carrier or excipient to form a pharmaceutical composition. By "pharmaceutically acceptable carrier or excipient" is meant a non-toxic solid, semisolid or liquid filler, diluent, encapsulating material or formulation auxiliary of any type (see also Handbook of Pharmaceutical Excipients 6ed. 2010, Published by the Pharmaceutical Press). The compounds inhibiting the expression and/or the activity of Meg3 or the pharmaceutical composition may be administered, for example, orally, parenterally, such as subcutaneously, intravenously, intramuscularly, intraperitoneally, intrathecally, transdermally, transmucosally, subdurally, locally or topically via iontophoresis, sublingually, by inhalation spray, aerosol or rectally and the like in dosage unit formulations optionally comprising conventional pharmaceutically acceptable carriers or excipients.

The term cardiac remodelling is defined herein as an alteration in the structure (e.g., dimensions, mass, shape) of the heart. Cardiac remodelling may occur in response to hemodynamic load and/or cardiac injury in association with neurohormonal activation. Remodelling may be described as physiologic or pathologic. For instance, pathologic (or unhealthy) cardiac remodelling is to be held distinct from physiologic (or healthy) cardiac remodelling (such cardiac remodelling or "athlete's heart") which is a normal response of the heart, for example, in response to healthy exercise or pregnancy. Among healthy subjects, rowers or cyclists tend to have the largest hearts, with an average left ventricular wall thickness of 1.3 centimeters, compared to 1.1 centimeters in average adults. Cardiac remodelling is in accordance with the invention unhealthy cardiac remodelling or pathological remodelling, such as cardiac remodelling in response to stress or disease, e.g., hypertension, heart muscle injury (myocardial infarction), heart failure or neurohormones. The remodelling process preferably includes increases in myocardial mass.

As can be taken from the examples herein below on a mouse model of pressure overload (i.e. TAC mice), the lncRNA Meg3 plays a role in the development of cardiac remodelling. In more detail, in the examples cardiac remodelling was induced in C57Bl/6N mice via transverse aortic constriction (TAC) and cardiac cells, including cardiac fibroblasts, were isolated from TAC and sham mice 13 weeks after surgery. LncRNA profiling in TAC and sham cardiac fibroblasts was performed through Arraystar's Mouse LncRNA Expression Microarray V2.0. Meg3 was identified among the most abundant lncRNAs in cardiac fibroblasts and the strongest regulated ones during pressure overload. Real-time PCR confirmed the downregulation of Meg3 in TAC fibroblasts, while no regulation was observed in cardiomyocytes or endothelial cells. Furthermore, expression levels of Meg3 in cardiomyocytes and endothelial cells of healthy mice represented, respectively, only 2% and 20% of the transcript levels found in cardiac fibroblasts of healthy mice. Meg3 expression in the heart seems to be dynamically regulated during the course of TAC, with upregulation occurring after 4 weeks of pressure overload and downregulation becoming evident only after 6 weeks. In cultured primary cardiac fibroblasts isolated from adult mice, Meg3 appears to be a nuclear lncRNA, strictly localized to the cell chromatin. Silencing of this lncRNA via transfection with antisense oligonucleotides (LNA GapmeRs, Exiqon) in mouse and human cardiac fibroblasts led to transcriptional regulation of several genes involved in cardiac remodelling, including cytokines, chemokines, growth factors and MMPs. In particular, in vitro silencing of Meg3 is accompanied by downregulation of MMP2 and inhibition of the TGF-beta-induced increase in MMP2 transcription. MMP2 deletion has been reported to ameliorate hypertrophy and fibrosis in a mouse model of TAC-induced cardiac remodelling, leading to improvement of diastolic function (Matsusaka H. et al. *Hypertension*. 2006 April; 47(4):711-7. Epub 2006 February 27). In the examples herein below, mice were subjected to 6 weeks of TAC and continuous silencing of Meg3 from week 1 until endpoint. Silencing was achieved via LNA GapmeRs and prevented the TAC-induced upregulation of MMP2, significantly reducing cardiac remodelling as evidenced by reduced cardiac fibrosis, reduced expression of pro-fibrotic molecules, decreased expression of hypertrophy markers and reduced cardiomyocytes cross-sectional area. Ejection fraction and fractional shortening were not affected by Meg3 levels; however, the left ventricular myocardial performance index measured via pulsed Doppler echocardiography revealed a functional improvement of the heart, with values of the index comparable to that of sham mice. Furthermore, pharmacological silencing of Meg3 in vivo did not lead to increased infiltration of inflammatory cells or increased MMP9 expression, which has been reported to occur in late cardiac remodelling stages, overtaking MMP2 levels and leading to heart failure (Giwimani S. et al. *Arch Physiol Biochem*. 2010 May; 116(2):63-72). It is also shown in the examples that silencing of Meg3 reduces LV mass following TAC and leads to a significantly better diastolic function without affecting cardiac contractility. Based on these experimental findings, it has been shown that silencing of Meg3 in the heart is a therapeutic approach for the treatment and prevention of cardiac remodeling.

In accordance with a preferred embodiment of the first aspect of the present invention, the cardiac remodelling is Heart Failure with preserved Ejection Fraction (HFpEF).

Heart Failure with preserved Ejection Fraction (HFpEF) (also referred to as diastolic heart failure) is commonly understood as manifestation of signs and symptoms of heart failure with a normal ejection fraction (>50%). HFpEF is characterized by cardiac remodelling, in particular a decrease in left ventricular compliance, leading to increased pressure in the left ventricle. Accordingly, concentric remodelling (with or without LV hypertrophy) is seen in many HFpEF patients. Also an increased left atrial size is often seen with HFpEF as a result of the poor left ventricular diastolic function. There is an increased risk for the development of congestive heart failure, atrial fibrillation, and pulmonary hypertension. Risk factors are hypertension, hyperlipidemia, diabetes, smoking, and obstructive sleep apnea. Morbidity and mortality in HFpEF patients are similar to values observed in patients with heart failure (HF) and reduced EF (i.e. HFrEF patients). However, so far no effective treatment has been identified for HFpEF (Borlaug and Paulus et al. (2014), Eur Heart J., 32(6):670-679). For this reason the treatment means and methods disclosed herein are of particular importance for HFpEF patients or patients being at risk of becoming HFpEF. The anti-MEG3 approach disclosed herein is apparently an ideal approach for the treatment and prevention of HFpEF.

In accordance with another preferred embodiment of the first aspect of the present invention, the cardiac remodelling is Heart Failure with reduced Ejection Fraction (HFrEF), myocardial infarction related cardiac remodelling, genetic cardiac disease associated cardiac remodelling, cardiac hypertrophy and/or cardiac fibrosis.

A direct effect of the inhibition of Meg3 on cardiac remodelling is demonstrated in the examples of this application on the basis of the well-established TAC mouse model for cardiac remodelling (Mei et al. (2006), Clin Exp Pharmacol Physiol.; 33(9):773-9.). As will be described in more detail in the following, all heart conditions listed in this preferred embodiment are associated with cardiac remodelling and therefore can be treated or prevented in accordance with the present invention by a compound inhibiting the expression and/or the activity of Meg3.

Heart Failure with reduced Ejection Fraction (HFrEF) (also referred to as systolic heart failure) is commonly understood as manifestation of signs and symptoms of heart failure with an ejection fraction less than 40%. HFrEF generally occurs when the left ventricle is dilated and enlarged with poor systolic function. Around 50% of HF patients have a HFpEF and around 50% of heart failure patients have a HFrEF. Just as HfpEF, HFrEF is characterized by cardiac remodelling, in particular a decrease in left ventricular compliance, leading to increased pressure in the left ventricle.

Myocardial infarction (MI) is commonly known as a heart attack. MI occurs when blood flow stops to a part of the heart causing damage to the heart muscle. After an MI typically postinfarction cardiac remodelling is observed. In more detail, the acute loss of myocardium caused by the MI results in an abrupt increase in loading conditions that induces a unique pattern of remodelling involving the infarcted border zone and remote noninfarcted myocardium. Myocyte necrosis and the resultant increase in load trigger a cascade of biochemical intracellular signaling processes that initiates and subsequently modulates reparative changes, which include dilatation, hypertrophy, and the formation of a discrete collagen scar. In particular, ventricular remodelling may continue for weeks or months after the MI until the distending forces are counterbalanced by the tensile strength of the collagen scar. The postinfarction cardiac remodelling after MI is referred to herein as "myocardial infarction related cardiac remodelling".

A genetic (or inherited) cardiac disease is caused by changes in genes that are passed from generation to generation. Many different types of heart diseases can be inherited. Examples include conditions that affect the heart muscle, called inherited cardiomyopathies, such as hypertrophic cardiomyopathy, dilated cardiomyopathy, Morbus Fabry disease, amyloidoses and arrhythmogenic right ventricular cardiomyopathy. These examples also involve cardiac remodelling. Specific examples of genetic cardiac diseases which are associated with cardiac remodelling include but are not limited to hereditary hypertrophic cardiomyopythies (such as familial hypertrophic cardiomyopathy) or Morbus Fabry disease.

Cardiac hypertrophy is defined as an increase in size of the heart without any increase in myocyte number. This results in a thickening of the heart walls. Pathological cardiac hypertrophy occurs in response to haemodynamic overload due to different forms of stress, such as hypertension, valve disease, and myocardial infarction (MI). Prolonged hypertrophic growth of the heart results in cardiac arrhythmias, heart failure and may lead to sudden death (Frey and Olso (2003), Annu Rev Physiol; 65: 45-79). Thus, cardiac hypertrophy is in accordance with the invention unhealthy cardiac hypertrophy (or pathological hypertrophy), such as cardiac hypertrophy in response to stress or disease, e.g., hypertension, heart muscle injury (myocardial infarction), heart failure or neurohormones.

Fibrosis, in general, is a scarring process which is characterized by fibroblast proliferation and excess deposition of extracellular matrix (ECM) proteins, which leads to distorted organ architecture and function. Cardiac fibrosis thus refers to the proliferation of fibroblasts and an excess deposition of ECM proteins (in particular collagen) in the cardiac muscle. The proliferation of the fibroblasts generally leads to abnormal thickening of the heart, in particular the heart valves. The fibrotic ECM causes increased stiffness and induces pathological signaling within cardiomyocytes resulting in progressive cardiac failure. Also, the excessive ECM impairs mechano-electric coupling of cardiomyocytes and increases the risk of arrhythmias. Fibroblasts are principally responsible for deposition of the excessive fibrotic ECM and activated fibroblasts may directly cause hypertrophy of cardiomyocytes via paracrine mechanisms further contributing to impaired cardiac function (Krenning et al. (2010), J Cell Physiol; 225(3):631-637).

In accordance with a more preferred embodiment of the first aspect of the present invention, the cardiac hypertrophy is ventricular hypertrophy, preferably left ventricular hypertrophy, and/or the cardiac fibrosis is ventricular fibrosis, preferably left ventricular fibrosis.

Most cases of cardiac hypertrophies as well as most cases of cardiac fibrosis affect the heart ventricles. Although left ventricular hypertrophy and fibrosis is more common, cardiac hypertrophy and fibrosis can also occur in the right ventricle or both ventricles. The ventricles are the chambers in the heart responsible for pumping blood either to the lungs (right ventricle) or to the rest of the body (left ventricle).

In accordance with a further preferred embodiment of the first aspect of the present invention, Meg3 comprises or consists of a nucleic acid sequence selected from the group consisting of SEQ ID NOs 1 to 21.

The term "nucleic acid sequence" or "nucleotide sequence", in accordance with the present invention, includes DNA and RNA. SEQ ID NOs 1 to 21 are sequences of the lncRNA Meg3 and therefore single-stranded RNA sequences. As will be further detailed herein below, nucleotide-based compounds inhibiting the expression of Meg3 may comprise DNA sequences (e.g. LNA GapmeRs) or RNA sequences (e.g. siRNAs). As will be also further detailed herein below, nucleotide-based compounds inhibiting the expression of Meg3 may be single stranded (e.g. LNA GapmeRs) or double-stranded (e.g. siRNAs). The term "nucleic acid sequence" is interchangeably used in accordance with the invention with the term "polynucleotide sequence". Short "nucleic acid sequence" are also referred to herein as "oligonucleotide sequences". Oligonucleotide sequences are less than 50 nucleotides in length, preferably less than 40 nucleotides and most preferably less than 30 nucleotides.

In human at least 12 different isoforms of MEG3 are generated by alternative splicing (Zhang et al. (2010), Endocrinology; 151(3):939-947). Also in mouse multiple isoforms of Meg3 were found (Schuster-Gossler et al. (1998), Dev Dyn; 212(2):214-28). Herein, SEQ ID NOs 1 to 7 represent the so far known seven different isoforms of mouse Meg3 (designated herein mouse Meg3 isoforms 1 to 7). All seven mouse isoforms share the core sequence of SEQ ID NO: 8 which core sequence corresponds to exon 5 of the mouse Meg3 gene. SEQ ID NOs 9 to 20 represent the known twelve different isoforms of human Meg3 (designated herein human Meg3 isoforms 1 to 12). All twelve human isoforms share the core sequence of SEQ ID NO: 21 which core sequence corresponds to exon 5 of the human Meg3 gene. The core sequences of mouse and human Meg3 is evolutionarily highly conserved with a sequence identity of 89%. It is accordingly preferred that Meg3 comprises the nucleic acid sequence of SEQ ID NO: 8 or SEQ ID NO: 21, and more preferably comprises the human Meg3 core sequence of SEQ ID NO: 21. SEQ ID NOs 1 to 7 and 9 to 20 comprise sequences of more than 200 nucleotides; i.e. sequences ranging from 706 to 14548 nucleotides. SEQ ID NOs 1 to 7 and 9 to 20 are therefore lncRNAs.

In accordance with a yet further preferred embodiment of the first aspect of the present invention, the compound inhibiting the expression and/or the activity of Meg3 is a small molecule inhibitor, a nucleotide-based inhibitor or an amino acid-based inhibitor.

A small molecule inhibitor is a low molecular weight organic compound which is by definition not a polymer. The small molecule of the invention is a molecule that binds with high affinity to Meg3 and in addition inhibits the activity of Meg3. The upper molecular weight limit for a small molecule is preferably 1500 Da, more preferably 1000 Da and most preferably 800 Da which allows for the possibility to rapidly diffuse across cell membranes so that they can reach intracellular sites of action. Libraries of small organic molecules and high-throughput techniques for screening such libraries with a specific target molecule, in the present case the lncRNA Meg3, and preferably a polynucleotide selected from the group consisting of SEQ ID NOs 1 to 21. Within SEQ ID NOs 1 to 21, SEQ ID NOs 8 and 21 are preferred and SEQ ID NO: 21 is most preferred. By targeting the mouse Meg3 core sequence of SEQ ID NO: 8 it is possible to inhibit all known mouse Meg3 isoforms and by targeting the human Meg3 core sequence of SEQ ID NO: 21 it is possible to inhibit all known human Meg3 isoforms. Given the sequence homology of 89% of SEQ ID NOs 8 and 21 it may also be possible to target mouse and human Meg3 isoforms by a single small molecule inhibitor.

A nucleotide-based inhibitor comprises or consists of a nucleic acid sequence. The nucleic acid is preferably complementary to a nucleic acid sequence of at least 12 contiguous nucleotides of one or more of SEQ ID NOs 1 to 21. Within SEQ ID NOs 1 to 21, SEQ ID NOs 8 and 21 are preferred and SEQ ID NO: 21 is most preferred. The nucleotide-based inhibitor may comprise or consist of RNA, DNA or both. The nucleotide-based inhibitor of the invention is a molecule that binds specifically to Meg3 and in addition inhibits the activity of Meg3. As used herein specific binding means that the inhibitor specifically targets the lncRNA Meg3 and does substantially not exert any off target inhibitory effects, in particular on other cellular nucleic acid molecules. It is to be understood that a nucleotide-based inhibitor specifically binding to SEQ ID NO: 8 is capable of inhibiting all known mouse Meg3 isoforms and a nucleotide-based inhibitor specifically binding to SEQ ID NO: 21 is capable of specifically inhibiting all known human Meg3 isoforms. Given the sequence homology of 89% of SEQ ID NOs 8 and 21 it may also be possible to select or design a nucleotide-based inhibitor specifically inhibiting the mouse and human Meg3 isoforms.

An amino acid-based inhibitor comprises or consists of an amino acid sequence and preferably an amino acid sequence of at least 25, more preferably at least 50 amino acids. The amino acid-based inhibitor of the invention is a molecule that binds specifically to Meg3 and in addition inhibits the activity of Meg3. The amino acid-based inhibitor preferably comprises natural amino acids but may also comprise unnatural amino acids. The amino acid-based inhibitor is preferably selected or designed such that it specifically binds to a nucleic acid sequence selected from one or more of SEQ ID NOs 1 to 21. Within SEQ ID NOs 1 to 21, SEQ ID NOs 8 and 21 are preferred and SEQ ID NO: 21 is most preferred. An amino acid-based inhibitor specifically binding to SEQ ID NO: 8 is capable of specifically inhibiting all known mouse Meg3 isoforms and an amino acid-based inhibitor specifically binding to SEQ ID NO: 21 is capable of specifically inhibiting all known human Meg3 isoforms. Given the sequence homology of 89% of SEQ ID NOs 8 and 21 it may also be possible to select or design an amino acid-based inhibitor specifically inhibiting the mouse and human Meg3 isoforms.

In accordance with a yet further preferred embodiment of the first aspect of the present invention, the nucleotide-based inhibitor is an aptamer, a ribozyme, a siRNA, a shRNA or an antisense oligonucleotide (such as a LNA-GapmeR, an Antagomir, or an antimiR) and the amino acid-based inhibitor is an antibody or a protein drug.

The aptamer, ribozyme, antibody, protein drug, siRNA, a shRNA or an antisense oligonucleotide of this embodiment specifically bind to Meg3, thereby inhibiting the activity of Meg3.

The term "aptamer" in accordance with the present invention refers to DNA or RNA molecules being either in the natural D-conformation or in the L-conformation ("spiegelmer") that have been selected from random pools based on their ability to bind other molecules.

Aptamers have been selected which bind nucleic acid, proteins, small organic compounds, and even entire organisms. A database of aptamers is maintained at http://aptamer.icmb.utexas.edu/. More specifically, aptamers can be classified as DNA or RNA aptamers or peptide aptamers. Whereas the former consist of (usually short) strands of oligonucleotides, the latter consist of a short variable peptide domain, attached at both ends to a protein scaffold. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. The molecular target envisaged by the present invention is a nucleic acid, namely the lncRNA Meg3. Hence, aptamers can be produced against the target molecule of the invention. Aptamers offer the utility for biotechnological and therapeutic applications as they offer molecular recognition properties that rival those of the commonly used biomolecules, in particular antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Non-modified aptamers are cleared rapidly from the bloodstream, with a half-life of minutes to hours, mainly due to nuclease degradation and clearance from the body by the kidneys, a result of the aptamer's inherently low molecular weight. The rapid clearance of aptamers can be an advantage in applications such as in vivo diagnostic imaging. Several modifications, such as 2'-fluorine-substituted pyrimidines, polyethylene glycol (PEG) linkage, etc. are available to scientists with which the half-life of aptamers easily can be increased to the day or even week time scale.

The term "ribozymes" refers to RNA molecules that act as enzymes in the absence of proteins. These RNA molecules act catalytic or autocatalytic and are capable of cleaving e.g. other RNAs at specific target sites but they have also been found to catalyze the aminotransferase activity of the ribosome. Selection of appropriate target sites and corresponding ribozymes can be done as described for example in Zaher and Unrau (2007), RNA, 13 (7): 1017-1026. Examples of well-characterized small self-cleaving RNAs are the hammerhead, hairpin, hepatitis delta virus, and in vitro-selected lead-dependent ribozymes. The organization of these small catalysts is in contrast to that of larger ribozymes, such as the group I intron. The principle of catalytic self-cleavage has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it appears that catalytic sequences for almost any target sequence can be created, provided the target sequence contains a potential matching cleavage site. The basic principle of constructing hammerhead ribozymes is as follows: An interesting region of the RNA, which contains the GUC (or CUC) triplet, is selected. Two oligonucleotide strands, each with 6 to 8 nucleotides, are taken and the catalytic hammerhead sequence is inserted between them. Molecules of this type were synthesized for numerous target sequences. They showed catalytic activity in vitro and in some cases also in vivo. The best results are usually obtained with short ribozymes and target sequences. Since the target sequence is in accordance with the present invention a RNA sequence, Meg3 is a bona fide target for the generation of ribozymes being capable to specifically cleave Meg3.

The aptamers and ribozymes may comprise modified nucleotides, such as locked nucleic acids (LNAs).

The term "antibody" as used in accordance with the present invention comprises, for example, polyclonal or monoclonal antibodies. Furthermore, also derivatives or fragments thereof, which still retain the binding specificity, are comprised in the term "antibody". Antibody fragments or derivatives comprise, inter alia, Fab or Fab' fragments, Fd, F(ab')$_2$, Fv or scFv fragments, single domain $V_H$ or V-like domains, such as VhH or V-NAR-domains, as well as multimeric formats such as minibodies, diabodies, tribodies, tetrabodies or chemically conjugated Fab'-multimers (see, for example, Altshuler et al., Biochemistry (Mosc). 2010 December; 75(13):1584-605, Holliger and Hudson, Nat Biotechnol., 2005; 23(9):1126-36). The term "antibody" also includes embodiments such as chimeric (human constant domain, non-human variable domain), single chain and humanized (human antibody with the exception of non-human CDRs) antibodies. Various techniques for the production of antibodies and fragments thereof are well known in the art and described, e.g. in Altshuler et al., Biochemistry (Mosc). 2010 December; 75(13):1584-605. Thus, polyclonal antibodies can be obtained from the blood of an animal following immunisation with an antigen in mixture with additives and adjuvans and monoclonal antibodies can be produced by any technique which provides antibodies produced by continuous cell line cultures. Examples for such techniques are described, e.g. Harlow and Lane, Antibodies: A Laboratory Manual, Cold Spring Harbor Laboratory Press, 1988 and Harlow and Lane, Using Antibodies: A Laboratory Manual, Cold Spring Harbor Laboratory Press, 1999 and include the hybridoma technique originally described by Köhler and Milstein, Nature 256 (1975), 495-497, the trioma technique, the human B-cell hybridoma technique (see e.g. Kozbor, Immunology Today 4 (1983), 72; Milstein, C (1999), BioEssays 21 (11): 966-73) and the EBV-hybridoma technique to produce human monoclonal antibodies (Cole et al., Monoclonal Antibodies and Cancer Therapy, Alan R. Liss, Inc. (1985), 77-96). Furthermore, recombinant antibodies may be obtained from monoclonal antibodies or can be prepared de novo using various display methods such as phage, ribosomal, mRNA, or cell display. A suitable system for the expression of the recombinant (humanized) antibodies or fragments thereof may be selected from, for example, bacteria, yeast, insects, mammalian cell lines or transgenic animals or plants (see, e.g., U.S. Pat. No. 6,080,560; Holliger and Hudson, Nat Biotechnol., 2005; 23(9):1126-36). Further, techniques described for the production of single chain antibodies (see, inter alia, U.S. Pat. No. 4,946,778) can be adapted to produce single chain antibodies specific for the target of this invention. Surface plasmon resonance as employed in the BIAcore system can be used to increase the efficiency of phage antibodies.

The term "protein drug" designates designer drugs that are derivatives of human proteins. These proteins are used as scaffold to create a protein drug by well-established screening procedures (see Tomlinson et al (2004), Nature Biotechnology, 22(5): 521-522). Non-limiting examples of human proteins which serve as a scaffold for designing protein drugs are transferrin, C-type lectins, trinectins, domain antibodies, kunitz domains, lipocalins and the Fyn SH3 domain.

The antisense technology for the downregulation of RNA is well-established and widely used in the art to treat various diseases. The basic idea of the antisense technology is the use of oligonucleotides for silencing a selected target RNA through the exquisite specificity of complementary-based pairing (Re, Ochsner J. 2000 October; 2(4): 233-236). Herein below details on the antisense construct compound classes of siRNAs, shRNAs and antisense oligonucleotides will be provided. As will be further detailed herein below, antisense oligonucleotides are single stranded antisense constructs while siRNAs and shRNAs are double stranded antisense constructs with one strand comprising an antisense oligonucleotide sequence being (i.e. the so-called antisense strand). All these compound classes may be used to achieve downregulation or inhibition of a target RNA.

In accordance with the present invention the target of antisense constructs in general as well as all the specific classes of antisense constructs being described herein is the lncRNA Meg3. Accordingly, the target is preferably a nucleic acid sequence selected from one or more of SEQ ID NOs 1 to 21. Within SEQ ID NOs 1 to 21 SEQ ID NOs 8 and 21 are preferred and SEQ ID NO: 21 is most preferred. By targeting SEQ ID NO: 8 it is possible to downregulate all known mouse Meg3 isoforms and by targeting SEQ ID NO: 21 it is possible to downregulate all known human Meg3 isoforms. Given the sequence homology of 89% of SEQ ID NOs 8 and 21 it may also be possible to target mouse and human Meg3 isoforms by a single antisense construct.

With respect to SEQ ID NO: 21 as well as with respect to SEQ ID NOs 9 to 20 (which comprise the core sequence of SEQ ID NO: 21) it is furthermore preferred that the antisense construct does not target the part of SEQ ID NO: 21 being shown in the 18 nucleotides of SEQ ID NO: 22 or a subsequence of SEQ ID NO: 22. The part of the human Meg3 core sequence as show in SEQ ID NO: 22 is 100% identical to the DNM3 opposite strand/antisense RNA, the miRNA 3120 and the miRNA 214. Hence, in case the target is SEQ ID NO: 22 or a subsequence thereof off target effects cannot be excluded. A partial overlap of the complementary nucleic acid sequence of or comprised by an antisense construct with SEQ ID NO: 22 is generally acceptable as long as specific inhibition of Meg3 without off target effects is achieved. It is a matter of routine in the field of antisense technology to design an antisense construct with a sufficient number of nucleotide mismatches to any off target in order to ensure that no off targets become downregulated.

The term "siRNA" in accordance with the present invention refers to small interfering RNA, also known as short interfering RNA or silencing RNA. siRNAs are a class of 12 to 30, preferably 18 to 30, more preferably 20 to 25, and most preferred 21 to 23 or 21 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome. siRNAs have a well defined structure: a short double-strand of RNA (dsRNA), advantageously with at least one RNA strand having an overhang. Each strand typically has a 5' phosphate group and a 3' hydroxyl (—OH) group. This structure is the result of processing by dicer, an enzyme that converts either long dsRNAs or small hairpin RNAs into siRNAs. siRNAs can also be exogenously (artificially) introduced into cells to bring about the specific knockdown of a gene of interest. Thus, any gene of which the sequence is known can in principle be targeted based on sequence complementarity with an appropriately tailored siRNA. The double-stranded RNA molecule or a metabolic processing product thereof is capable of mediating target-specific nucleic acid modifications, particularly RNA interference and/or DNA methylation. Also preferably at least one RNA strand has a 5'- and/or 3'-overhang. Preferably, one or both ends of the double-strand have a 3'-overhang from 1-5 nucleotides, more preferably from 1-3 nucleotides and most preferably 2 nucleotides. In general, any RNA molecule suitable to act as siRNA is envisioned in the present invention. The most efficient silencing was so far obtained with siRNA duplexes composed of 21-nt sense and 21-nt antisense strands, paired in a manner to have 2-nt 3'-overhangs. The sequence of the 2-nt 3' overhang makes a small contribution to the specificity of target recognition restricted to the unpaired nucleotide adjacent to the first base pair (Elbashir et al. Nature. 2001 May 24; 411(6836):494-8). 2'-deoxynucleotides in the 3' overhangs are as efficient as ribonucleotides, but are often cheaper to synthesize and probably more nuclease resistant. The siRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO. For instance, with respect to SEQ ID NOs 9 to 21 it is furthermore preferred that the antisense construct does not target the subsequence SEQ ID NO: 22 or a subsequence thereof.

A preferred example of a siRNA is an Endoribonuclease-prepared siRNA (esiRNA). An esiRNA is a mixture of siRNA oligos resulting from cleavage of a long double-stranded RNA (dsRNA) with an endoribonuclease such as Escherichia coli RNase III or dicer. esiRNAs are an alternative concept to the usage of chemically synthesized siRNA for RNA Interference (RNAi). For the generation of esiRNAs a cDNA of an lncRNA template may be amplified by PCR and tagged with two bacteriophage-promotor sequences. RNA polymerase is then used to generate long double stranded RNA that is complentary to the target-gene cDNA. This complentary RNA may be subsequently digested with RNase III from Escherichia coli to generate short overlapping fragments of siRNAs with a length between 18-25 base pairs. This complex mixture of short double stranded RNAs is similar to the mixture generated by dicer cleavage in vivo and is therefore called endoribonuclease-prepared siRNA or short esiRNA. Hence, esiRNA are a heterogeneous mixture of siRNAs that all target the same mRNA sequence. esiRNAs lead to highly specific and effective gene silencing.

A "shRNA" in accordance with the present invention is a short hairpin RNA, which is a sequence of RNA that makes a (tight) hairpin turn that can also be used to silence gene expression via RNA interference. shRNA preferably utilizes the U6 promoter for its expression. The shRNA hairpin structure is cleaved by the cellular machinery into siRNA, which is then bound to the RNA-induced silencing complex (RISC). This complex binds to and cleaves mRNAs which match the shRNA that is bound to it. The shRNA according to the invention comprises an antisense strand which comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO. For instance, with respect to SEQ ID NOs 9 to 21 it is furthermore preferred that the antisense construct does not target the subsequence SEQ ID NO: 22 or a subsequence thereof.

The term "antisense oligonucleotide" in accordance with the present invention refers to a single-stranded nucleotide sequence being complementary by virtue of Watson-Crick base pair hybridization to the lncRNA Meg3 whereby the activity of Meg3 is blocked. The antisense oligonucleotides may be unmodified or chemically modified. In general, they are relatively short (preferably between 13 and 25 nucleotides). Moreover, they are specific for Meg3, i.e. they hybridize to a unique sequence in the total pool of targets present in the target cells/organism. The antisense oligonucleotide according to the invention comprises or consists a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO. For instance, with respect to SEQ ID NOs 9 to 21 it is furthermore preferred that the antisense construct does not target the subsequence SEQ ID NO: 22 or a subsequence thereof.

The antisense oligonucleotide is preferably a LNA-GapmeR, an Antagomir, or an antimiR.

LNA-GapmeRs or simply GapmeRs are potent antisense oligonucleotides used for highly efficient inhibition of mRNA and lncRNA function. GapmeRs function by RNase H dependent degradation of complementary RNA targets. They are an excellent alternative to siRNA for knockdown of mRNA and lncRNA. They are advantageously taken up by cell without transfection reagents. GapmeRs contain a central stretch of DNA monomers flanked by blocks of LNAs. The GapmeRs are preferably 14-16 nucleotides in length and are optionally fully phosphorothioated. The DNA gap activates the RNAse H-mediated degradation of targeted RNAs and is also suitable to target transcripts directly in the nucleus. The LNA-GapmeR according to the invention comprises a sequence which is with increasing preference complementary to at least 13 nucleotides, at least 14 nucleotides, or at least 15 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 13 nucleotides, at least 14 nucleotides, or at least 15 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO. For instance, with respect to SEQ ID NOs 9 to 21 it is furthermore preferred that the antisense construct does not target the subsequence SEQ ID NO: 22 or a subsequence thereof. A LNA-GapmeR targeting the mouse Meg3 nucleotides of SEQ ID NO: 23 is used in the below examples of the present application to downregulate the lncRNA Meg3. SEQ ID NO: 24 shows the human Meg3 nucleotides corresponding to the mouse Meg3 nucleotides of SEQ ID NO: 23. Accordingly, the LNA-GapmeR according to the invention comprises more preferably a sequence which is complementary to SEQ ID NO: 23 or SEQ ID NO: 24, and most preferably to SEQ ID NO: 24. In the below examples the three anti-human Meg3 LNA-GapmeRs of SEQ ID NOs 71, 72 and 73 are used to downregulate the lncRNA Meg3 in human cardiac fibroblasts. Accordingly, the LNA-GapmeR according to the invention also comprises most preferably a sequence of any one of SEQ ID NOs 71 to 73. Among SEQ ID NOs 71 to 73 SEQ ID NO: 71 is most preferred. The LNA-GapmeR technology is well established. LNA-GapmeRs are routinely designed using established algorithms. LNA-GapmeRs to a selected target are commercially available including positive and negative controls, for example, from Exiqon.

As mentioned, AntimiRs are oligonucleotide inhibitors that were initially designed to be complementary to a miRNA. AntimiRs against miRNAs have been used extensively as tools to gain understanding of specific miRNA functions and as potential therapeutics. As used herein, the AntimiRs are designed to be complementary to the lncRNA Meg3. AntimiRs are preferably 14 to 23 nucleotides in length. An AntimiR according to the invention more preferably comprises or consists a sequence which is with increasing preference complementary to at least 15 nucleotides, at least 16 nucleotides, at least 17 nucleotides, at least 18 nucleotides, at least 19 nucleotides, at least 20 nucleotides, at least 21 nucleotides, at least 22 nucleotides, or at least 23 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 15 nucleotides, at least 16 nucleotides, at least 17 nucleotides, at least 18 nucleotides, at least 19 nucleotides, at least 20 nucleotides, at least 21 nucleotides, at least 22 nucleotides, or at least 23 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO.

AntimiRs are preferably AntagomiRs. AntagomiRs are synthetic 2-0-methyl RNA oligonucleotides, preferably of 21 to 23 nucleotides which are preferably fully complementary to the selected target RNA. While AntagomiRs were initially designed against miRNAs they may also be designed against lncRNAs. The AntagomiRs according to the invention therefore preferably comprises a sequence being complementary to 21 to 23 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These 21 to 23 nucleotides are preferably complementary to a contiguous part of one or more selected from SEQ ID NOs 1 to 21 including the preferred target sequences within SEQ ID NOs 1 to 21 described herein above, i.e. the nucleotides are consecutive in the respective SEQ ID NO. AntagomiRs are preferably synthesized with 2'-OMe modified bases (2'-hydroxyl of the ribose is replaced with a methoxy group), phosphorothioate (phosphodiester linkages are changed to phosphorothioates) on the first two and last four bases, and an addition of cholesterol motif at 3' end through a hydroxyprolinol modified linkage. For instance, with respect to SEQ ID NOs 9 to 21 it is furthermore preferred that the antisense construct does not target the subsequence SEQ ID NO: 22 or a subsequence thereof. The addition of 2'-OMe and phosphorothioate modifications improve the bio-stability whereas cholesterol conjugation enhances distribution and cell permeation of the AntagomiRs.

Antisense molecules (including antisense oligonucleotides, such as LNA-GapmeR, an Antagomir, an antimiR), siRNAs and shRNAs of the present invention are preferably chemically synthesized using a conventional nucleic acid synthesizer. Suppliers of nucleic acid sequence synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK).

The ability of antisense molecules (including antisense oligonucleotides, such as LNA-GapmeR, an Antagomir, an antimiR), siRNA, and shRNA to potently, but reversibly, silence or inhibit a lncRNA in vivo makes these molecules particularly well suited for use in the pharmaceutical composition of the invention. Ways of administering siRNA to humans are described in De Fougerolles et al., Current Opinion in Pharmacology, 2008, 8:280-285. Such ways are also suitable for administering other small RNA molecules like antisense oligonucleotides or shRNAs. Accordingly, such pharmaceutical compositions may be administered directly formulated as a saline, via liposome based and polymer-based nanoparticle approaches, as conjugated or complexation pharmaceutical compositions, or via viral delivery systems. Direct administration comprises injection into tissue, intranasal and intratracheal administration. Liposome based and polymer-based nanoparticle approaches comprise the cationic lipid Genzyme Lipid (GL) 67, cationic liposomes, chitosan nanoparticles and cationic cell penetrating peptides (CPPs). Conjugated or complexation pharmaceutical compositions comprise PEI-complexed antisense molecules (including antisense oligonucleotides), siRNA, or shRNA. Further, viral delivery systems comprise influenza virus envelopes and virosomes.

The antisense molecules (including antisense oligonucleotides, such as LNA-GapmeR, an Antagomir, an antimiR), siRNAs, shRNAs may comprise modified nucleotides such as locked nucleic acids (LNAs). The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides.

In accordance with a further preferred embodiment of the first aspect of the invention the nucleotide-based inhibitor comprises (a) a nucleic acid sequence which comprises or consists of a nucleic acid sequence being complementary to at least 12 continuous nucleotides of a nucleic acid sequence selected from SEQ ID NOs 1 to 21, (b) a nucleic acid sequence which comprises or consists of a nucleic acid sequence which is at least 70% identical to the complementary strand of one or more nucleic acid sequences selected from SEQ ID NOs 1 to 21, (c) a nucleic acid sequence which comprises or consists of a nucleic acid sequence according to (a) or (b), wherein the nucleic acid sequence is DNA or RNA, (d) an expression vector expressing the nucleic acid sequence as defined in any one of (a) to (c), preferably under the control of a heart-specific promoter and/or a fibroblast-specific promoter, or (e) a host comprising the expression vector of (d).

The nucleic acid sequences as defined in items (a) to (c) of this preferred embodiment comprise or consist of sequences being complementary to nucleotides of the Meg3 as defined by one or more of SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. Hence, the nucleic acid sequences as defined in items (a) to (c) comprise or are antisense nucleic acid sequences.

The nucleic acid sequence according to item (a) of this further preferred embodiment of the invention comprises or consists of a sequence which is with increasing preference complementary to at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides of one or more selected from SEQ ID NOs 1 to 21 including the preferred target sequences within SEQ ID NOs 1 to 21 described herein above. For instance, with respect to SEQ ID NOs 9 to 21 it is furthermore preferred that the antisense construct does not target the subsequence SEQ ID NO: 22 or a subsequence thereof. These at least 13 nucleotides, at least 14 nucleotides, at least 15 nucleotides, at least 16 nucleotides, at least 17 nucleotides, at least 18 nucleotides, at least 19 nucleotides, at least 20 nucleotides, or at least 21 nucleotides are preferably a contiguous part of one or more selected from SEQ ID NOs 1 to 21 including the preferred target sequences within SEQ ID NOs 1 to 21 described herein above, i.e. the nucleotides are consecutive in the respective SEQ ID NO. For instance, with respect to SEQ ID NOs 9 to 21 it is furthermore preferred that the antisense construct does not target the subsequence SEQ ID NO: 22 or a subsequence thereof. The format of the nucleic acid sequence according to item (a) is not particularly limited as long as it comprises or consists of at least 12 continuous nucleotides being complementary to a nucleic acid sequence selected from SEQ ID NOs 1 to 21. The nucleic acid sequence according to item (a) comprises or consists of antisense an oligonucleotide. Hence, the nucleic acid sequence according to item (a) reflects the above-mentioned basic principle of the antisense technology which is the use of an oligonucleotide for silencing a selected target RNA through the exquisite specificity of complementary-based pairing. Therefore, it is to be understood that the nucleic acid sequence according to item (a) is preferably in the format of an siRNA, shRNA or an antisense oligonucleotide as defined herein above. The antisense oligonucleotides are preferably LNA-GapmeRs, AntagomiRs, or antimiRs as defined herein above.

The nucleic acid sequence according to item (b) requiring at least 70% identity to the complementary strand of one or more nucleic acid sequences selected from SEQ ID NOs 1 to 21 is considerably longer than the nucleic acid sequence according to item (a) which comprises an antisense oligonucleotide and comprises at least 12 continuous nucleotides of a nucleic acid sequence selected from SEQ ID NOs 1 to 21. Among SEQ ID NOs 1 to 21 SEQ ID NO: 21 is the shortest sequence and SEQ ID NO: 21 comprises 96 nucleotides. A sequence of at least 70% identity to the complementary strand of SEQ ID NO: 21 accordingly has to comprise at least 68 nucleotides. A nucleic acid sequence according to item (b) of the above preferred embodiment of the invention is capable of interacting with, more specifically hybridizing with the target lncRNA Meg3. By formation of the hybrid the function of the lncRNA Meg3 is reduced or blocked.

The sequence identity of the molecule according to item (b) in connection with a sequence selected from SEQ ID NOs 1 to 21 is with increasing preference at least 75%, at least 80%, at least 85%, at least 90%, at least 92.5%, at least 95%, at least 98%, at least 99% and 100%. Within SEQ ID NOs 1 to 21 SEQ ID NOs 8 and 21 are preferred and SEQ ID NO: 21 is most preferred. The sequence identity in connection with each of SEQ ID NOs 1 to 21 can be individually selected. For instance, a non-limiting example is at least 90% in connection with SEQ ID NO: 8 and at least 95% in connection with SEQ ID NO: 21. Means and methods for determining sequence identity are known in the art. Preferably, the BLAST (Basic Local Alignment Search Tool) program is used for determining the sequence identity with regard to one or more of SEQ ID NOs 1 to 21. Most preferred examples of nucleic acid sequences which comprise a nucleotide sequence which is at least 70% identical to the complementary strand of one or more of SEQ ID NOs 1 to 21 are the complementary strands of SEQ ID NO: 8 and/or 21.

In the nucleic acid sequence according to item (c) the nucleotide sequences may be RNA or DNA. RNA or DNA encompasses chemically modified RNA nucleotides or DNA nucleotides. As commonly known RNA comprises the nucleotide U while DNA comprises the nucleotide T.

In accordance with items (d) and (e) of the above preferred embodiment the inhibitor may also be an expression vector or host, respectively being capable of producing an nucleic acid sequence as defined in any one of items (a) to (c).

An expression vector may be a plasmid that is used to introduce a specific transcript into a target cell. Once the expression vector is inside the cell, the protein that is encoded by the gene is produced by the cellular-transcription and translation machinery ribosomal complexes. The plasmid is in general engineered to contain regulatory sequences that act as enhancer and/or promoter regions and lead to efficient transcription of the transcript. In accordance with the present invention the expression vector preferably contains a heart-specific promoter and/or a fibroblast-specific promoter. Heart-specific promoters are known in the art, for example, from Boecker at al. (2004), Mol Imagin.; 3(2):69-75. Using a heart-specific promoter ensures that the nucleic acid sequence is only expressed in the heart and may avoid potential unwanted side effects by expression in other organs. Promoters for fibroblast-specific expression are as well known in the art, e.g., from Takeda et al (2010), J Ciin Invest. 2010; 120(1):254-265 or Hemmings et al. (2014), Heart; 100:A19-A20. Using a fibroblast-specific promoter ensures that the nucleic acid sequence is only expressed in fibroblasts and may avoid potential unwanted side effects by expression in other cell-types, such as endothelial cells. The fibroblast-specific promoter described in Takeda et al (2010), loc. lit. is in particular specific for heart fibroblasts. Accordingly, also promoters being heart-specific and a fibroblast-specific are known and are most preferably used as a promoter in the context of the present invention. This is because such a promoter may avoid potential unwanted side effects by expression in other organs as well as in other cell-types.

Non-limiting examples of expression vectors include prokaryotic plasmid vectors, such as the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, pLXIN, pSIR (Clontech), pIRES-EGFP (Clontech), pEAK-10 (Edge Biosystems) pTriEx-Hygro (Novagen) and pClNeo (Promega). Examples for plasmid vectors suitable for Pichia pastoris comprise e.g. the plasmids pAO815, pPIC9K and pPIC3.5K (all Intvitrogen). For the formulation of a pharmaceutical composition a suitable vector is selected in accordance with good manufacturing practice. Such vectors are known in the art, for example, from Ausubel et al, Hum Gene Ther. 2011 April; 22(4):489-97 or Allay et al., Hum Gene Ther. May 2011; 22(5): 595-604.

A typical mammalian expression vector contains the promoter element, which mediates the initiation of transcription of mRNA, the protein coding sequence, and signals required for the termination of transcription and polyadenylation of the transcript. Moreover, elements such as origin of replication, drug resistance gene, regulators (as part of an inducible promoter) may also be included. The lac promoter is a typical inducible promoter, useful for prokaryotic cells, which can be induced using the lactose analogue isopropylthiol-b-D-galactoside ("IPTG"). For recombinant expression and secretion, the polynucleotide of interest may be ligated between e.g. the PelB leader signal, which directs the recombinant protein in the periplasm and the gene III in a phagemid called pHEN4 (described in Ghahroudi et al, 1997, FEBS Letters 414:521-526). Additional elements might include enhancers, Kozak sequences and intervening sequences flanked by donor and acceptor sites for RNA splicing. Highly efficient transcription can be achieved with the early and late promoters from SV40, the long terminal repeats (LTRs) from retroviruses, e.g., RSV, HTLVI, HIVI, and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109).

Alternatively, the recombinant (poly)peptide can be expressed in stable cell lines that contain the gene construct integrated into a chromosome. The co-transfection with a selectable marker such as dhfr, gpt, neomycin, hygromycin allows the identification and isolation of the transfected cells. The transfected nucleic acid can also be amplified to express large amounts of the encoded (poly)peptide. The DHFR (dihydrofolate red uctase) marker is useful to develop cell lines that carry several hundred or even several thousand copies of the gene of interest. Another useful selection marker is the enzyme glutamine synthase (GS) (Murphy et al. 1991, *Biochem J.* 227:277-279; Bebbington et al. 1992, *Bio/Technology* 10:169-175). Using these markers, the mammalian cells are grown in selective medium and the cells with the highest resistance are selected. As indicated above, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. For vector modification techniques, see Sambrook and Russel (2001), Molecular Cloning: A Laboratory Manual, 3 Vol. Generally, vectors can contain one or more origins of replication (ori) and inheritance systems for cloning or expression, one or more markers for selection in the host, e.g., antibiotic resistance, and one or more expression cassettes. Suitable origins of replication (ori) include, for example, the Col E1, the SV40 viral and the M 13 origins of replication.

The sequences to be inserted into the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, promoters, enhancers, and/or insulators), internal ribosomal entry sites (IRES) (Owens, Proc. Natl. Acad. Sci. USA 98 (2001), 1471-1476) and optionally poly-A signals ensuring termination of transcription and stabilization of the transcript. Additional regulatory elements may include transcriptional as well as translational enhancers, and/or naturally-associated or heterologous promoter regions. Preferably, the nucleotide sequence as defined in item (a) of the above preferred embodiment of the invention is operatively linked to such expression control sequences allowing expression in prokaryotic or eukaryotic cells.

The host may be a prokaryotic or eukaryotic cell. A suitable eukaryotic host may be a mammalian cell, an amphibian cell, a fish cell, an insect cell, a fungal cell or a plant cell. Representative examples of bacterial cells are *E. coli*, Streptomyces and Salmonella typhimurium cells; of fungal cells are yeast cells; and of insect cells are Drosophila S2 and Spodoptera Sf9 cells. It is preferred that the cell is a mammalian cell such as a human cell. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells. The cell may be a part of a cell line, preferably a human cell line. Appropriate culture mediums and conditions for the above-described host cells are known in the art. The host is preferably a host cell and more preferably an isolated host cell. The host is also preferably a non-human host.

In a second aspect the present invention relates to a method for diagnosing cardiac remodelling in a patient, comprising (a) detecting the expression level of Meg3 in a sample obtained from said patient, and optionally (b) comparing said expression obtained in (a) with the expression level of Meg3 in a sample obtained from at least one healthy subject or with a predetermined standard that has been obtained from a sample of at least one healthy subject, wherein a greater than 2-fold downregulation of Meg3 is indicative for cardiac remodelling in the patient.

Also in connection with the second aspect of the present invention the cardiac remodelling is preferably Heart Failure with preserved Ejection Fraction (HFpEF) and/or is preferably Heart Failure with reduced Ejection Fraction (HFrEF), myocardial infarction related cardiac remodelling, genetic cardiac disease associated cardiac remodelling, cardiac hypertrophy and/or cardiac fibrosis. The cardiac hypertrophy is preferably ventricular hypertrophy, more preferably left ventricular hypertrophy, and/or the cardiac fibrosis is preferably ventricular fibrosis, more preferably left ventricular fibrosis.

Moreover, also in connection with the second aspect of the present invention Meg3 preferably comprises or consists of a nucleic acid sequence selected from the group consisting of SEQ ID NOs 1 to 21. Within SEQ ID NOs 1 to 21 SEQ ID NO: 8 and SEQ ID NO: 21 are preferred and SEQ ID NO: 21 is most preferred. By detecting SEQ ID NO: 8 all mouse Meg3 isoforms may be detected simultaneously and by detecting SEQ ID NO: 21 all human Meg3 isoforms may be detected simultaneously. In this connection it is to be understood that the method according to the second aspect of the invention may also encompass detecting and comparing the expression level of one or more lncRNAs being with increased preference at least 90%, at least 92%, at least 94%, at least 96%, at least 98%, at least 99%, and at least 99.5% identical to any one of SEQ ID NOs 1 to 21. The method according to the second aspect of the invention may furthermore encompass detecting and comparing the expression level of one or more lncRNAs differing with increasing preference by no more than 10, such as 5, 4, 3, 2 or 1 nucleotide(s) from any one of SEQ ID NOs 1 to 21. The nucleotide differences may be the addition, deletion and/or substitution of nucleotide(s). The sequences the expression of which is compared, while being homologous, may also differ from each other with increasing preference by no more than 10, such as 5, 4, 3, 2 or 1 nucleotide(s).

The term "sample" designates a tissue sample or a body fluid sample. The body fluid sample is preferably selected from blood, serum, plasma, urine, salvia, amniotic fluid, cerebrospinal fluid and lymph. The tissue sample is preferably an organ sample, preferably a heart sample. As far as the method is applied to a body fluid sample it is to be understood that the expression level of the lncRNA Meg3 corresponds to the concentration of the lncRNA Meg3, because lncRNAs are not directly expressed in the body fluid but secreted from the cells, said cells expressing the lncRNAs, into the body fluids.

The "patient" or "subject" referred to herein is preferably human.

The term "detecting the expression level of Meg3" means determining the amount or yield of Meg3. Meg3 is initially expressed within a cell, in particular a heart fibroblast. It was found in accordance with the present invention that the lncRNA Meg3 can be detected in the sample of a patient, in particular a heart tissue sample. Meg3 being "expressed in a sample" is therefore Meg3 whose expression level can be detected in the sample by means and methods being further detailed herein below. Meg3 is downregulated in a test sample if the amount or yield of the Meg3 is significantly less as compared to the amount or yield of Meg3 in a control sample.

In accordance with the above described diagnostic method the control sample is either a sample obtained from at least one healthy subject or a predetermined standard that has been obtained from a sample of at least one healthy subject. A healthy subject in particular a healthy subject with no heart condition can be routinely identified by a physician. The at least one healthy subject is with increasing preference at least two, at least three, at least five, and at least ten healthy subjects. By employing more than one healthy subject individual Meg3 expression level differences may be balanced. With respect to the use of a predetermined standard it is noted that within the context of the diagnostic method of the invention is not or not always necessary to determine the Meg3 expression level in a sample of at least one healthy subject. Once Meg3 expression levels obtained from a sample of at least one healthy subject are available they may be used in the diagnostic method of the invention as a predetermined standard.

The expression level in the samples can be quantified by any suitable means and methods available from the art. In general relative and absolute quantification means and methods can be used. In absolute quantification no known standards or controls are needed. The expression level can be directly quantified. As well-known in the art, absolute quantification may rely on a predetermined standard curve. In relative quantification the expression level is quantified relative to a reference (such as known control expressions levels). Also in the absence of controls, one can relatively quantify the expression level when comparing e.g. fluorescence intensities.

Methods to assess RNA concentration may, for example, comprise measuring the fluorescence intensity of dyes that bind to nucleic acids and selectively fluoresce when bound. Such methods comprise a reverse transcription reaction and the production of cDNA, wherein the amount of the cDNA is determined thereby indirectly determining the amount of the RNA. The fluorescent-based method is particularly useful for cases where the RNA concentration is too low to accurately assess some with spectrophotometry and/or in cases where contaminants absorbing at 260 nm make accurate quantification by spectrophotometry difficult or impossible.

When comparing the expression level of a lncRNA between different samples reliability of the comparison is preferably improved by including an invariant endogenous control (expression of a reference gene) to correct for potential sample to sample variations. Such normalization with respect to an invariant endogenous control is routinely performed in the art. For example, means and methods for expression level normalization, e.g. in real-time RT-PCR (see, for example, Bustin, Journal of Molecular Endocrinology, (2002) 29, 23-39) or micro-array expression analysis (see, for example, Calza and Balwitan, Methods Mol Biol. 2010; 673:37-52) are well-established. Also methods for normalization of the expression levels of small RNA sequences are established (see, for example, Mestdagh et al. (2009) Genome Biol.; 10(6):R64). In case RT-PCR or a micro-array is used to determine the expression levels in accordance with the present invention, the expression levels are preferably normalized to a spiked-in RNA (see, for example, McCormick et al. (2011), Silence, 2:2). Known amounts of a spiked-in RNA are mixed with the sample during preparation. More preferably the RNA is externally spiked-in to the sample before the RNA isolation process is carried out. The spiked-in RNA technology is well-known and commercial kits are available from a number of manufacturers. The spiked-in RNA is preferably a spiked-in *C. elegans* RNA.

In the examples herein below the primer pair of SEQ ID NOs 25 and 26 was employed in order to detect the expression level of mouse Meg3 and the primer pair of SEQ ID NOs 59 and 60 was employed in order to detect the expression level of human Meg3, wherein the uneven number is the forward primer and the even number is the reverse primer. One of these primer pairs is preferably used in the diagnostic method according to the second aspect of the invention. One of these primer pairs is likewise preferably incorporated into the kit of the invention being described herein below.

The greater than 2-fold downregulation is with increasing preference greater than 3-fold downregulation, greater than 4-fold downregulation, greater than 5-fold downregulation, greater than 6-fold downregulation, greater than 7-fold downregulation and greater than 8-fold downregulation. The higher thresholds for the downregulation may increase the reliability of the method of the second aspect of the invention.

As discussed in greater detail herein above, it is shown in the examples that Meg3 expression in the course of TAC is downregulated 6 weeks after the pressure overload and thereafter. From the $6^{th}$ week onward also cardiac remodelling occurs as an adaptive response of the heart to the induced pressure overload. For this reason it can be expected that an at least 2-fold downregulation of Meg3 expression in a test patient as compared to Meg3 expression of at least one healthy subject or a predetermined standard that has been obtained from a sample of at least one healthy subject is indicative for cardiac remodelling. Measuring Meg3 expression levels is thus expected to be useful for diagnosing cardiac remodelling.

In accordance with a preferred embodiment of the second aspect of the present invention the sample is a heart tissue sample. In accordance with a more preferred embodiment of the second aspect of the present invention the heart tissue sample comprises or consists of cardiac fibroblasts. In accordance with an even more preferred embodiment of the second aspect of the present invention the heart tissue sample comprises or is the chromatin fraction of heart tissue.

As can be taken from the examples herein below downregulation of Meg3 is exemplified in a heart tissue sample, in particular in the cardiac fibroblasts of such sample. In the context of the below described examples it was also determined that the lncRNA Meg3 can be found in the chromatin fraction of heart tissue.

In accordance with a further preferred embodiment of the second aspect of the invention the detection of the expression level of Meg3 comprises (a) quantitative PCR, preferably quantitative real time PCR, or (b) a template/RNA amplification method followed by determining the expression level of Meg3 using a fluorescence- or luminescence-based quantification method.

In quantitative PCR (qPCR), the amount of amplified product is linked to fluorescence intensity using a fluorescent reporter molecule. The point at which the fluorescent signal is measured in order to calculate the initial template quantity can either be at the end of the reaction (endpoint semi-quantitative PCR) or while the amplification is still progressing (real-time qPCR).

In endpoint semi-quantitative PCR, fluorescence data are collected after the amplification reaction has been completed, usually after 30-40 cycles, and this final fluorescence is used to back-calculate the amount of template present prior to PCR.

The more sensitive and reproducible method of real-time qPCR measures the fluorescence at each cycle as the amplification progresses. This allows quantification of the template to be based on the fluorescence signal during the exponential phase of amplification, before limiting reagents, accumulation of inhibitors, or inactivation of the polymerase have started to have an effect on the efficiency of amplification. Fluorescence readings at these earlier cycles of the reaction will measure the amplified template quantity where the reaction is much more reproducible from sample to sample than at the endpoint.

A non-limiting example of a template/RNA amplification method followed by determining the expression level of the lncRNA Meg3 using a fluorescence- or luminescence-based quantification method is a method combining transcription mediated amplification (TMA) and a hybridization protection assay (HPA). In more detail, such a method may comprise hybridizing one or more oligonucleotides ("capture oligonucleotides") that are complementary to Meg3. The hybridized target sequences are then captured onto magnetic microparticles that are separated from the sample in a magnetic field. Wash steps may be utilized to remove extraneous components. Target amplification typically occurs via TMA, which is a transcription-based nucleic acid amplification method that utilizes two enzymes, Moloney murine leukemia virus (MMLV) reverse transcriptase and T7 RNA polymerase. A unique set of primers is used for Meg3, preferably the primer pair of SEQ ID NOs 25 and 26 or a primer pair of SEQ ID NOs 59 and 60. The reverse transcriptase is used to generate a DNA copy (containing a promoter sequence for T7 RNA polymerase) of the target sequence. T7 RNA polymerase produces multiple copies of RNA amplicon from the DNA copy. Detection of Meg3 expression level is achieved by HPA using single-stranded, chemiluminescent-labelled nucleic acid probes that are complementary to the one or more amplicon. Preferably, distinguishably labelled probes are used for each target amplicon. The labelled nucleic acid probes hybridize specifically to the amplicon. A "selection reagent" then differentiates between hybridized and unhybridized probes by inactivating the label on unhybridized probes. During the detection step, the chemiluminescent signal produced by the hybridized probe is measured in a luminometer and is reported as "Relative Light Units" (RLU), thereby quantifying the Meg3 expression level.

In accordance with a further preferred embodiment of the second aspect of the invention the method comprises prior to the detection of the expression level of Meg3 a pre-amplification step of the RNA within the test patient's sample and/or the healthy patient's sample.

Performing a pre-amplification step is of particular advantage in case only a low amount of (test and/or control) sample is available. The pre-amplification step allows increasing the amount of RNA within the sample before proceeding to the analysis of the expression level. Means and methods for the pre-amplification of RNA are well known in the art (see, e.g., Vermeulen et al (2009) BMC Res Notes., 2:235). In case both the RNA in the test and control sample is pre-amplified preferably the same method for the pre-amplification step is used such that the relative amount of RNA of the test sample as compared to the control sample is maintained. In case only the RNA of the test or control sample is pre-amplified or the two RNA samples are pre-amplified by different methods, the expression level data may have to be normalized for the pre-amplification step; see, e.g. Mestdagh et al. (2009), *Genome Biology* 2009, 10:R64.

In a third aspect the present invention relates to a kit for diagnosing cardiac remodelling in a patient, said kit comprising means for the detection of the expression level of Meg3, and instructions how to use the kit.

The instructions how to use the kit preferably inform inter alia that a low-expression level of the lncRNAs Meg3 is indicative for cardiac remodelling.

The means for the detection of the expression level of Meg3 are preferably the means required for (i) a quantitative PCR, preferably quantitative real time PCR, or (ii) a template/RNA amplification method followed by determining the expression level of Meg3 using a fluorescence- or luminescence-based quantification method. These means have been further detailed herein above in connection with the second aspect of the invention, and may be comprised in the kit. Hence, the means preferably comprise oligonucleotides, such as fluorescent hybridization probes or primers, which specifically hybridize to Meg3. Additional ingredients of the kits may be fluorescent or luminescent dyes, preferably coupled to said oligonucleotides. Also, additional ingredients of the kits may be enzymes, such as a reverse transcriptase and/or a polymerase.

Also in connection with the third aspect of the invention, Meg3 preferably comprises or consists of a nucleic acid sequence selected from the group consisting of SEQ ID NOs 1 to 21. Within SEQ ID NOs 1 to 21 SEQ ID NO: 8 and SEQ ID NO: 21 are preferred and SEQ ID NO: 21 is most preferred. In this connection it is to be understood that the kits may also encompass means for detecting lncRNAs being with increased preference at least 90%, at least 92%, at least 94%, at least 96%, at least 98%, at least 99%, and at least 99.5% identical to any one of SEQ ID NOs 1 to 21. The kit may furthermore encompass means for detecting and comparing the expression level of one or more lncRNAs differing with increasing preference by no more than 10, such as 5, 4, 3, 2 or 1 nucleotide(s) from any one of SEQ ID NOs 1 to 21. The nucleotide differences may be the addition, deletion and/or substitution of nucleotide(s).

The various components of the kit may be packaged in one or more containers such as one or more vials. The vials may, in addition to the components, comprise preservatives or buffers for storage.

In accordance with a preferred embodiment of the third aspect of the invention the means are primer pairs used for the specific detection of the expression level of Meg3.

The primer pairs of SEQ ID NOs 25 and 26, and SEQ ID NOs 59 and 60 are described herein above in connection with the method according to the second aspect of the present invention. One of these primer pairs is preferably incorporated into the kit of the invention as means for the detection of the expression level of Meg3.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a majority of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show.

FIG. 1. A) Meg3 levels were measured via qPCR in 13 weeks TAC vs sham CFs (cardiac fibroblasts), cardiomyocytes (CMCs) and endothelial cells (ECs), revealing that Meg3 downregulation after TAC is fibroblast-specific. B) Furthermore, in healthy mice Meg3 is mainly expressed in fibroblasts rather than cardiomyocytes or endothelial cells. (HPRT was used as normalizing control in both figures; ****p<0.0001; n=5).

FIG. 2. A) Subcellular localization of Meg3 was investigated after cell lysis and isolation of the cytoplasmic, nuclear and chromatin-associated RNA content, revealing that, in CFs, Meg3 is nuclear enriched and associated to the chromatin. Known mRNAs and lncRNAs (b-actin, Xist, Neat1) were used as controls. (n=3). B) Antisense oligonucleotides (GapmeRs, Exiqon) were used to silence Meg3 expression in CFs. (p<0.01, ***p<0.001, n=8/9 replicates from 3 independent experiments).

FIG. 3. A) The effect of Meg3 silencing on gene expression was investigated in CFs through microarray profiling 48 h after transfection with Meg3 antisense GapmeR or a negative control (n=3, FC≥2/≤0.5, p≤0.05). B) The functional annotation tool David 6.7 has been used to perform the GO term enrichment analysis. Top 5 terms according to p-values are shown for the search domains molecular function, biological process and cellular compartment.

FIG. 4. A) Silencing of Meg3 leads to downregulation of MMP2, under basal conditions, 48 h after transfection with antisense GapmeRs. Also, the TGF-beta I-induced increase in MMP2 transcription is abolished when expression of Meg3 is knocked down. (*p<0.05, **p<0.01, n=6/9 replicates from 2/3 independent experiments). B) Gelatinolytic activity of MMP2 in the supernatant of cardiac fibroblasts is reduced after silencing of Meg3. (*p<0.05, n=6 replicates from 2 independent experiments).

FIG. 5. Expression of Meg3 and MMP2 in murine myocardial tissue in the course of TAC (n=3/7/8).

FIG. 6. A) One GapmeR injection at a dose of 20 mg/Kg was followed 5 days later by isolation of cardiomyocytes, endothelial cells and CFs. As shown, Meg3 expression is silenced in fibroblasts and endothelial cells, while no effect was observed in cardiomyocytes (n=2/3). B) TAC operation was followed by injection of Meg3 antisense GapmeR or GapmeR Control 1 week after surgery. 20 mg/Kg GapmeR injections were repeated at 10 days intervals. Animals were sacrificed 6 weeks after TAC.

FIG. 7. A) Meg3 and Mmp2 expression in myocardial tissues of mice undergoing 6 weeks of TAC with or without inhibition of Meg3 (n=7/8; p<0.01, **p<0.0001). B) Expression of TGF-beta isoforms and CTGF (n=7/8; *p<0.05, ***p<0.001; p-values represent statistically significant differences between TAC groups and the sham group). C) Fibrosis levels in the left ventricles, as assessed via picro Sirius staining of heart sections (n=7/8; *p<0.05, *p<0.001). D) Cardiomyocyte cross sectional areas in myocardial tissues of mice undergoing 6 weeks of TAC with or without inhibition of Meg3 (n=7/8; p<0.01, *p<0.001, **p<0.0001).

Figure 8:
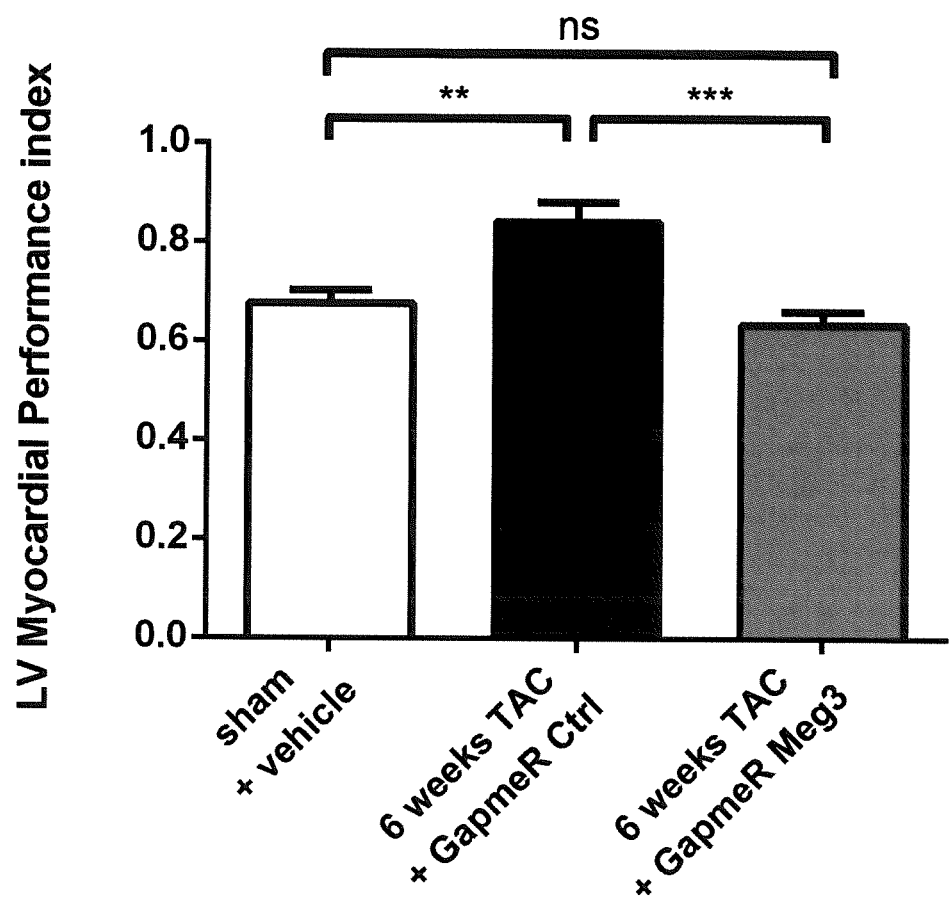

FIG. 8. Silencing of Meg3 shortly after TAC is associated to a significantly better myocardial performance with shorter isovolumetric contraction and relaxation times, indicative of a better systolic and dyastolic function. (n=7/8; p<0.01, *p<0.001, ****p<0.0001).

FIG. 9. Silencing of Meg3 shortly after TAO is not associated to increased mmp9 expression or enhanced infiltration of inflammatory cells. (n=7/8; *p<0.05).

FIG. 10. Silencing of Meg3 prevents binding of P53 on the promoter of Mmp-2 (a) Genomic position and nucleotide composition of the P53 binding site on the Mmp-2 promoter as predicted by the Jaspar database. (b) ChIP confirming the binding of P53 to the Mmp-2 promoter following stimulation of mouse CFs with TGF-β I and the absence of binding following Meg3 silencing; the promoter of Cdkn1a (p21) has been used as positive control, whereas an intron of Mmp-2 and the promoter of Gapdh have been used as negative controls (n=4), since they are not predicted to be bound by P53. (FC=fold change, *p≤0.05, p≤0.01, * p≤0.001, ****p≤0.0001, ns=not significant).

FIG. 11. Effect of Meg3 silencing on apoptosis and cell cycle distribution of murine CFs (a) Expression of Cdkn1a (P21) in mouse CFs 48 hours after transfection with GapmeR Meg3 or GapmeR Control as measured via qPCR (n=3). (b) Apoptosis levels, represented by the activity of the effector caspases 3/7 in CFs following Meg3 silencing in the absence (PBS) and in the presence (doxorubicin) of DNA damage (n=3). (c) Cell cycle distribution of AMCFs 48 hours after transfection with GapmeRs (n=3). (FC=fold change, ****p≤0.0001, ns=not significant).

Figure 12:
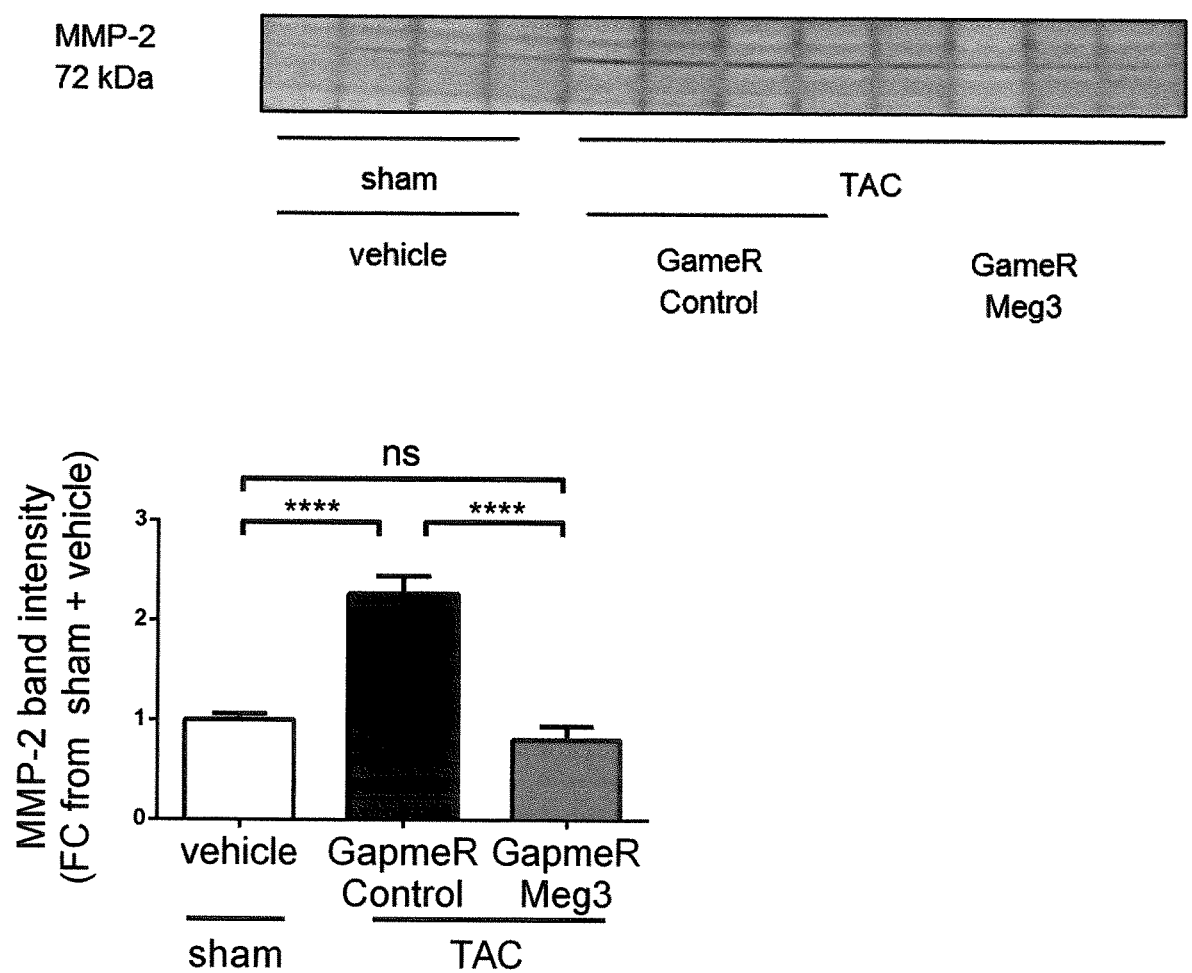

FIG. 12. MMP-2 gelatinolytic bands in the hearts of sham and TAC mice injected with GapmeRs. Representative gel picture where the originally white bands on a blue zymogram background have been grey-scaled and inverted for a better visualization (n=7/8). (FC=fold change, ****p≤0.0001, ns=not significant).

Figure 13:
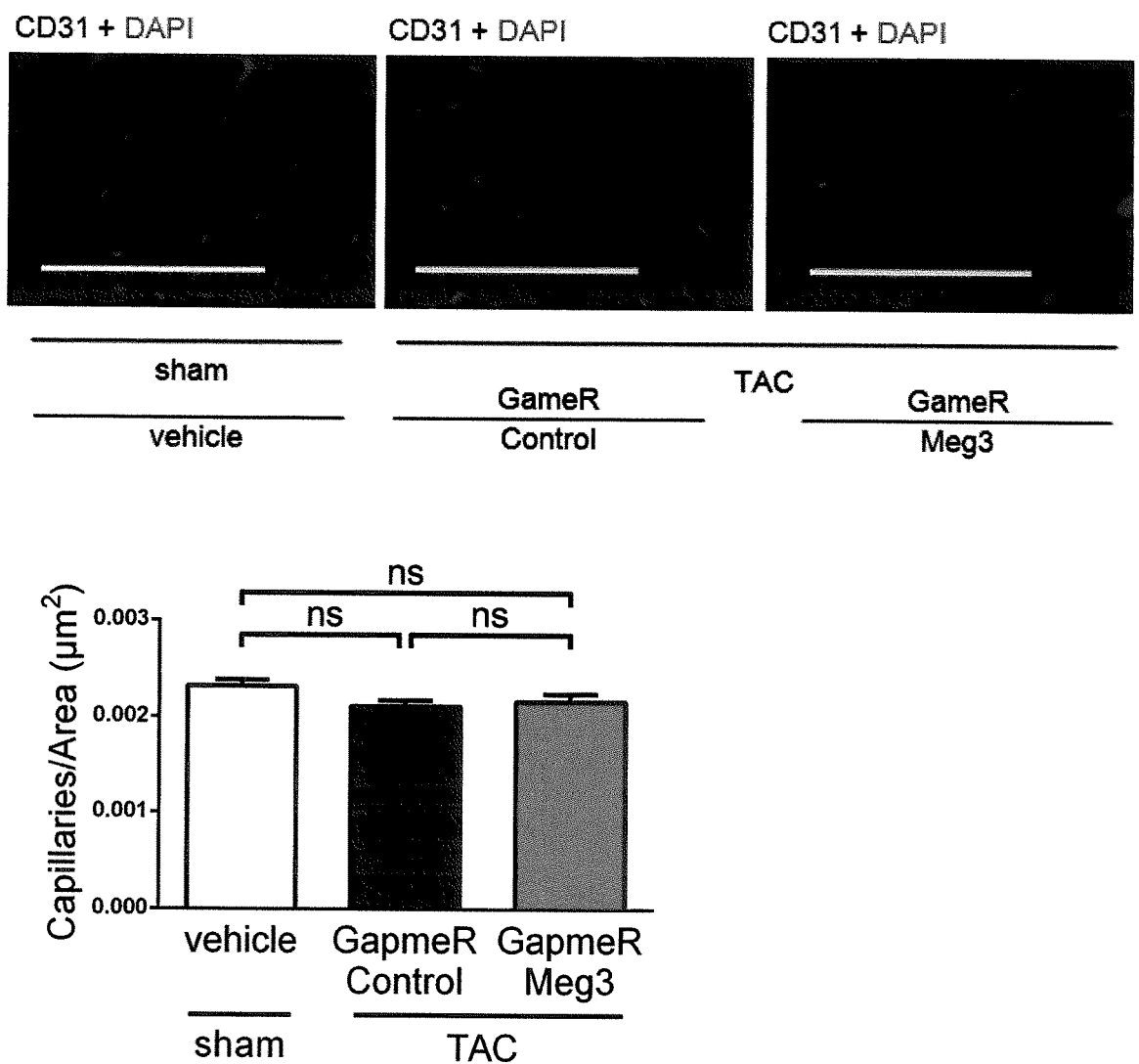

FIG. 13. Effect of Meg3 silencing on capillar density in mice undergoing 6 weeks of sham or TAC surgery. Scale bar=100 μm, n=7/8, FC=fold change, ns=not significant.

FIG. 14. Effect of Meg3 inhibition on LV wall thickness and LV mass in mice undergoing 6 weeks of TAC. (a) IVS and LVPW thickness in sham, and TAC mice with or without inhibition of Meg3, as measured via echocardiography (n=7/8). (b) LV mass in sham, and TAC mice with or without inhibition of Meg3, as measured via echocardiography (n=7/8). FC=fold change, *p≤0.05, **p≤0.01, ns=not significant.

FIG. 15. Lack of effect of Meg3 inhibition on LV diameters and on ejection fraction and fractional shortening following 6 weeks of TAC. n=7/8, FC=fold change, *p≤0.05, **p≤0.01, ns=not significant.

FIG. 16. Effect of Meg3 inhibition on $dP/dT_{max}$ and $dP/dT_{min}$ values of mice undergoing sham and TAC surgery with injections of GapmeRs. Parameters were obtained via Millar heart catheterization (n=7/5/6). (*p≤0.05, *p≤0.001, **p≤0.0001, ns=not significant).

FIG. 17. Pressure-volume loops and indicators of systolic/diastolic function in sham, and TAC mice with or without Meg3 silencing. (a) Characteristic changes in PV relationships obtained by vena cava inferior occlusion in sham, and TAC mice with or without Meg3 inhibition. (n=7/5/6). (b) ESPVR in sham, and TAC mice injected with GapmeR Control or GapmeR Meg3 (n=5/6/7). (c) EDPVR in sham, and TAC mice injected with GapmeR Control or GapmeR Meg3 (n=7/5/6). (p≤0.01, *p≤0.001, ns=not significant).

FIG. 18. Levels of fibrosis markers in human CFs following transfection with GapmeR targeting human Meg3. (a) All measurements were performed via real-time PCR normalizing specific gene expression levels to those of Hprt (n=3, *p≤0.05, p≤0.01, *p≤0.001, ****p≤0.0001, ns=not significant).

The examples illustrate the invention.

Example 1—Material and Methods

Chromatin Immunoprecipitation

For prediction of P53 binding sites on the Mmp-2 promoter the Jaspar core vertebrata database was used and a 1000 bp region directly upstream of the Mmp-2 transcription start site was scanned with the TP53 matrix model (Homo Sapiens). For ChIP, the MAGnify Kit (ThermoFisher) was used following the manufacturer's recommendations. $2 \times 10^6$ primary adult murine CFs were seeded in a 10 cm petri dish per experimental condition. Cross-linking of cells was performed directly on the dish without trypsinization. Sonication was performed on a Bioruptor UCD-200TM-EX for 16 cycles of 30 seconds ON, 30 seconds OFF at high power. 200.000 cells were used for each immunoprecipitation. For P53, 4 μg of a mouse monoclonal anti-P53 antibody (Cell Signaling 2524S) were used, whereas for IgG control IP, 4 μg mouse monoclonal isotype control (Cell Signaling 5415S) were used.

Transverse Aortic Constriction and lncRNA Profiling in Cardiac Fibroblasts

To generate cardiac pressure overload, male C57BL/6N mice (8 to 10 weeks old) were subjected to TAC as described previously[1]. For lncRNA microarray analysis, RNA from cardiac fibroblasts from sham or TAC groups (n=3 mice per group) obtained 13 weeks after surgery was subjected to global lncRNA profiling using the Arraystar Mouse LncRNA Microarray v 2.0 (Arraystarinc).

Isolation of Cardiac Cells for lncRNA Detection

Adult mouse cardiomyocytes were isolated according to the previously described retrograde perfusion method[2] that was slightly modified and expanded to also obtain cardiac fibroblasts, via a 1 h pre-plating step in AMCF medium containing 1% FBS (10.8 g MEM, 10% NaHCO3, 2 ng/ml vitamin B12, 1X Penicillin/streptomycin), and endothelial cells, via MACS sorting of CD146 positive cells using CD146 (LSEC) MicroBeads (Miltenyi Biotec).

RNA Isolation

Total RNA from frozen tissues, frozen cell pellets or cultured cells was isolated using RNeasy Mini Kit (Qiagen) or TriFast method (Peqlab) according to the manufacturer's instructions.

qRT-PCR Analysis for Microarray Validation and quantitative Detection of lncRNAs, mRNAs and Genomic Regions cDNAs were synthesized with the iScript Select cDNA synthesis kit (Bio-Rad), and real-time RT-qPCR analysis was performed using primers listed below and the iQ SYBR Green Mix (Bio-Rad) according to the manufacturer's protocol. Gene-specific expression levels were normalized to levels of hypoxanthine-guanine phosphoribosyltransferase (Hprt) or b-actin (ActB).

| Primer name | Primer sequence forward | Primer sequence reverse |
| --- | --- | --- |
| Mmu_Meg3 | 5'TCACCTCCAATTTCCCCTCC3' | 5'GCAAGCCAAGCCTTAAACCT3' |
| Mmu_Hprt | 5'GCGTCGTGATTAGCGATGAT3' | 5'TCCTTCATGACATCTCGAGCA3' |
| Mmu_ActB | 5'ATCAAGATCATTGCTCCTCCTG3' | 5'AGGGTGTAAAACGCAGCTCA3' |
| Mmu_Alpha-MHC | 5'GGTCCACATTCTTCAGGATTCTC3' | 5'GCGTTCCTTCTCTGACTTTCG3' |
| Mmu_Fsp-1 | 5'GCTGCCCAGATAAGGAACCC3' | 5'TGCGAAGAAGCCAGAGTAAGG3' |
| Mmu_Pecam-1 | Quantitect Primer Assay: QT01052044 (Qiagen, Hilden, Germany) | |
| Mmu_Gapdh | 5'GAAGGGCTCATGACCACAGT3' | 5'GGATGCAGGGATGATGTTCT3' |
| Mmu_Xist | 5'TCATCCGCTTGCGTTCATAG3' | 5'GAGATCAGTGCTGGCTAAATCAGA3' |
| Mmu_Neat-1 | 5'TGGCCCCTTTTGTTCATTAGC3' | 5'TGGAAGGCCATTGTTTCAGG3' |
| Mmu_Mmp2 | Quantitect Primer Assay: QT00116116 (Qiagen, Hilden, Germany) | |
| Mmu_Anp | 5'CCTGTGTACAGTGCGGTGTC3' | 5'CCTAGAAGCACTGCCGTCTC3' |
| Mmu_Bnp | 5'CTGAAGGTGCTGTCCCAGAT3' | 5'GTTCTTITGTGAGGCCTTGG3' |
| Mmu_Ctgf | Quantitect Primer Assay: QT00096131 (Qiagen, Hilden, Germany) | |
| Mmu_Tgf-beta I | 5'TCAGACATTCGGGAAGCAGT3' | 5'TGACGTCAAAAGACAGCCAC3' |
| Mmu_Tgf-beta II | 5'GCTTCGAATCTGGTGAAGGC3' | 5'CTATCGATGTAGCGCTGGGT3' |
| Mmu_Tgf-beta III | 5'CCGCTGAATGGCTGTCTTTC3' | 5'GGCTGAAAGGTGTGACATGG3' |
| Mmu_Mmp-9 | Quantitect Primer Assay: QT00108815 (Qiagen, Hilden, Germany) | |
| Mmu_Cdkn1a | 5'CCTGGTGATGTCCGACCTG3' | 5'CCATGAGCGCATCGCAATC3' |
| Hsa_Mmp-2 | 5'TGACATCAAGGGCATTTCAGGAGC3' | 5'GTCCGCCAAATGAACCGGTCCTTG3' |
| Hsa_Hprt | 5'AGGACTGAACGTCTTGCTCG3' | 5'GTCCCCTGTTGACTGGTCATT3' |
| Hsa_Meg3 | 5'GAAGAACTGCGGATGGAAGC3' | 5'CACGTAGGCATCCAGGTGAT3' |
| Hsa_Col1a1 | Quantitect Primer Assay: QT00037793 (Qiagen, Hilden, Germany) | |
| Hsa_Ctgf | Quantitect Primer Assay: Q100052898 (Qiagen, Hilden, Germany) | |
| Hsa_alpha-SMA | CCTGACTGAGCGTGGCTATT | GATGAAGGATGGCTGGAACA |
| Mmu_mmp2 promoter | 5'TCTCCAACTCTGTTCAGGCA3' | 5'TCTGGAAAGGAGGTGGGATT3' |
| Mmu_Cdkn1a promoter | 5'GGGTGGGGACTAGCTTTCTG3' | 5'CAGCCCCACCTCTTCAATTC3' |
| Mmu_mmp2 intron | 5'CGTGGTGTCTGAAACCTGGA3' | 5'CGCCAGGTTATGCGTCTTTG3' |
| Mmu_Gapdh promoter | 5'ATCCTGTAGGCCAGGTGATG3' | 5'AGGCTCAAGGGCTTTTAAGG3' |

The primer sequences in the above Table correspond to SEQ ID NOs 25 to 50 and SEQ ID NOs 53 to 70, wherein each pair of two consecutive SEQ ID NOs (e.g. SEQ ID NOs 25 and 26) corresponds to one of the above shown primer pairs.

Primary Adult Murine Cardiac Fibroblast Isolation

Primary mouse cardiac fibroblasts were isolated from the hearts of male C57BL/6N mice (8-10 week-old) by standard collagenase 2-based digestion at 37° C. The resulting cell suspension was pre-plated from 1 h up to overnight in DMEM with 1% penicillin/streptomycin and 10% FBS. After two passages the cell population is mainly composed of cardiac fibroblasts, as shown by immunostaining of vimentin and Fsp-1. Cells at passage 2-4 were used in all experiments. TGF-beta I treatment (R&D systems #7666-MB-005) was performed directly after transfection of cells, in 5% or 0.1% FBS, for 48 h at a concentration of 10 ng/ml.

Subcellular Fractionation

Fragmentation of cardiac fibroblasts into cytoplasmatic, nuclear-soluble and chromatin-associated fractions was performed as described previously[3].

Human Fibroblasts

Human cardiac fibroblasts were purchased from Promocell and cultured in Fibroblast Growth Medium 3 (Promocell) with 0.1 ml/ml FBS, 1 ng/ml Basic Fibroblast Growth Factor (Promocell) and 5 µg/ml insulin (Promocell).

Transfection with GapmeRs

Cells were transiently transfected with GapmeRs at a concentration of 50 nM for 48 h

```
Mouse Meg3:
                                          (SEQ ID NO: 51)
5'-AAAGCAGCGAGTGTA-3';

negative control A:
                                          (SEQ ID NO: 52)
5'-AACACGTCTATACGC-3'

Human Meg3 B:
                                          (SEQ ID NO: 71)
5'-TGAGCATAGCAAAGGT-3'

Human Meg3 C:
                                          (SEQ ID NO. 72)
5'-ACCAGGAAGGAGACGA-3'

Human Meg3 E:
                                          (SEQ ID NO: 73)
5'-CTTTGGAACCGCATCA-3'
```

All transfections were performed using Lipofectamine 2000 reagent (Invitrogen) according to the manufacturer's protocol.

Transcriptome Profiling After Meg3 Silencing

RNA was obtained from cardiac fibroblasts after GapmeR mediated silencing of Meg3 and subjected to microarray analyses (mRNA-Microarray_Ag4×44k_SC, Agilent Technologies). Go enrichment and KEGG pathway analysis was performed using DAVID 6.7 functional annotation tool.

Zymography

MMP2 activity in the supernatant of mouse cardiac fibroblast or in murine myocardial tissues was analyzed through gel zymography. Serum-free cell culture supernatant concentrated with Amicon Ultra-0.5 Centrifugal Filter Unit with Ultracel-30 membrane (Millipore) or myocardial tissue extracts were analyzed on a 10% SDS-gel containing 1 mg/ml gelatin, as described previously[4].

Injection of Gapmers

GapmeR-Meg3 (5'AAAGCAGCGAGTGTA3') (SEQ ID NO: 51) or GapmeR negative control B (5'GCTCCCTT-CAATCCAA3') (SEQ ID NO: 52) at a dose of 20 mg/kg (both from Exiqon) in saline (0.9% NaCl) as carriage medium, were delivered every 10 days by intraperitoneal injection, starting one week after TAC surgery. 6 weeks after surgery, cardiac function and morphometric changes were assessed by echocardiography (Vevo 2100, VisualSoncis) and Millar catheterization (1F, PVR-1000, Millar Instruments), and the hearts were removed for biochemical analysis.

Cell Cycle Analysis

For cell cycle analysis, cells were starved for 72 hours prior to transfection with GapmeRs and harvested 48 hours after liposomal transfection. The supernatant was removed and 200 µl Guava Cell Cycle Reagent containing PI were added and mixed well by pipetting up and down several times. After a 30 minute incubation at room temperature in the dark, single cells of each cellular sample were analyzed by flow cytometry with a Guava easyCyte instrument, measuring the size and the fluorescent intensity from each single event. The resulting raw data were further analyzed using the FlowJo software to achieve percentages of cells in G1, S or G2/M phase of the cell cycle.

Apoptosis Detection

For assessment of apoptosis, the Caspase-Glo 3/7 assay (Promega) was used following the manufacturer's recommendations. Briefly, 48 hours following liposomal transfection, 100 µl Caspase-Glo 3/7 reagent were added to each well of a 96-well-plate and mixed with the culture medium by pipetting several times. The plate was then kept at room temperature in the dark for 1 hour. Afterwards, the developed luminescence was quantified in a plate-reading luminometer (Synergy HT Reader, BioTek) as the mean luminescence of 11 reads taken at 1 minute time intervals.

Fluorescence Microscopy and Histology

For histological examination of fibrosis, paraffin sections of the left ventricle were stained with Sirius red and picric acid to visualize collagen deposition. The collagen content was calculated as the percentage of the area in each heart section. Cryosections of the left ventricular myocardium were visualized by wheat germ agglutinin stain coupled to Alexa Fluor 488 (Invitrogen). The cell surface area of cardiomyocytes was calculated using the NIS-Elements BR 3.2 package (Nikon Instruments Inc.). Immunofluorescence was performed against CD45 and CD31 for quantification of, respectively, inflammatory cell infiltration and capillary density in the heart. Fluorescent cells were counted using the NIS-Elements BR 3.2 package (Nikon Instruments Inc.).

Statistical Analysis

For statistical analysis, GraphPad 6 (GraphPad Software) was used. Data are displayed as means±SEM. Statistical comparison among two groups was evaluated by two-tailed unpaired Student's t test. For comparison of more than two groups, one-way ANOVA corrected with the Bonferroni or Turkey's post-test was performed. In all cases, P≤0.05 was considered statistically significant.

Example 2—Results

Meg3 in Cardiac Fibroblasts Isolated from TAC Mice

Maternally Expressed Gene 3 (Meg3 transcript variant 3, NR_027652.1) was found among the lncRNAs showing the highest normalized intensities ($\log_2$ of normalized intensity >8) and fold change (FC) values (FC TAC vs sham >2.5) in cardiac fibroblasts (CFs) isolated from mice undergoing 13 weeks of Transverse Aortic Constriction (TAC) compared to sham surgery.

Real-time PCR confirmed the downregulation of Meg3 in TAC fibroblasts, while no regulation was observed in cardiomyocytes or endothelial cells (FIG. 1A). Furthermore, expression levels of Meg3 in cardiomyocytes and endothelial cells of healthy mice represented, respectively, only 2% and 20% of the transcript levels found in CFs (FIG. 1B).

Chromatin Association and Silencing of Meg3 in Cardiac Fibroblasts

In CFs isolated from adult mice and cultured in vitro between passage 2 and 4, Meg3 is expressed as a chromatin associated lncRNA (FIG. 2A). By using antisense LNA GapmeRs, we were able to silence the expression of Meg3 in CFs by approximately 75% (FIG. 2B).

Effect of the Silencing of Meg3 on the Cardiac Fibroblast Transcriptome

Given the strict association to the nuclear chromatin compartment and the previous reports describing the role of Meg3 in transcriptional regulation of gene expression[5], the effect of Meg3 silencing on the cardiac fibroblast transcriptome was investigated via microarray analysis. GapmeR-mediated silencing of Meg3 resulted in the upregulation of 1041 genes and in the downregulation of 848 genes (FC ≥2, p-value ≤0.05) (FIG. 3A). GO term enrichment analysis of deregulated genes (FIG. 3B) revealed that silencing of Meg3 is strongly associated to the deregulation of secreted signaling molecules such as growth factors, cytokines and chemokines as well as of membrane-bound and extracellular proteins, including matrix metalloproteinases (MMPs).

MMP2 Transcription is Affected by Meg3 Levels

The transcription of matrix metalloproteinase-2 (MMP2), in particular, is affected by Meg3 levels both in the presence and in the absence of TGF-beta (FIG. 4A). Accordingly, the secreted active form of MMP2 is reduced in the supernatant of cultured CFs after silencing of Meg3 (FIG. 4B).

Expression of Meg3 and MMP2 in the Course of TAC

In vivo, myocardial expression of Meg3 and MMP2 is subjected to dynamic changes during the course of TAC. Meg3 is upregulated after 4 weeks of TAC, slightly downregulated after 6 weeks, and more strongly downregulated after 13 weeks (FIG. 5). Similarly, MMP2 is upregulated in the first weeks of TAC, likely peaking between week 4 and 6, and decreased again after 13 weeks (FIG. 5).

In Vivo Silencing of Meg3 in TAC Mice

Previous reports have suggested that inhibition of MMP2 might be beneficial for the heart, reducing hypertrophy and fibrosis in conditions of diastolic dysfunction[6]. Intraperitoneal injection of Meg3 antisense LNA GapmeRs was able to induce silencing of Meg3 in cardiac fibroblasts 5 days after injection (FIG. 6A). Therefore, TAC in adult mice and silenced Meg3 1 week after surgery (FIG. 6B) were performed.

6 weeks after TAC, silencing efficiency was analyzed via real-time PCR, as well as expression of MMP2 and of markers of hypertrophy and fibrosis. Successful silencing of Meg3 was associated with complete inhibition of the TAC-induced MMP2 increase (FIG. 7A). Myocardial expression of TGF-beta isoforms as well as of CTGF was reduced after silencing of Meg3 (FIG. 7B). Additionally, hypertrophic markers BNP and ANP showed a decrease in the TAC+ GapmeR Meg3 group compared to the negative control group (FIG. 7B). Histological analysis revealed a decrease in fibrosis levels and smaller cardiomyocyte cross-sectional areas (FIG. 7C+7D).

The left ventricular myocardial performance index, measured via pulsed Doppler echocardiography, revealed a functional improvement of the heart, with values of the index comparable to that of sham mice (FIG. 8).

Furthermore, pharmacological inhibition of Meg3 in vivo did not lead either to increased MMP9 expression, which has been reported to occur in late cardiac remodelling stages, overtaking MMP2 levels and leading to heart failure (FIG. 9) or to increased infiltration of inflammatory cells in the myocardium (FIG. 9).

Based on the above-described results, silencing of Meg3 in the heart is expected to be a promising therapeutic approach to achieve inhibition of MMP2 and improvement of cardiac function in conditions of left ventricular pressure overload, especially in Heart Failure with Preserved Ejection Fraction (HFpEF). As mentioned herein above, in particular this patient subgroup is in dire need of new cardiac therapeutic medications with a focus on inhibition of cardiac fibrosis. The anti-Meg3 approach is expected to be an ideal approach for this patient group.

Example 3—Further Results

Meg3 affects binding of P53 on the promoter of Mmp-2 in cultured mouse CFs The downregulation of Mmp-2 expression occurring following silencing of Meg3 was found to be mediated by P53. In fact, a P53 binding site was predicted in a 1000 bp region upstream of the Mmp-2 transcription start site using the Jaspar database. Chromatin immunoprecipitation showed that P53 can bind to such site when fibroblasts are stimulated with TGF-beta I (FIG. 10a). However, when expression of Meg3 is knocked down due to GapmeR transfection, binding of P53 to the Mmp-2 promoter does not occur, impairing Mmp-2 transcription (FIG. 10b).

Interestingly, the expression of the P53 target and cell cycle regulator Cdkn1a (p21) was not affected by the silencing of Meg3. Consequently, no changes in cell cycle progression or apoptosis were detected following Meg3 silencing in mouse CFs (FIG. 11).

Silencing of Meg3 in Vivo Impairs Activation of Myocardial MMP2 Following 6 Weeks of TAC Following injection of GapmeR Meg3 in mice undergoing 6 weeks of TAC, myocardial levels of active MMP-2 were detected by gel zymography. Preventive silencing of Meg3 was followed by a significant reduction of active MMP-2 levels (FIG. 12).

Silencing of Meg3 In Vivo Does Not Affect Capillary Density Following 6 Weeks of TAC Since both Mmp-2 and Meg3 have been described to influence angiogenesis (Boon et al., J Am Coll Cardiol 2016 December 13; 68(23):2589-2591 and Givvimani et al., Arch Physiol Biochem 2010 May; 116(2):63-72) capillary density was assessed in mice undergoing 6 weeks of TAC and injection of GapmeRs. No significant differences found between sham and TAC mice and between TAC mice receiving GapmeR control or GapmeR Meg3 (FIG. 13).

Silencing of Meg3 In Vivo Reduces LV Mass Following 6 Weeks of TAC and Ameliorates Diastolic Function Without Affecting Cardiac Contractility The reduced deposition of ECM and the lower levels of CMC hypertrophy in TAC mice injected with GapmeR Meg3 were reflected in a decreased thickness of both the interventricular septum (IVS) and the LV posterior wall (LVPW), as measured via echocardiography. Accordingly, the echocardiographic LV mass was reduced in the TAC+ GapmeR Meg3 group compared to the TAC+GapmeR Control group (FIG. 14).

On the other end LV diameters, as well as ejection fraction and fractional shortening, were not affected by the silencing of Meg3 (FIG. 15).

Besides the presence of a better myocardial performance, assessed via pulsed Doppler echocardiography, hemodynamic measurements confirmed that silencing of Meg3 is associated with a significantly better diastolic function following TAC. On the other hand, cardiac contractility was not significantly affected by the levels of Meg3, which therefore seem to selectively affect passive properties of the heart, rather than myocardial contractility (FIGS. 16 and 17).

Silencing of Meg3 In Human CFs Leads to Decreased RNA Levels of Mmp-2, Col1a1, Alpha-SMA and Ctgf Human CFs were transfected with 3 different GapmeR designs targeting human Meg3. Levels of Mmp-2, Col1a1, alpha-SMA and Ctgf were measured via real-time PCR 48 hours following transfection. All genes were expressed at lower levels following Meg3 knockdown in human CFs (FIG. 18).

Literature

1) H. A. Rockman, R. S. Ross, A. N. Harris, K. U. Knowlton, M. E. Steinhelper, L. J. Field et al. Segregation of atrial-specific and inducible expression of an atrial natriuretic factor transgene in an in vivo murine model of cardiac hypertrophy. Proc. Natl. Acad. Sci. U.S.A. 88,8277-8281 (1991).

2) T. D. O'Connell, M. C. Rodrigo, P. C. Simpson. Isolation and culture of adult mouse cardiac myocytes. Methods Mol. Biol. 357,271-296 (2007).

3) D. S. Cabianca, V. Casa, B. Bodega, A. Xynos, E. Ginelli, Y. Tanaka et al. A long ncRNA links copy number variation to a polycomb/trithorax epigenetic switch in FSHD muscular dystrophy. Cell 149,819-831 (2012).

4) Toth M., Sohail A., Fridman R. Assessment of gelatinases (MMP-2 and MMP-9) by gelatin zymography. Methods Mol Biol. 2012; 878:121-35.

5) Mondal T., Subhash S., Vaid R., Enroth S., Uday S., Reinius B., et al. MEG3 long noncoding RNA regulates the TGF-β pathway genes through formation of RNA-DNA triplexstructures. Nat Commun. 2015 Jul. 24; 6:7743.

6) Matsusaka H., Ide T., Matsushima S., Ikeuchi M., Kubota T., Sunagawa K., et al. Targeted deletion of matrix metalloproteinase 2 ameliorates myocardial remodeling in mice with chronic pressure overload. Hypertension. 2006 Apr.;47(4):711-7. Epub 2006 Feb. 27.

The invention claimed is:

1. A method for treating or preventing cardiac remodeling comprising administering a therapeutically effective amount of a nucleotide-based inhibitor that inhibits expression and/or activity of maternally expressed 3 (Meg3),
   wherein the nucleotide-based inhibitor is a siRNA, a shRNA, or an antisense oligonucleotide, targeting within SEQ ID NO:8 or SEQ ID NO:21,
   wherein the nucleotide-based inhibitor comprises
   (a) a nucleic acid sequence that comprises a nucleic acid sequence being fully complementary to at least 12 continuous nucleotides of a nucleic acid sequence selected from SEQ ID No: 1 to 20, or 21,
   (b) a nucleic acid sequence that comprises a nucleic acid sequence which is at least 70% identical to the complementary strand of one or more nucleic acid sequences selected from SEQ ID No: 1 to 20, or 21,
   (c) a nucleic acid sequence that comprises a nucleic acid sequence according to (a) or (b), wherein the nucleic acid sequence is DNA or RNA, or
   (d) an expression vector expressing the nucleic acid sequence as defined in any one of (a) to (c).

2. The method according to claim 1, wherein the cardiac remodelling is Heart Failure with preserved Ejection Fraction (HFpEF).

3. The method according to claim 1, wherein the cardiac remodelling is Heart Failure with reduced Ejection Fraction (HFrEF), myocardial infarction related cardiac remodelling, genetic cardiac disease associated cardiac remodelling, cardiac hypertrophy cardiac fibrosis, or any combination thereof.

4. The method according to claim 3, wherein the cardiac hypertrophy is ventricular hypertrophy, and/or wherein the cardiac fibrosis is ventricular fibrosis.

5. The method according to claim 4, wherein the ventricular hypertrophy is left ventricular hypertrophy.

6. The method according to claim 4, wherein the ventricular fibrosis is left ventricular fibrosis.

7. The method according to claim 1, wherein the expression vector expressing the nucleic acid sequence is controlled by a heart-specific promoter and/or a fibroblast-specific promoter.

* * * * *